US008617812B2

(12) United States Patent
Richt

(10) Patent No.: US 8,617,812 B2
(45) **Date of Patent: *Dec. 31, 2013**

(54) POLYMORPHISM IN BOVINE PRION PROTEIN GENE SEQUENCE

(75) Inventor: Juergen A. Richt, Manhattan, KS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 341 days.

This patent is subject to a terminal disclaimer.

(21) Appl. No.: 12/969,744

(22) Filed: Dec. 16, 2010

(65) Prior Publication Data

US 2011/0123999 A1 May 26, 2011

Related U.S. Application Data

(63) Continuation of application No. 11/787,784, filed on Apr. 18, 2007, now Pat. No. 7,867,710.

(60) Provisional application No. 60/793,760, filed on Apr. 21, 2006.

(51) Int. Cl.
*C12Q 1/68* (2006.01)
*C12P 19/34* (2006.01)
*C07H 21/04* (2006.01)

(52) U.S. Cl.
USPC ............ 435/6.1; 435/91.2; 435/7.1; 536/23.1

(58) Field of Classification Search
None
See application file for complete search history.

(56) References Cited

U.S. PATENT DOCUMENTS 7,867,710 B2 * 1/2011 Richt .......................... 435/6.18

OTHER PUBLICATIONS

GenBank BTA000291 (Mar. 6, 2004), 'TPA: Bos taurus prp gene for prion protein', from www.ncbi.nlm.nih.gov, pp. 1-27.*
Sander P. et al. Neurogenetics (2004) 5:19-25.*

* cited by examiner

*Primary Examiner* — Stephen Kapushoc
(74) *Attorney, Agent, or Firm* — John Fado; Randall E. Deck; Lesley Shaw

(57) ABSTRACT

A specific, non-synonymous SNP in the Prnp gene encoding the bovine prion protein affects the susceptibility of bovine animals to bovine spongiform encephalopathy (BSE). Depending on the number of octapeptide repeat units present in the Prnp gene, the position of the SNP is either nucleotide 631 of exon 3 (codon 211) when the Prnp gene comprises six octapeptide repeat region sequences, nucleotide 607 of exon 3 (codon 203) when the Prnp gene comprises five octapeptide repeat region sequences, or nucleotide 655 of exon 3 (codon 219) when the Prnp gene comprises seven octapeptide repeat region sequences. Alleles of the bovine Prnp wherein the SNP at these positions is lysine (K) at the corresponding amino acids (i.e., 211, 203 or 219) in the bovine prion protein are all indicative of increased susceptibility to BSE in comparison to alleles which encode glutamic acid (E) at the same position. This SNP may be used as a marker for selecting bovines susceptible to BSE for disposal and/or removal from breeding, the human food and animal feed supplies.

16 Claims, 7 Drawing Sheets

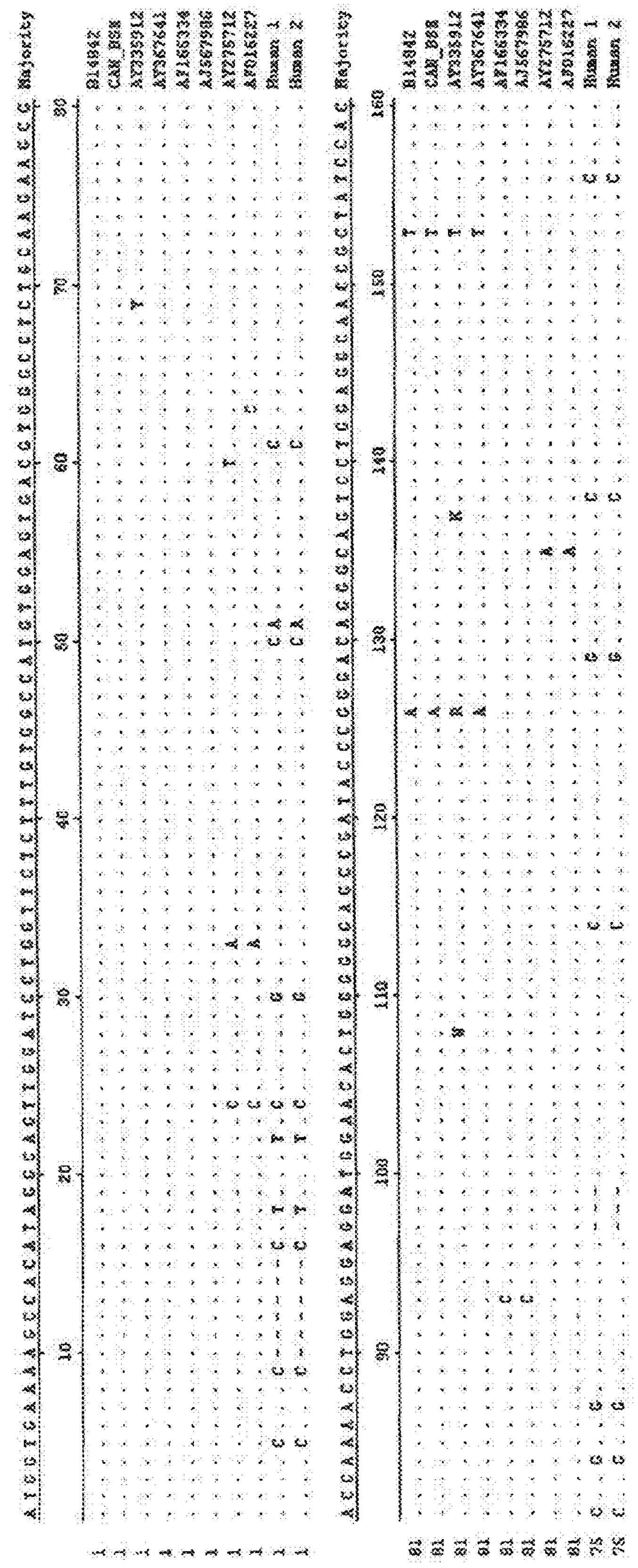
FIGURE 1A1

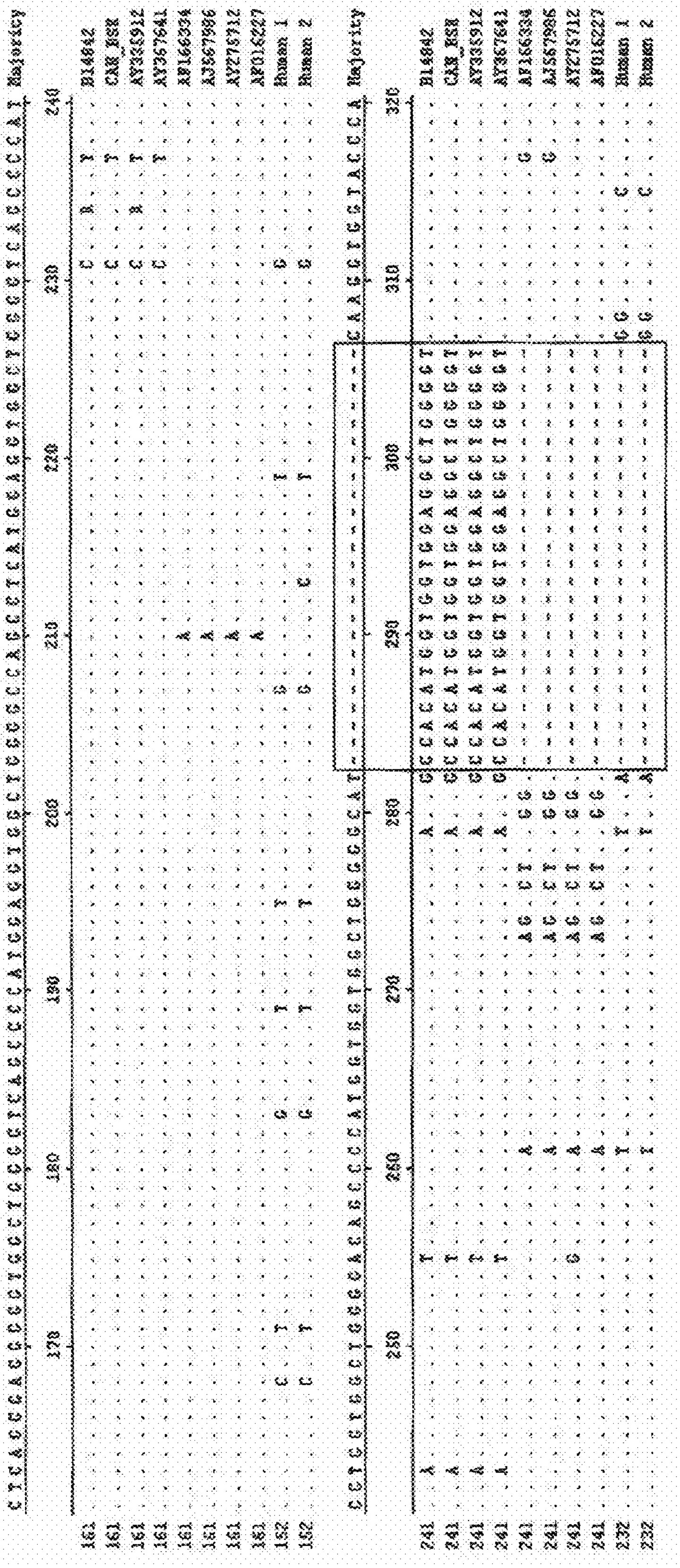
FIGURE 1A2

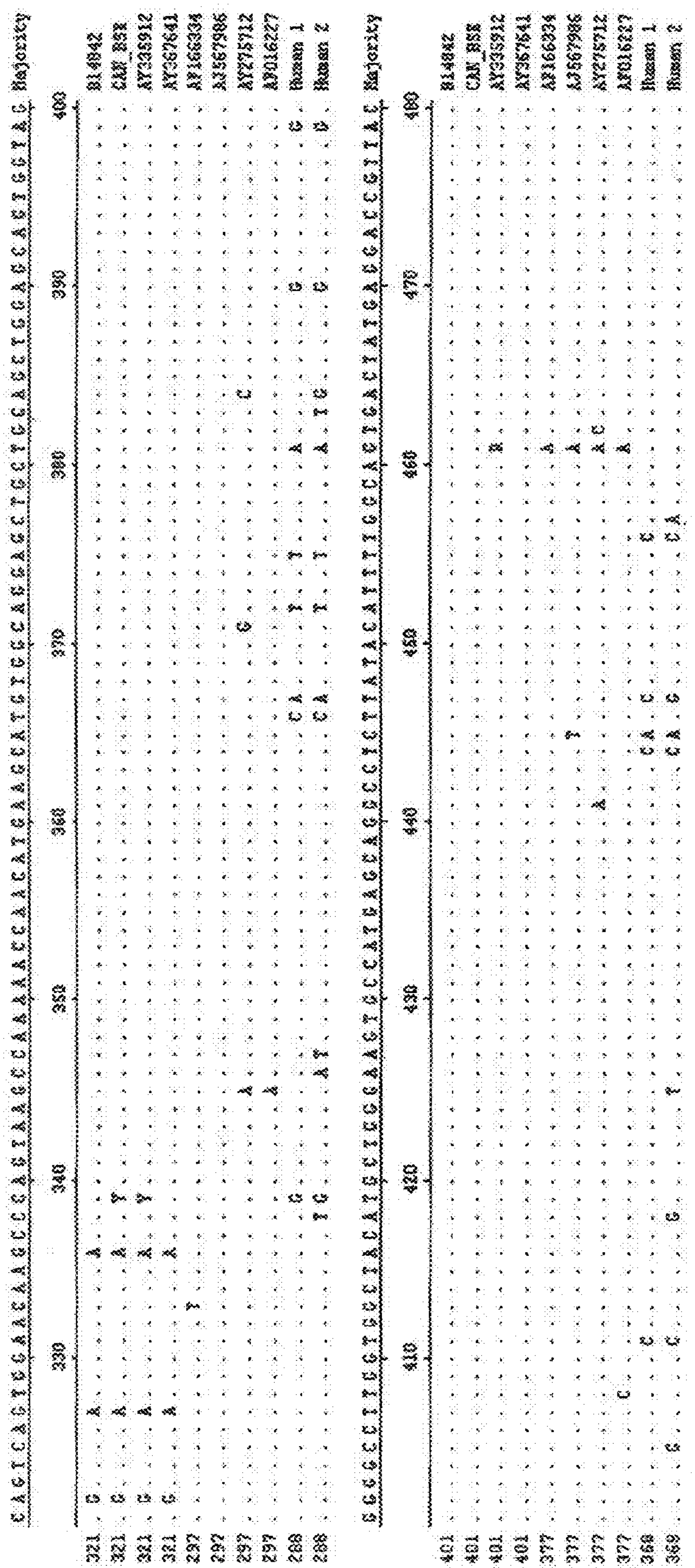
FIGURE 1A3

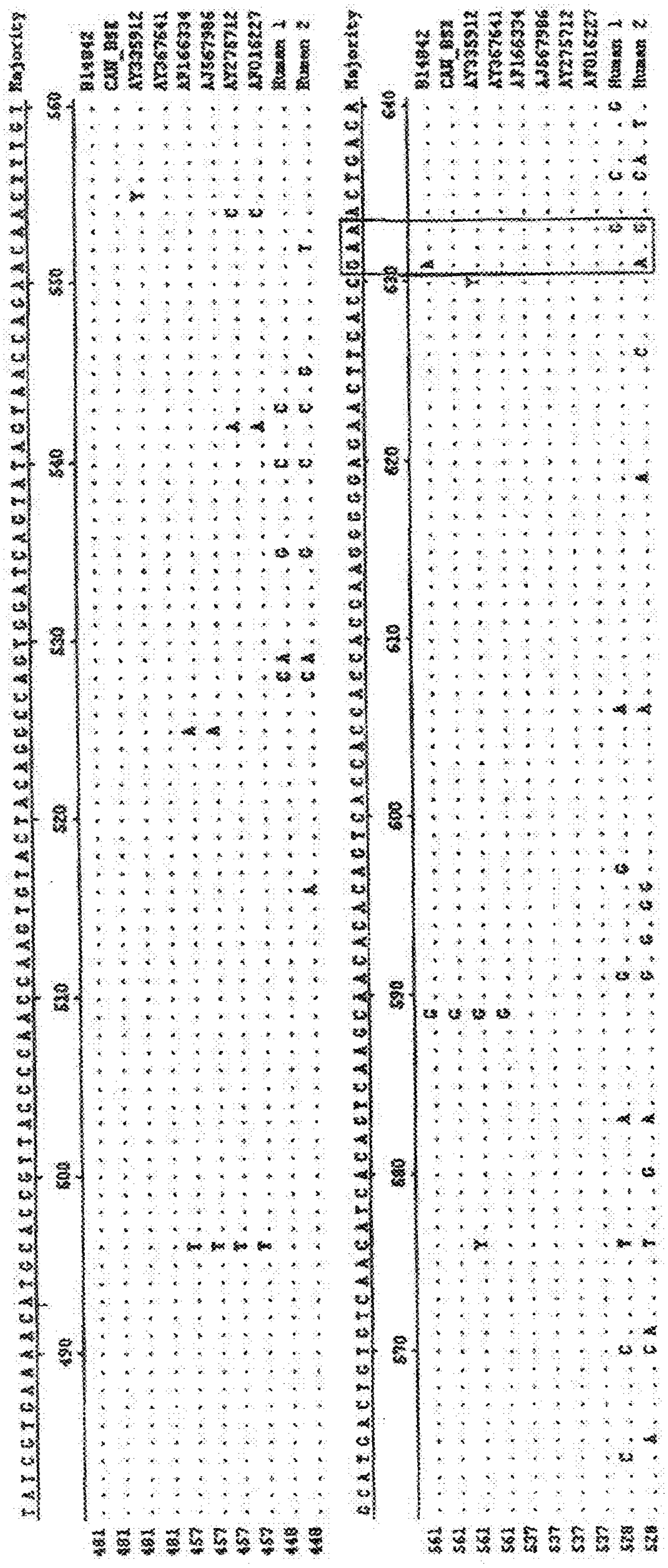
FIGURE 1A4

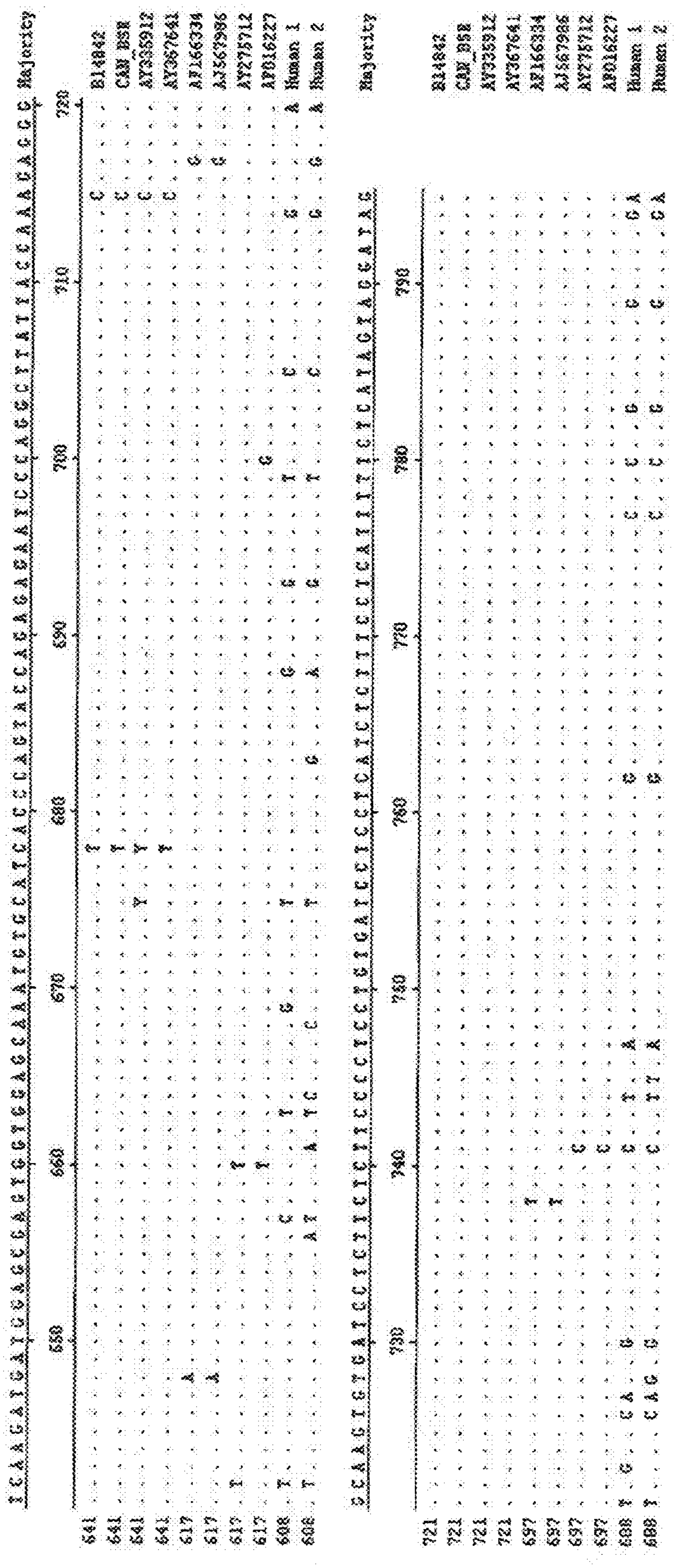
FIGURE 1A5

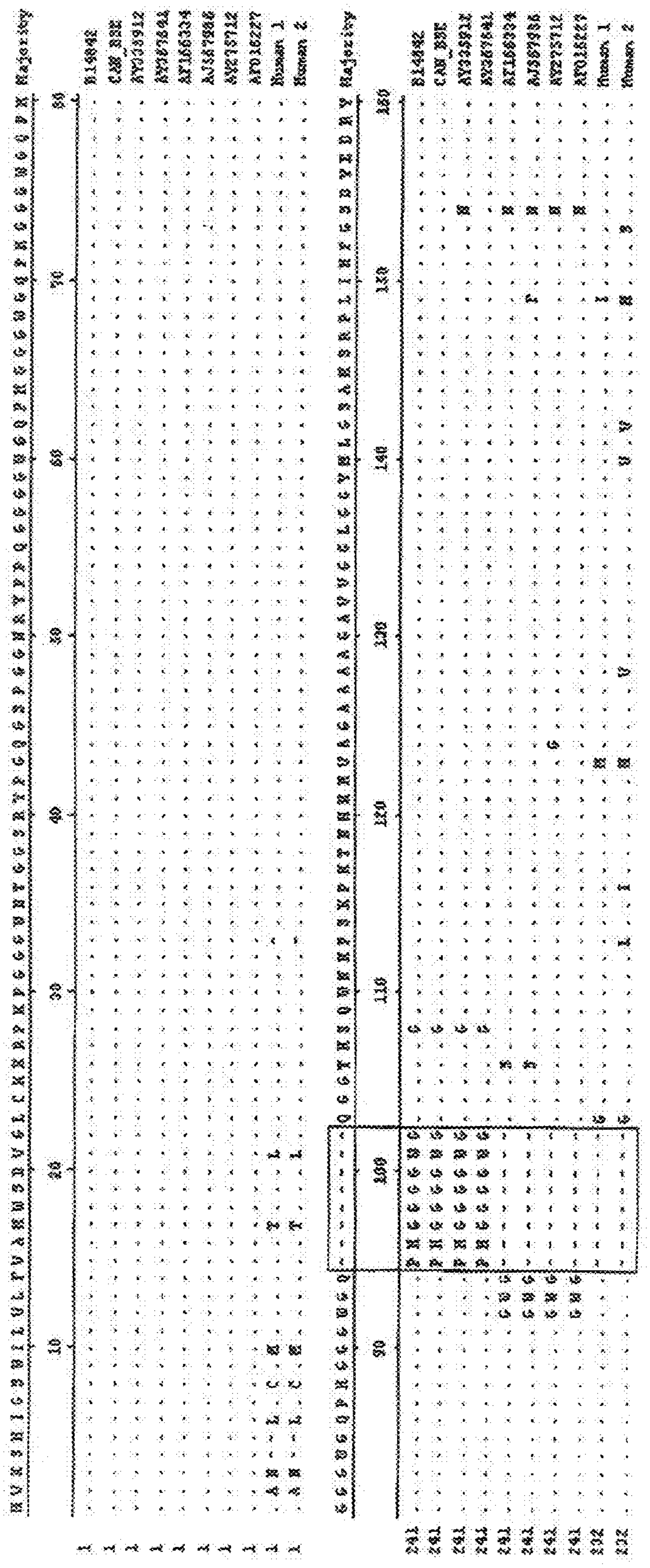
FIGURE 1B1

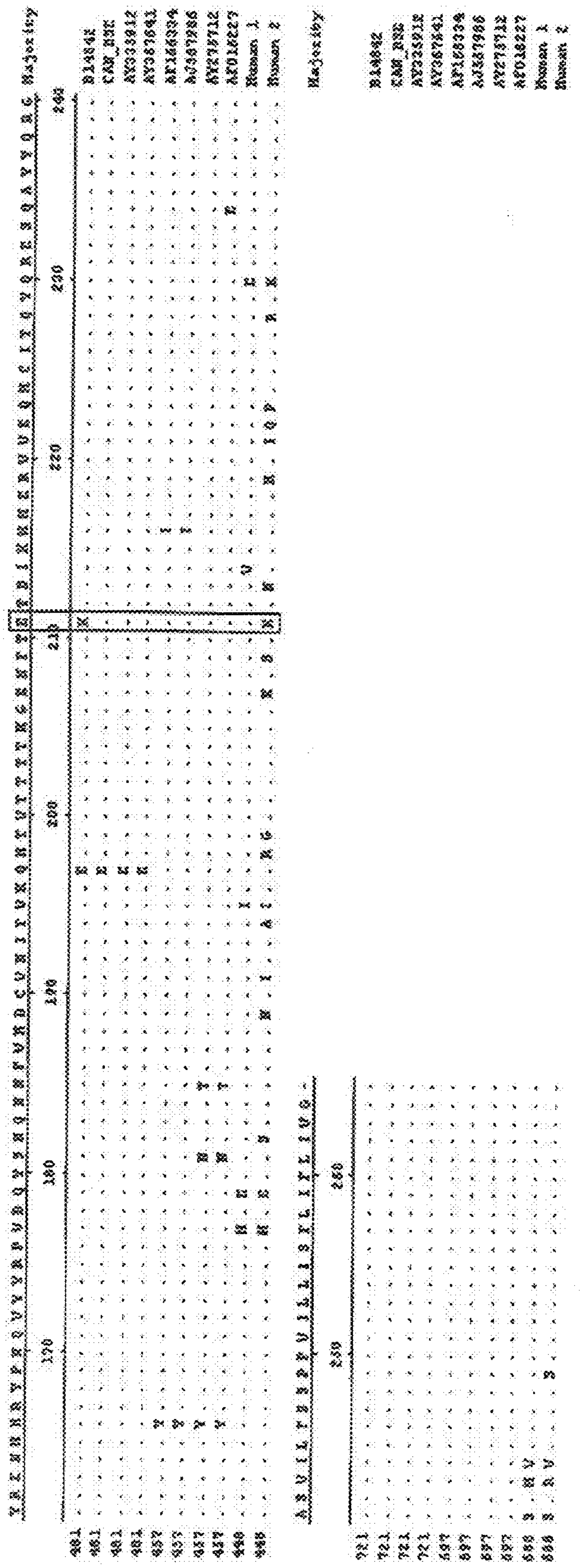
FIGURE 1B2

SEQUENCE LISTING

```
<160> NUMBER OF SEQ ID NOS: 27

<210> SEQ ID NO 1
<211> LENGTH: 78056
<212> TYPE: DNA
<213> ORGANISM: Bos taurus

<400> SEQUENCE: 1

taggaataat caatattgtg aaatgaccat ataccaaatg caacctacag attcaatgag     60

atctccatct aacttccaat agcatttttc acagaagtag aacaaaaaat ttcacaattc    120

atatggaaac acaaaaggcc ctgaatagcc aatgcagtcc tgagaaagaa gaatggagtt    180

ggaggattca accatcctga ctttagatta tactacaaag ctacagtcat caagacagta    240

tggtattggc ataaaaacag aaatatagac aaatggaaca agacagaaag cccagaaata    300

agcccatgaa cctatgggta ccttattcct gacaaaggaa gcaagaatat acaatggggc    360

agacagcctc ttcaataaat ggtgctggga aaactggaca gctacatgta aaagaatgaa    420

attagaacac ttcctaacac caacagttca gttcagttca gctggtcagt cgtatcgact    480

ctttgcaacc ccatggactg cagcatgcca ggcttccctt gtccatcacc aactcctaga    540
```

-continued

```
gcttactcaa actcatgtcc attgagttgg tgatgccatc caaccatctc atcctctgtc    600
gtccccttct cctcccacct tcaatcattc tcagcatcag ggttttttcc aatgaggcag    660
ttctttgcat caggtggcca aagtattgga ctttcagctt cagcattagt ccttccgatg    720
aatattcagg actgatttcc tttaggatgg actggtttga tcttgcagtc caaatgactc    780
tcaagagtgt tctccaacac cacagttcaa aagcatcaat tcttcagcac tcagctttct    840
ttatagtcca actctcacaa ccatacatga ctactggaaa aaccatagct ttgactagat    900
ggagctttgt tggcaaagta atgtctctgc tttttaatat gctgtctagg ttggtcataa    960
cttttcttcc aaggagcaag catctttaat ttcatggctg cagtcaccat atgcagtgat   1020
tttggagccc ccaaaataaa gtctgtcact gtttccactg tttccccatc tatttgccat   1080
gaagtgatgg gaacagatgc catgatctta gtttcctgaa tgttgagttt taagtcaact   1140
ttttcactct cctctttcac tttcatcaaa aggctcttta ggtcttcttc tcttaaccat   1200
aaggatggtg tcatctgcat atctgaggtt attgatattt ctcctggcaa acttaattcc   1260
agcttgtgct ttatccagtc cagcatttct cgtgatgtac tctgcatata aattaaataa   1320
gcagggtgac aatatacagc ctcaatgtac tcctttcctg atttggaacc agtatgttgt   1380
tccatgtcta gttctaactg ttgcttccta acttgcatac agatttctca ggaggcaggt   1440
caggcgttct ggtattccca tctctttaag aatttcccac agtttgttgt gatccacaca   1500
gtcaaaggct ttggcacagt caataaagca aaaatggatg tttttctgga acgctcttac   1560
tttttcgatg atccaatgga tgttggcaat ttgatctctg attcctgtgc cttttctaaa   1620
tccagcttga acatctggaa gttcatggtt catgtacttt tgaagtctgg cttggagaat   1680
ttgagcatta ctttgctagt gtgtgagatg agtgtaatca tgcagtagtt tgagcattct   1740
ttggcattgc ctttctttgg gattggaatg aaaactgacc ttttccagtc ctgtggccac   1800
tgctgagttt tctaaatttg ctgccatatt gagtgcatca ctttcacagc atcatctttt   1860
aggatgtgaa atagctcaac tggaattcca tcacctcccc tagctttgtt cataatgatg   1920
cttcctaagg cccacttgac ttcacattct aggatgtctg gttctaggtg agtgatcaca   1980
ccatcatggt tatctgggtc atgaagttct ttcttgtaga gttcttctgt gtattcttgc   2040
cacctcttct taatatcttc tgcttttgtt aggtccatac catttctgtc ctttattgtg   2100
cccatctttg catgaaatgt tcccttggta tctgtaattt tcttgaagag atctctagtt   2160
cttcccattc tattgtctcc agggtgacca cccccagacc ctgtacctgg ggtcatataa   2220
ccacagtttc cacagtgaca tcccttccaa accctgaact tggggttgca cgtccatgtt   2280
ctccagcgtg acacaccctc ttggaccatg cactggggtc acatgtccag gttccaggct   2340
aacacccccc cccatactct atacctggca tcaacgtcct catacagcag ggtgaccgaa   2400
ccctcaacat catgtacctg gtgttgaaac tccacagttt ctgcacctca tcagaccttg   2460
tacctggagt cacatgtcca cagtctctag ggtgacagca cttcaccaga cctttgacca   2520
gtgttcacac atccagtctc cagggtgatg cccacttcca gaccctgtac ctggggtaca   2580
tgttcacagt ctccagggtg acagccccccc agactctgta gctgggttaa cagacccacc   2640
tttccagggt gactacacca ctccatattg tgcacctggg gtcacacatc cacaatctct   2700
ggggtgacct ctcccagacc ctgtacgtgg gtcacacatc cacagtccca gggtgacccc   2760
acttcccaga ctgtggaact gggttcacat gtccacagtt tccaggtgaa tccccctccc   2820
caaagcctgt acctggggtc acacatccac agtctccaga gtgaccctag cctccagacc   2880
ctctccctgg ggtcacatgt ccatggtcta cagggagata cccctcccag aacctgcacc   2940
```

-continued

```
tggggtcaca tggccacagt ctccagggtg aacccctacc agaccctgta cctggggtca   3000
catgttcaga gtctccaggg ttacctgcct cccagaccct gcaccttggt tcacatgtct   3060
gcagtctcca gtgtgacccc actcctgtac ctgtggtcac atgtgcagat tccagggtga   3120
cacccctccc agaccctgca cctggggtca cacgtatgcc atctccaggg tgaccccgcc   3180
tcaccagacc ttttacctgg ggtcacacct tcacagtctc cagggtaacc cccccaccca   3240
gactctgcac ttggggtaca aatccacagt ttccagggtg acaccccctc agaccttcta   3300
cctgaattca gagtttgata gcctcctggg agaccccacc acaccagcga gtgcacctgg   3360
cttcacacgt ccacagcgtc caggatgaca tgcccccaga ccctgtacct agggtcacat   3420
atctctagtt ccctggtgac ccctccaaga ccctgaacct ggggtcatat gtctgcagtc   3480
tccagggtga ccaaccacag acactctacc tggggtaata tattcacagt ctacagggtg   3540
acaacccact cagaccctga acctggggac acatgtccac ggtctccagg gtgatcacac   3600
actccagacc ctgtacctgg ggtcacatat ccacagtctc cagggaaacc caactgccca   3660
tactgtgcac ctggggggtca cacatccagt ctccagggtg accccccgcc ccatatcctg   3720
taccttgggc cacatgacct cagcctccag ggtgacccca ccctcaacat catttacctg   3780
gggccaaatc tccacactct ccagggtgac ctcctcccag accctgcacg tggggtcaca   3840
tgtccacagt ctccagggtg accccatgtc acagatcctg cacctgagtc acatgtcaac   3900
cgtctccatg gtgacccctc ccagactgca cctggggtca catatccata gttcccatgg   3960
tgatcccacc ctggccctgt acctgtggtc acatgtccac agtttcaggg tgagttccct   4020
cccacgttct gtacctgagg tcacatgtcc atagtctcca gggtgacccc atcttctaga   4080
cattgtacca gggttcacag atccacagtc tccagggtga tctccctctc cataccctgt   4140
acctggggtc aacatcctca gcttccagga tgacccaatc ctcaacatcg tgtaccgtgg   4200
gtcaaacgtc cacagtctcc agggtcactg cacctcacta gaccttgtac ctggggtcac   4260
atgtgcacag tctctagggt gacattacct caacatacct tttaaatggg ttcacacgtc   4320
cacagtctcc cagggtgact cccctctcag cctcctgcac ctgagataca cattcacagt   4380
ctccagggtg acatcccccc cagacactgt acctgggttc acaggtccac ctcctccagg   4440
gtgacctcac cacaccagac cacgcacctg tgatcacaca tccacagtgt ccagggtgac   4500
accctcccag atcctgtacc taaggtcaca tatctacagt tccctgagag accctcccaa   4560
accctgtacc tgggtcacac atccacagtc ccagggtgac cccacttccc agactgtgaa   4620
accgggttca catatcaata gtttccaggt gaattcccct ccccaaaccc tgtacctagg   4680
gtcacacgtc cacagtccca gggtgaccct agcctctacc tggggtcaca tgtccacatt   4740
ctacagggtg acccccctcc caggccctgc tcctagggtc atatggccag tttccacagt   4800
aaacccttcc cagaccctgt acctggggtc acatgtccag agtctccagg gtgatccaca   4860
tcccaaactc ttcacctggc atcacacgtc catagtctca agggtgacac cctcccagac   4920
tctgaacctg gggtcacatg tccacagtct ccagggtgac ccccacccga ccctgcccct   4980
ggggtcacac gtcttcagtc tccagggtga cacccctccc cagacactgt aactagagcc   5040
acatgtccac agtctacaag ggtgaacccc gccccccccc cataatctgc atgtgggttc   5100
acatatccac agtctccttg gtaaccttgc ttcccagtaa cggcacctgg attgcacatc   5160
cacagtcttc atggtgaccc cctcccagac tctgcacctg agttcaaatg tctacagtct   5220
ccagggtgac ccctcccaaa ccctgcagag ggcctcacat gtccacagtc tccaggctga   5280
acccccctcc cagaatctat acctggagtc acatgtccac agtctccagg gtgacacccc   5340
```

-continued ctcccccaga ccttggggt cacattgaaa cagtctccag gtgaccatct tcccagaccc 5400
tgcacctagg gtcacaagcc cacatctcca atgtgacccc tctcctgctc caggggtcac 5460
atgtccacaa attccaaggt gacacctctc ccagacactg cacctgggtt cacatgtccc 5520
actgtctcca gggtgacaac ccccatactc tgtacctggg ttcacaggtc cacagtctct 5580
agggtgactc tgccacatca gactgcacag ctgtgggcac atgtccacag tttccagggt 5640
ggcaccctcc cagatcctgt acccagggtc acatatttac agtcccctgg gttaacactc 5700
ccagaccctg tacctgaggt catttgtcca cgttgtccag ggtcaaccct tcccagaccc 5760
tacacctcgg ctcacatgtc cacagtctcc agggtgacct cctcccaacc ctgaacttgg 5820
agtcacatgt ccagtctcta gggtgatcac ccccataccc tgtacctggg atcacaaaac 5880
tacagtctcc agggtgaccc tgtgcccaga cactgaatct ggggtcacac atccacagtc 5940
tccagtgtga tgcccactcc cagaccatgc accaggggtc acacatccac agtctccagg 6000
gtgacagcct ctgagaccct gaacctgggg tcacatgccc acagtctaca gggtgacgac 6060
ccctcccaga ccacatacat gggttcacag gttcacagtc tccaggataa caccctccca 6120
gaccctgtac ctatggacac ctatctacaa tccccttggt gtcccctccc agacactata 6180
cctgggttca catgtccaca gtcttcaggg tgacaccctc cagaccctgt acctagggac 6240
acctatctac agtccccttg gtgtcccctc ccagacacta tatctggatt caaatgtcca 6300
cagtctccag gttgacccca ccctcaagaa cctctacctg tagtcatatg accacagtct 6360
ccagtgtaaa cccacctccc atatcctgca cctggagtac atgtccagtc tccagggtga 6420
ccccacagtc cagaccctgt acatagggtc acagacctca gcctcaagag tgatactctc 6480
ccagagtttt tacctggggc cacatgttca tagtctccag ggtgatcctc tctcaactct 6540
gcacctgggg tcacacatac aaagtctcca ggtaacaccc cccaataccc tgtgcctggt 6600
gttgcacatc cacagatttc acagtgaccc cacctcccgg accctgcatc tgaagtcaaa 6660
tgcccacagt ctccagtgta aactcacatc ccatgctgtt cctggggtaa atgtccacat 6720
tatccaggat gaccccacct cccagaccct gttccttggg tctcacttac acagtctcca 6780
gagtgtcccc acctctcaga ccctccatct gggatcgaac attgccagta tccagggtga 6840
ccccctccca gactctacac ttggggtcac atgtccagag tttccagggt gactgcctcc 6900
cgaacctgta gctgtggtca caggtccaca gtcttcaggg tgacacccct ctccagacaa 6960
tgtatctgga gtcacacatt cacagtctgc taggcgaacc cagcccccaa accctgcaca 7020
tgggacccca tgttcagtgg ggagtgttga ctaccagcct acaacaacca gctggctgtt 7080
gctgtcagca gcctaattgg gtgaaaaatg gactgggtga tgacttccca ataagaagtg 7140
gcaagtagca tgttcctttc agaaaactca aataatgaac caaagttgtt gtcataatgt 7200
acagacaaat gacctggtgt gtttcttcat ggttggttga gtctgcaact atccaccttt 7260
cccaggatga tcatatagat tttgccatat tactttgatt ccagcctcaa cataacatgt 7320
ttccctgtac atttagagct gggtaaagac actcctggag aaggcaatgg caccccactc 7380
cagtactctt gcctggaaaa tcccatggat ggaggagcct ggtaggctgt agtccatggg 7440
gtcacgaaga gtcagacaca attgagtgac tttactttca cttttcactt tcatgcattg 7500
gagaaggaaa tggcaaccca ctccagtgtt cttgcctgga gagtcccagg gacgggggag 7560
cctggtgagc tgccatctat ggggtcgcag agtcggacac gactgaagca acttagcagc 7620
agccgcagca aagacactcc tagtgtacaa acactgtaca gtttgaggag tatagacagc 7680
agtggagagt gctctatgaa tgtggatggc caggtctgtt tttaccctga gtaggtgaaa 7740

-continued

```
cgtactgtca ggtgacctca cagcaagaag tggcaagctg cctgtcatga gaagtgaagt   7800
tgcccactca tatgcgactc tttgcaatcc catggactgt agcctatgga ggtcttctgt   7860
ccatggaatt ttccagtcaa gagtactaaa gtgggttgcc aattcttttt ccagggaatc   7920
ttcgcgacct gagtatcaaa cctgggtctc ccacatcgca ggcagacact accctcttag   7980
ctaccacgga agcccaccag attcattgaa aactcaactg tttacccgaa gttgttctgg   8040
gattgaagag tagaatgagc ctgctgtgtt tttctgccag gtgggatgct gtaactacac   8100
aggtttcaca gggggaaatg actgctttgg aacgtccgat cccaattcca ggttcacaaa   8160
aagttgtctc cctgcagttt taaagctgtg taaatgcctt cctaggacac aatgggctct   8220
ctgtgaatgt tgacttctgt atgtgttctt accctattca gcgaaaacag tactgtcaga   8280
ggacttccca tcaagaagtg gcaagcagag tgtttctctc aggtaacaga agtacttgat   8340
gagacttgca gtcctaaaga agggaaaaac gacccgtgtg cttttccgtc aggctggaga   8400
ttgcaagtat tccaggtttg ctaggtgaaa atactgcttt ctcttcaggc cccgagttct   8460
acgttcagag aaacatttcc acacaggttc agagctgtgc caagattcca agaacacact   8520
gtacaatttc tcagaaaaga cttcagtgaa gaatgtcctg caagtggttc tgccataatt   8580
gttaccctga gtgggtggaa ttacactgtc agatgacttt ttagcattaa aaagcaagtg   8640
cctatgcttt cagaaaaggc agatactaaa gctgcgctcg taagaaacag gcaaatgaac   8700
ccgtgtgcat ttctttcagg cttaagactg caaccaccct gcagttacac gaaaaagtgc   8760
tgcttctgcc attaggctcc aaatcccatg tgaacagaaa taaatccccc tgtcattaga   8820
aagctgtgta agtgagccca ggccagaatg caccatacca tgagtaaaga ggtcagtggg   8880
gagtgttctg agagttcaat agtgagtgtt ctggaagtgt tgactgccat acctgtagtc   8940
agcagcctaa tttggtgaaa ctggactggg tgatgacttt ccagtaagaa ggagcaagct   9000
gcaattacct ttcagaagac tcataatggc ccaaagctgt tgtaataatg cccagacaaa   9060
tgagtcactg cgtttcttcc tagctggttg gtggctgcaa ctatccaggt ttaaggggag   9120
gaatatactg actttgccat attaccttat ttgcagcttc aggtaacata tttccctgca   9180
catttagagc tgtgtaaaga cactcctaga gaacaaactg taccatttgt ggagcaaaga   9240
tagcggtgga gagtgctctg tgaatgtgga tggtcaggcc tgtttttagc ctgatgaggt   9300
gagatgtaat atcaggtgac ctcacagcca gagtggcaag ccacctgatt catgagaagt   9360
gaagttgctc agttgtatgt gactctttgc actcccatgc aatgtagctt accaggctcc   9420
tttttcgatg gaattttcca ggcaagaagt actggtatgg cttgccactt cctttttccag  9480
gagatattcc tgacccaggg atcacacccg ggtcttcaat gttgcaggca gatgctttac   9540
cctctgggtc accagaatcc ggctggattc attgaaaatt cactgattta acaaaagctg   9600
tcctggaatg gaagagtaga atgagcctgt tgtatttctc tggcaggtgg tatgctgtaa   9660
ctacaaggct tcacaaggac gaatgctttg ggacatcagt ccccaattcc acgtgcacaa   9720
aatgacatct acctatagtt tcaaagctgt gtaaatccat tcctaggaca caatgggcta   9780
tccgtgaagg ttgacttttg catctgtttt tacactgatc agctaaaact gtactgtcag   9840
tggacttccc atcaggaagt ggtaagcaga atgtttctct cagaaaacac aagtccttga   9900
tgagacttgc ggccctaaag aagggaaaat gcccccgtgt gttttctgtc agtctggaga   9960
ctgcaattat tccaggttcc ttaggcacag attttgcttt catttcaggc cctgagttct  10020
aggttcagag aaacatttcc ccacagcttc agagctgtgc aaaacactcc tagaacacac  10080
tgtatcattc ccttagacaa gagaccaggg aagagcattc tgtgagcgct tctgcgatat  10140
```

-continued

```
cagttgttac cctgagtggg aagaattaca ctgtcaggtg acttggtagc attaataagc  10200
tagagtctgt gctttcagaa aaagcagaca cttttagcaa agttgccttc gtaaggaagt  10260
ggaaaatgaa cccgtgtgcc tttctttcag gcttaagact gcaatcaccc tgtggtcaaa  10320
aaagaaatac tgcttctgac attaggctaa aaagcccaca tgaaccaaac aaatgcccct  10380
gtcgttagaa agctgtgtaa gagacccaag gacagactgc accagtccat gagtaaagag  10440
ttctgggggg agtgttctct gggtgttgac tgccatacct gtagtcagca gcctaattcg  10500
gtgaaactgg actgggtgat gacttcccag taagaagtgg caagctacat gttccttttg  10560
gaagactcaa agaatggcca aaagctgttg tcataatgcc cagacaaacg agccagtgca  10620
tttcttgctg gttgaaggct gcaactatcc agctttcagc agaggaatat tctgattttg  10680
ccatattacc tggatttgca gcttcaagat aacacatttc cctgcacaag tagaggtgtg  10740
taaagacact cctagtgtac aaactctgta ccacctgggg aacaaagata gcgtggacag  10800
tgctctgtga atgtggatgg ccaggcctgt tttcaccctg aagaggtgaa aagtactgtc  10860
gggtgacctt gcagccagaa gcggcaagac gcctgcttca tgagaagtaa agttgttcag  10920
tcattgcgac tctttacaat cccgtggact gtagcttacc aggctcctcc atccatggaa  10980
ttttccaagc aagactactg gagtggcttg ccatttaatt ctcaatggat cttcctgatc  11040
caaggatcaa acccaggtca cccatgttgc aggcagatgc tttacccttt gagccaccag  11100
ggaagcctgc cagattcatt gaaaattcaa ctacttaact aaagctgttc tggaatggaa  11160
cagcagaatg agcctgttgt gtttttctgg caggtgagct gctgcaacca cacagtttcc  11220
caaggggaaa tgactgtttt gggatgtcag accccatttc caggtgcaca acaggacgtc  11280
tccctgaaga ttcaaagctg tgtaaacgca ttcctaggat acaatgtgct ctctgtgaat  11340
gttgactttt gtatctgttt ttctactgat tagctaaaac tgtactgcca agggacttcg  11400
catcaaaaag tggcaagcag acccatggtc ctaaagaaga gaaaaatgac cccatgaact  11460
tttccatcag gctggagatt gtaagtattc caagttcatt agtaacaaat gctgctttca  11520
tttcaggcca ccatttctag gttcagagaa acatttcccc gcagattcag agctgtgcaa  11580
agacactcct agaacacact gtatcattcc ctaagaaaag agttcaggga agagtgttct  11640
gtgagtactt ctgccatacc tgttgttacc ctgagtgggc tgaattacag tgtcaagtga  11700
ctacgtagca ttaaaaagca agggcgtgtt ctttttgaaa acacagatac gtaagtaaaa  11760
ctaccatcat aaggaagagg caaatgaatg caagtgcatc tctttcaggc ttaggactga  11820
aaccacgctg cagtcacacc aagtgctgct tctgccatta gtctctgaat cctacgtgag  11880
cataaaaaaa aaaaaaaaaa aatccctgtt gtgagaaagc tgtgtaagag accccaagga  11940
cagattgcat cattccatgg gtaaagagtt cagtgaggag tgttctggga ctgttgactg  12000
ccatacctgt tgtgagcagc ctaattttgg tgaaactgga ccagttgatg acttcccagt  12060
aagaagcggc aagctgcaca ttccttttgg aagactcaaa gaatggccga aagctgttgt  12120
cataatgccc agacaaatga gccattgtgt ttcttcttgg ctgtttggag gctgcaacta  12180
tacatctttc acaggaggaa tatactgact ttgccatatt acccagattt gcagcttcaa  12240
gataacacat ttccctgcac atttattgct gtgtaaagac acttctagtg tacaaattct  12300
gtgccgtttg tggagcaaag atagcagtgg agagtgctct gtgaatgtgg atggccaggc  12360
ctgttttcac cctgatgagg tgaaaaatac tgtcagatga ccttgaacca agaagtggca  12420
agccgcccgc ttcatgagaa gtgaagtttc tcagtcatgt ttgactcttt gcaatcccat  12480
ggactgtacc ttaacaggct cctcagtcca cggaattttc caggtaacag tactagagtg  12540
```

-continued

```
gcttgccatt tccttctcca gggcatcttc ctgacccagg ttttgaatgc gggtgttcca  12600
ctttgcaggc agccgtttta ccctctgagc caccaggaaa gcctgctggg gtttacagaa  12660
aattcaactt cttaaccaaa gctgttctgg aatgaaaaag tagaatgagc ctgctgtgtt  12720
tttctggcag gtgggatgct gaaaccacac aggttaccca aggggaaatg actgctttgg  12780
gacatcagac accaattcca ggtgcacaaa aagatgtctc cttgcagagt caaagctatg  12840
taaatgcatt cctaggacac aacgtgttct ccgtgaatgt tgacttttgc atcccttttt  12900
gcactgatcc tctaaaactg tactgtcaga ggaattccca tcaagaagtg gcaagcagac  12960
ttgtagtgct aaagaagggg aaaatgcccc cgagagcttt ctgtcaggct ggagattaca  13020
agtattccaa gttcattagt aacatatgct gctttcattt cagggcctga gttctaaggt  13080
tcagagaaac atttccccat agcttcagag ctgtgcaaag cgactcctat cacacactgt  13140
atcattgcct tagaaaagag ttagggaaga atgctatgtg agtgcctctg gcatacctgc  13200
tgtcaccctc atgggctgaa ttacactgtc aactgactat gtagcattaa tcagcaagtg  13260
cctgttcttt caccaaacgc agatatataa gctaagctgc ggtcatgagg aaaaggcaaa  13320
tgaacccatg agtgtttctt tcagggttaa aagtgcaagc accctgcagt cacacgaaga  13380
aatgctgtgt ctgcctttag gcaaaaaatc acaggtgaac ataaacaaat atccctgtcc  13440
ttagaaagca gtgtaagaca gcccagggac atattgcacc attccatgag taaagagttc  13500
agtgaggagt gttctgggat acctgttgtc agtagcctag tcggtgaaac tggactgggt  13560
gacgacttcc cagtaagaag tggcaagccg caggttcctt ttggaagact caaagaattt  13620
cccaaagctg ttttcataat gcccaggcaa atgagccagt gcgtttcttc atggctgatt  13680
gcaggctgca actatccagc tttcacagta gaaatatact gattttgcca tataacccag  13740
atttccagct tcaagagaac acatttccct gctcatttag tgctatgtaa agacacccct  13800
agtgtataaa ttctgtacca tttgcagagg aaagagcagt ggagaatgct ctgtggatgg  13860
ccaggcctgt ttttaccctg aagaggtgaa aagtactgtc aggtgacctc gaatcaagaa  13920
gtggcaagcc tcccgcttca tgagaagtga aggtgctcag tcgtgttggc tttatgcaat  13980
cccatggact gtagctgacc aggctcctct gtccatggaa tcttctaagc aagaagactg  14040
gagtgacttg tcatttcttt ctccagggaa tcttcccgac acaggatcga tccctggtct  14100
ccctcattgc aggcagacgc tttaccctct gagccaccag aggaacccgc cagattcact  14160
gaaaagtcaa ccacttactg aaagctgctc tagaatggaa gagcagaatg agcctgctgt  14220
gtatttctgg taggtgggat gctgcaacta caaaggttta ccaggggaaa tgactgcttt  14280
gggacattag tctccatttc caggtggaca ggacgatgtc tctgcacttt tcaaagctgc  14340
gtaaatgcat tcctaggaca caatgtgctc tccaagaatg ttgacttttg catctgtttt  14400
tgcactgatc agctaaatct gtaccgtcag aggacttccc atcaagaagt gacaagcaga  14460
ctttggtctt aaagtaggga aaaatgcccc tgtgagcttt tccggcagga tggagattgc  14520
aagtattcca ggttctttag gtgcaaatgc tgctttcatt tcaggcccca agttctaggt  14580
tcagagaaac ggtttgccca gcttcagagc tgtgcaaaga cactcctaga acacactgta  14640
tcattcactt agaaaagagt ataaggaata gtgttctgtg attcatctgc catacctatt  14700
gttaccctga gtgggccaaa atacactatc aggtgacttt gtaacattaa caggcaagca  14760
cctgtgcttt cagaaaatgc acatacttaa gcaaagctgt ggtcgtaaag aagaggcaat  14820
gaacccatgg atgtttcttt cagggttaag gttgtaacca ccctgcagtg acacaaagaa  14880
gtgctgcttc tgccattagg ctaaaaatcc ctggtgaacc aaacaaaagt ccccctgtca  14940
```

-continued

```
ttagacagct atgcgactga gtccaaggac agattgcacc attccatgtg taaagagttc  15000
agtggggagt gttctgggac tgttgactgc catacatgtt gtcagcagcc taattcagtg  15060
aaactggact ggatgatgac ttcccaatag gaagtggcaa gctgcatgtt cctttcagaa  15120
gactcaaata atggtacaaa gctgttgtca taatgctcaa atgagacagt gcatttcttc  15180
cttgctggtt agaggctaca atccaggttt cacaggaggt atatactgat tttggcatat  15240
tacccggatg tgcagcttca agataataca tttcccagca tttagagctg tgtaagacac  15300
cctagtatac aaactctgta ccatttgtgg agcaaagacg gtagtggaga gtgctctgtg  15360
catgtggatg gccaggcctg tttttaccct gatgaggtgg aaagtactgt tgggtgacct  15420
tgcagccaga agtggcaagc tgcctgcttc atgagaagtg aaattactca gtcgtgtggc  15480
tttctgcaat cccatggact gcaccttacc agactcctcc atccatggaa ttctccatgc  15540
aagagtactg gaatggcttg ccatttcctt ctccagaggg tcttcctgac ccagggatag  15600
aacccaagtc cccatgtgg caggcagaca ctttaccctc tgagccacta gggaagtgtg  15660
ccagattcag tgaaaactca actacttaac caaagatgtt ctggaatgga agagcagaat  15720
gagcctgttg tgtttttctg gcaggtggga tgctgcaacc acacaggttt ccccaagggg  15780
aaatgactac tttgggactt gagaccccaa ttccagttgc accagaagac atctccctgc  15840
agtttcaaag ctatgtaaat gcattcctag gacacagtgt actctccatg aatgttgact  15900
tttgtatctc tttttgcact gataagctaa aactgtactg ttagaaactt tccatcatga  15960
aagggtaagc caacttctgg tcctaaagaa aggaaatgtg cccccgtgag cttttctgtt  16020
aggctggaga aacaagtact ccatgtttgt taggcgcaaa tgctgctttc atttcaggcc  16080
ctgagttcta agttcagaga aacatttccc cacagcttca aagctctgca aagacactcc  16140
tagaacaaac agtatcattc acttaaacaa gagaccaggg aggagtgttc tgtgagtgct  16200
tctgccatac cagttgtttc cttgagtggg cagaattaca ctgtcacatg acttcgtagc  16260
aacaataggc aagaggctgt gctttcagaa aatgcagaca cggtctgcat tttagcaaag  16320
ctgtgatcct aaggaagaag caaatgaacc catgtgcatt tctttcaggc ttaaggctgc  16380
aaacaccctg cagtcacatg aagaagtgct gcttctgcca ttagactccg aaccccatgg  16440
gagcattaaa aaatgtccct gctgtgagaa agctgtgtaa gagaccccag gacacactgc  16500
accattccat ggaaaaagag ttcagtggga tatgttctca gagttcagtg tggagtgttc  16560
tgggactgtt aactgccata cctgttgtca gcagcctaat ttcataaaat tggactgggt  16620
gatgacttcc cagtaagaag tggaaagctg cacgttcctt tcggaagact caaagaatgg  16680
ccgaaagctg ttgtcataac gcccagacaa atgagccagt gcatttattc ctggctggtt  16740
ggaggctgca actattcagc tttcgcagga caaatatact gatttttcca ttttatctgg  16800
atttgcacct tcaagataac acattcccct gcacatttag tgctgtgtaa agacactcct  16860
aatgtacaaa ctctgtaccg atgtggagca aagacagtag tggacagtgc tctattaagg  16920
tggatggcca acctgttttt accatgatga ggtggaaagt actatctgat gacctcacag  16980
tcagaagtgg caagccgcct gtttcatgag aagtgaagtt tctcagtcgt gtgcaactct  17040
ttgcaatccc atggattgta gctaaccagg ctcctctgtc catggaattt tccaagtaga  17100
ctagagtggc ttgccatttc cttctccagg ggatcttcct gacccaggga tcgaacccgg  17160
gtctcccaca atgcagacag acactttacc ctctgaacca tgggtccatt gaaaattcag  17220
ctacttaacc aaagctgttc tggaatggaa gagtagaatg agcctgttgt ctttttctgg  17280
caggtgggat gctgcaacta cacaggtttc ccaaggggaa atgactgctt tgggacatca  17340
```

-continued

```
gatcccaatt ccaggtgcac aagacatttc cctgcagttt caaagctgtg caaatgcatc  17400
ctaggacaca atgtgctctc tgtaatgctg actttttat ctgctttttc actgatcagc  17460
taaaactgta ctatcggagg acttcccatc aagaaatggc aagtagcgtg tttctctcag  17520
aaaacataag tacttgatga gacttgtggt cctacagtgg gggaaaatgc ccccgagtgc  17580
ttttccatcc tgatggtgat tccaaatatt tcaggtttga tgggcacaaa cgctgctttc  17640
atttcaggcc ccgagttcta ggttcagaga aacgtttccc cacagcttca gatctgtgca  17700
aagacactct tagaacacac tgttaccatt cccttagaaa acagaccagg gaagagtgtt  17760
ctgtgagtgc ttctgccata ccagttgtta tcctgagtgg gcagaattac actgtcacgt  17820
gactttgtga cattaataag caagcgcctg tatttcagaa aatgcagaca ctttagcaaa  17880
gttgcctttg taaggaagag gcaaatgaac ccatgtgcgt ttctttcagg cttaagattg  17940
caaccaccct gcagtacacg aagaaatgct gcttctccct aggctccaaa tcccatgtga  18000
accaaatgtc cctgcaaata gggaaaaatc agtatgttcc tcctgggaaa gcaggagagt  18060
tgtagcctcc agccagccac gaaaacaccc cagggcattc cattgctcat tatgacaaca  18120
gctttggtca attatatgag tttgctgaga ggaacatgct acttgccact gcttactggg  18180
agttatcacc cagtccactc tcaaagaaat aggctaacca caggtatggc agtcagcagg  18240
cacagaaccc tccccactga actctcagaa ccctccccac tcaactctta actcttggaa  18300
tggtgcagtc tgtccctggg ctctgtgaca cagctctcta actacaggga cgtttgtctt  18360
cttaaaacgg gatttggagt ctaatagcag aagcagcatt tcttcgtgtg actgcagggt  18420
gcttgcggtc cttagcctga aagaaacaca catgagttca tttttctctt cctgaagacc  18480
ggagctttgc taaagtatct gcgttttctg aaaacatagg cacttgcata ttaatgctac  18540
aaagtcattg gacagggtcc tttggcccac tcagggtagc aagaggtatg gcagaagggc  18600
tcacagaaca ctcttccctg aactcttttc taagggaatg gtacagtgta ttctaggagt  18660
gtctttcccc agctctgaag ctgtgggaaa aacatcttac tgaacctaga actcggagcc  18720
tgaagagaaa gcaacctttt cccctaacaa aacttgaata cttgcagtct ccaacctgac  18780
agaacaccac actggtgcat ttccccccttc ttcatgacag caagtttcat caagtacttg  18840
tgttttctgg gagaatcacg cttcttgcct tttttttgtg ggaaagtcct ctgacagtac  18900
agttttaact gttcgggata aaaataggca gagaagtcaa cattcacgga tagtacattg  18960
tgtcctagga acggactcac tcagctttga aactgcaggg agacgtgtgt tttactacct  19020
gggattggct tagggcatca aacagcagtc atcttctgtg aaacctgtat cattgcagca  19080
accaacctgc cagcaaaccc acaggctcat tctattcttc agtcctagaa cagcgttggt  19140
taaggagctg agtttttagt gaatcaggcg ggcttcccgg tggctcaggg ggtagaacat  19200
ctgcctgcaa tgcgggacac ctgggtttga tccctgggtc gggaagttcc acccaccaga  19260
gaaggaaatg gcaacccatt tcagtactct tgcctggaag ctacagtcca tgggaaagag  19320
tcgaacacaa cttagcagct tcatatctca tgaatcaggc tgcttgccac ttcttgctgt  19380
gagctcatct gacagtacat ttcacctaat cagagtaaaa cagccttggc catccacatt  19440
cacagagccc tctccattta tatctttgct cagcacatgg tacagtgtat gtacactagg  19500
agtgttaaca tgggatttgg agcctaatgg cagaagcagc atttctttgt gtgactgcag  19560
gtggcttgca actccttgca tcaaggtcct ttccattgga atgtcaactc atctaggtaa  19620
caacactatg gcactcagca ctctcaaata ctctcccaca gattttcctc atgggcagtc  19680
ccagtatgac caaggaatct gttcactagt ctcagaaagt ggagggaaac atactggctg  19740
```

-continued

```
tgactctcaa aattagggcc tgtgtgcaaa tgtggtgttc tcacatcata aaatctagac  19800
agctgctgag agagagatgc ctgaaaatca ctctttttc gcctttcatg catcaaagca  19860
ctgtacgttt cccagcgttc tgtttgctga gagtaaccca ctacttgtga atccttgctt  19920
ggaggtaaca atttcccctc acctgtttca cagtacagaa ggaaagcata atcgctgctg  19980
cggccgctaa gtcgcttcag tcatgtctga ctgtgcaacc ccatagacgg cagcccacca  20040
ggctcctctg tccctgggat tctccaggca agaatattgg agtgggttgc cacttcttct  20100
ccaaagcata atcacaggga gaaacaagac aaaaacccca agttccaaca acttttctct  20160
gtaggaagga tccagtgatc ctaggtctgt cttgaaaatt cttggatact gcagggatac  20220
ctactgagtg tgaacctgga tattgcacct tgatgacaaa attagcattg tctcttggtt  20280
gactctagaa ggctggggtt tagcaactgc ctgaaaatct atccaatgtt gttttcgtac  20340
tttgacagca atagctttgg ttaaaaacat tgggatttct gaagcaagta ggcagcttat  20400
aagttcttgt gtcaaggtcc tttccaccag aatgtcaatg aatctaggta acaacagtat  20460
ggcactcagc actctcagtc actctcgcgc agactgtttc ttcatgggca gtcccaggat  20520
gacctaggaa tgtattcacc aggctcagaa agtgcagaga aacataccag ctgtgactgt  20580
ccaaattaca gcctttgtgc aaacgtggtc ttctcatatc atagaatcta gacagttgct  20640
aacaggtagg tgcctgaaaa acactcccct tttttgcctt tcattcatca aagaaacata  20700
ggtttcccaa cattctgttt gctgagaata acaacactac ttgcaaatct gtgcttggag  20760
gtcattttaa ctaacaatta cccctcacgt gtgtcacagt agggaaggac tgcctacgta  20820
cagggaaaaa caaacaagcc aaaaaactca agttccttac attgcctctg tagaaaagat  20880
ccagtgatcc taggtctgtc agggacacac actgcgtgtg aacctggata ctgaaccttg  20940
ctggcaaaat tagcattttc tctcttatgg ccctgaaatg gtgcagccta gcaactgcct  21000
gaaaatccat acaatttttt cccctacttt tgacaccaat agctttggtc aaaaattggg  21060
atttctgaag caagcagggg gcttgcaact ccttgcgtca aggtcctttc ctttgggata  21120
tcagctaatc taggtaacag tggtatggca ctcagcactc tcagatactc tcgcacagac  21180
tgtttcctca gggatgtcac aatatgacct aggcatgtgt tcacaaggct cagaaagggc  21240
agggaaataa actggctgtg actctcgaaa ttacatcagg agggatgctg caactgcaca  21300
gggttcccag ggggaaacga ctgctctggg gcatcagatc ccaattccag gtgcacaaga  21360
agacgtctcc ctgcagtttc aaggctgtgt aaatgcattc ctaggacaca gtgtgctctt  21420
cgtgaatggt gacttttata cgtttttgca ctgatcagct aaaactgtac tatcagagga  21480
cttcccatca agaagtagca agcagtgtgt ttctctcaga aaacacaagt acttgatgag  21540
acttgcggtc ctacagcagg gaaaattgct cctgtgtgtt tttccatcag gctggagatt  21600
gcaagtattc caggttcatt aggcgcaaaa tgctgctttc atttcagacc ccgagttcta  21660
ggttcaaaga aacatttccc cacagcttca gagctgggca aagatacccc tagaacacac  21720
tgtatcattc tcttaggaaa gagaccaggg aagagtgttc tgtgagttct tctgccatac  21780
ctgttgttac cctgagtggg cagaattaca ctgtcgggtg atttgaggca ttaataagca  21840
agtgcctgtg ttttcagaaa acgcagacac tttagcaaag ttgccattgt aaggaaaagg  21900
caaatgaacc catgtggttt tccttcaggc ttaagactgc acccaccctg cagtgacgga  21960
agtgctactt ctgccattag gctccaaacc ccatgtgaac ataaacaaat gtccctgtca  22020
ttataaagct gtgtaagaga actcaaggac agactgcatc atttcatgag taaagagttc  22080
agaagggaat gttctgggag tgttgactgc catacctgtt gtcagcagcc taatttggtg  22140
```

-continued

```
aaactggact gggtgatggc ttcccagtaa gaagtggcaa gttgcatgtt ccttttggaa  22200
gaattaagta atgaaccaat gctgttgttt taatgcccag acaaatgagc cagtgcgttt  22260
cttcctgtct ggttggaagc tgcaattatc cagctttcac aggaggaata tactgatttt  22320
gccgtattat ctggatttgc ggcttcaaga taacacattt ccctgcacat ttacagctgt  22380
gtaaagacac tcctagtgta cacactctac catttgtgga gcaaagacag cagtggagag  22440
tgctctgtga atgtggatgg ttaggcctgt ctttaccatg atgaggtgaa aagtcctgtc  22500
aggtgacttc acagccagaa gtagcaagca gcctgcttca tgagaattaa cgttgctcag  22560
tcgtgtgcaa ctctttgcaa tcccatggac tgtagcttac cggctcctcc atccacggaa  22620
ttttcctggc aagagtactg aagtggcttt ccatttccta ctccagggga tcttcccgac  22680
ttggggatca aacctgggtc tcccaggttg caggcagatg ttttttcctc tgagccacca  22740
gggaagccag ccagattcat tgaaaattca actacttagc caaagatttc tggaatggaa  22800
gatagactga gcctgttgtc ctttttgggc aggtgggatg ctggaactac gcaggtttcc  22860
catggggaaa ttacttcttt gggacatcag accccaactc caggtgcaca aaaagatgtc  22920
tccctgcagt ttcaaagttg tgtaaatgca tcctaggaca caatgtgcta tccttgaatg  22980
ttgactttca tatctgtttt tgcactgatc agctaaaact gtactgtcag aggacttccc  23040
atcaaaaagt ggtaagcagc atgtttcttc agaaaacaca agtacttgag gagccttgtg  23100
gtcctgatga agcaaaaaaa tgtccccgtg tgcttttcta tcaggctgga gattgcaagt  23160
atttcaggtt cgctaggtgc aaatgctgct ttcatttcag cccccaagtt ctaggttcag  23220
agaattgttt ccccacagct tcagagctgt gcaaagacac tcctaggaca gacacactgt  23280
atcatttcct tagaagagtt cagggaagtg tgttctgtaa gtgcttctgc catacccttt  23340
ttttaccctg agtgggcaga attacactgt ctggtgactt gttaacatta gtaagcaagc  23400
accttgcctt cagaaaacac agatacttaa gcagaactgt ggtcataagg aagaggcaaa  23460
tgaacccatg tgcatttctt tcaggcttaa gattgcaacc accctgcagt gacacgaagt  23520
gctgcttctg ccattaggct cagaacccta agtaaacata aacaaatgtc cctgtcctta  23580
gaaagctaat gttggtccag tggtttgtgt aagctttgta taggctgaga cttatgctga  23640
gtttttgttt gtttttcctc tgatgggcaa ggctgagtga ttgggtttgt acttttgttt  23700
tgtttgttgt ttagatgagg agtcctgcac agggtgctac tggtggtctg gtgatgccag  23760
ggcttgtatt caagtggttt cctttgtgtg agttcacact atttgatact ctctaggatt  23820
agttctctgg ttgtctaggg tcttggagtt agtgctccca ctccaaacgc ttagggattg  23880
atctctctcc aaagaccagc ttaggtccaa actaccaaga ggaatttcac ttgaaatgaa  23940
agggccttta ctttaccaag aggaatttca cttgaaatga aagggccttt actttaccaa  24000
gaggaattca ctcgaaatga aagggactta ctgaattcca aaagccagag cacaagaaca  24060
catggagatc tctacccaga ggaaactcta ccatgccttg gttgcagcag atgttggtcc  24120
tcttctgctt tgatctgtcc ccgctttctg tggcagctgc ccagcagagg ccatctgacg  24180
tcattttgtt cattacctgg atgaaggggt gtctccttct cagaggagcc tgagacaaac  24240
aaagggacag tgcagagcca tccccgcacg gaagcccccct tccatttaga aatgtttctc  24300
ttaagctatg ttaatgaact atgtatttag cctagactct gtgtttcttc acttaggttc  24360
tgcctaagac tcagaactga taatggctca acaaaccagt atgtttttct catacaattg  24420
ttctcctaat ctatgttaat gagactatgt atttgcttgg aaacctgcct tcttcaaaat  24480
tcatgtcaat cattttatgg cctgggatga ctcaccttgt tccaatgtta cctcaaaatg  24540
```

-continued

```
catgttgtgg gtgaggggcc ctggtgccac tctctgagtt ttgagacatt tcctttcttt  24600
aattagtacc cttctgatag gtgtataagt taccattaaa gtctagcagg gggggcactc  24660
tttctgcccc ttctaatgtc tatgttagaa gcttaatctc ttttatactt taataaaact  24720
ttatcacaca aaagcttgga gtgatcaagt ctcataactg gccccagatt gaattcttct  24780
cctccaaagg ccaataatcc catcatcttt catggctcag caacaacctt tcaccggggg  24840
agctcatctg ggattcttca ggacaaggta aggacacttg gagctctagt tctttgttct  24900
cctggcaaac acattttctg ctgtacttta ctaactctat ggtgtgcttg tgtgtgtgat  24960
tgaaagatgc acacatgtgt gaagcaagat ctgggtccaa atctttggtt ctgtggtgac  25020
ctcataccac ttatggcagg aaccctgttg ggggattata ctgacctgct aatgtcaaga  25080
ggcacccaat gtctcctcca gggaaacaga ccaaggtgga taaaacgtgt ggatggaact  25140
ctcctttttt ggccaaactt tctggtctct ttgaccattt cataacttcc tgggaattag  25200
aactactaac ctaatcagtg ggatcataga ctttcaaggg acttgttatc tatgctgtta  25260
ctgtgtattg tcacttaggt tccaaacttt gttttgtttt tttttgtatt cacaaattgc  25320
ctagcctcac taggagtcaa tagtttggaa gctagatgga gttctaattc caagaacatc  25380
tctcaggttt aagattactc aggaaataca gcagtcttct tcctttggta acactagctc  25440
ttagtggacc agaggaggat ctccagttgc ttctgtctca acaccttaga tattcttcct  25500
gtggaatctg tgggaatgaa ctggaaggac tggccataat aacttgagga caaaaaatcac  25560
tttttcctca gtggccagcc cctcaccgtc tcttttgcta tcgcttatat tggtgtggtg  25620
agactcagaa ggaacatctt ggttttatgt ttgtccttta tgatttactg gtcttactgt  25680
ggtcaggaat gtactcaggg ttgtgcatag gcactcagga gacaaatatt tcccttagtg  25740
gtcttagctt gggaggcatt ctggaaggtt actctgactg cacctcgggt ggcatcagag  25800
gcaagcaaaa gttttaatgg tgaggaactg ggtattagtc tgggatgcca tcaggtctac  25860
ccctgatgca tctccacccc accgcagtgg tagaatgggg aggggcagta gtggaatacc  25920
tgtggtaaga gacaggttaa ctccagccag ggaaggaagc ttaggtggaa gacctgtctc  25980
cacccccatc tagaacaggg agggacagta gaaggacagt gctggtagct gtttttctct  26040
cttaaaggtg ggagctaacc attccagcct cactcctttg aaaaactggg atagatttga  26100
tccccagagc ctaatgaaga catgcctgat cttcctatgt gatactacat ggccacagta  26160
tccattggag gatagcgaat ggtggctggt tggagggtct cttaattaca atattgtttt  26220
acaattaaac tggttctgta gataacaagg aaatgggtag aagtagcata tgtgttgccc  26280
tttttctctc tgtgagacat atcagattta tgtcctaagg gtatatatta gggtatgaaa  26340
ttttcagctc cctattctgc tatatgacct tatttgggag gatgtgatgt atatcctggg  26400
acaggcgcta actcctgcat caacaacttg agtttggaaa gctgttgcct atggagatga  26460
atggcttggc aaggaatcat tagggaagag ggaggatgag atagctgccc tccccactgg  26520
ggatcaggca gtcccaacta tagaaccaga ttgggactaa aaggctaaag gatgatggga  26580
taagagtcat ttgtcagatg tgttcttgaa ggactcagac aagctcatgc taagacttta  26640
aatgatgcta atttggcaaa catagaacag gaagagaacg aagcttctgg taaattccta  26700
gatagactga gggaagccct ttgcagattc actgagattg atcctagtca gctccagata  26760
tccactaaaa cacatgtatg gaccaaatca gtctttagat aatctgttgc aattggctca  26820
gtcagtctat tatggcaggg agtatgaggg aagaaagaaa ggcagagaaa gaccaaggta  26880
ctggctgaag cccttgtaat ggctgtcagg actgttctta aacagcctga gaaaaattcc  26940
```

-continued

```
aggagagacc caggtgaaag gggatgggct tgctatttct gtggaaagga ggagcgcctc  27000
aagcgggatt gccctcaggc atctaagggg tccccagctc catgtttgcc tgtaaggggc  27060
cacactggag gagagactgc ccccagacgc gtaggtccca gtggtgggat tctcaagaca  27120
accaggactg aatgtgccca ggggtcccca cacaaactcc caccctaatt acagctgagg  27180
aaccccaggt attagtaact gtgggtggcc aatctgtcaa tttccttgtg gacaccaggg  27240
caagttactc tgtgcttact gaagcccctg gtccactttc tccccaatcc gcttctataa  27300
tgggactgtc tggacaagcc aaacattaat attttggtca tcctctaagc tgtcaactgg  27360
gactctgttt ttacagagtg ccagattgtg ccagagtctc cctcacccct tttagggagg  27420
gatatactga gcaaggtcca tgcctctgtt tcatgaatat ggagcccttc ctttctctcc  27480
ctttaattga acaaaatgta aatcctaaag tgtgagctga tggaaaatct gtgggtcgaa  27540
cacaaaatgc tattcctgta gttgtgaagc tcaaaaaccc actcatactt ccccatcaaa  27600
agcagtatcc actgaaaccc gaggttaaag aagggttaaa acccatcatc gagattttaa  27660
aggagcaggg gctattaatt ccctataaca gtccatgcaa cactcctatt ttgggtataa  27720
agaagtcaaa ttataagtgg agactagttc aagatttaca aataataaat gaggctgtac  27780
atcctttaca ccccatggtg cctaatcctt atactctatt gtataaaatt actgaacaag  27840
agaaatattt ttcagcatgc tttctagagt taaacctata ctatgtcatc ccctacctat  27900
gactttcaga caattgagag gatttggggg aatcataggc tactgcctca tttggattct  27960
gggttatggg gaacttgcct ggcctatata tgaacttaca actgaaactc aacaagccca  28020
aactgacaaa ctggttcagt ctctagatac tcaaaaggct tttaaagctc ttcagattgc  28080
tctcctgcca gctcctgctt taagcttgcc cacagggtca gaatttaatt tgtttgtcac  28140
tgaaagaaaa ggtatggtct tgggagtttt gacacaaccc cgagggcctc atcagctata  28200
tataggatac ctgaaaaact taaatcctgc cactttcctt cctgacaagg aaaatgaaac  28260
acctgatagc aattgttccc aatttctaac tttaaactat tcagctcggg aagacctgat  28320
ggataccccca ttagacaatc ctgatatgga attatttaca gatggcagtt cttttgttcg  28380
ggatgggaaa cttaaagcag gttacactat aatgcgactg gacagatttt aaaagcaaag  28440
tctctcccca gggaatgagc gctcaggtag tggagcttgt ggctctgacc cgagctctag  28500
agttaatcaa agggcagcaa gtcaatatct acagtgattc taagtatgct tatttgactt  28560
tacatgttca tgctgtgata cggaaagaaa gacagtttaa aacggcaaca ggagaaccta  28620
ttaagcattt caaaagactg agggactttt aactgctata aattgtccta cagaagtagc  28680
tgttgtgcac tgcaaaggac acagtaggga tgggaataag tagctgaggg taatcagctg  28740
gctgactgtc aagccagaaa accagcagtt taagaaaccc cttcactgca gatgcctttg  28800
aactagacag gtcctgtgga ataggaaaaa catcacaatg aggaagaatt agaaagatat  28860
gagaaagtag gagcaaacat tatcgataaa ggatgcttat agtccaagga tggatgatga  28920
ataattactg aaaattctca atggaaaatt cttaagagtt tacaccagag ttttcattta  28980
ggtgttgaga gcacttacca gatggcttct catttctttg aaggaaaaat gtaatggaaa  29040
ctttagagaa cattatcaaa aactgtgaga tttgtcagaa aaataaccca aagactgaaa  29100
agttagcaaa atctgggtta caatgaagtg gaaaatatcc tggagaggac tgggaaattg  29160
attttactca tatgccaaag gcaaatggat attcttgatt acaagtttgg gtggatatat  29220
ttactggaca gattgaggct tttccctgtc atagtgaaca gcctaagcag gttataagaa  29280
ttttaatcca tgaaattact cccaggcttg ggctgctgtg gagccttcag agtgacaatg  29340
```

-continued

```
gctttgcctt taaagccact gtaactcagg ggatgtcaaa agctctagga atagacgatc  29400
acttacacgg ctcctggaga ccccgatcct caggaaaggt tgaaaaagct aatgacatta  29460
ttaagagaca tctgtgcaaa ttaactcaag agaggcatga cagttggtgt aaagttctac  29520
acatagcttt aatgagggct cgaattgccc cccaaaatga gggactgtcc ccctttgagt  29580
gcatttatgg aagacccttc ttacccacag acattgttat agaccttgaa gccttggaat  29640
tatctaactg tgtaactcag cactcagctt ttcaacaggc attaaaggaa ctctgatgtg  29700
actcatgacc cagactctaa gtcaagaaag acactgtctg agccaggaac tgaggtcctg  29760
ataaaaatat tgggatctcg ggggcaatcc ctggagcccc tctgggaagg cctttaccag  29820
gttattctat cttttcccat agctgtcaaa gtgccagata ttgatcattt tacaccacac  29880
ttaagagttg gcatcctgac cagaactaaa tgatgtcact ttatgtcttt attctctaca  29940
ctcttacttt gtacttttca gatcagcctg ataatctatg tgagcttgct tctgctgact  30000
ccaaaaatcc agtgtctgcc gtttgaccct caagacaatg ccctcctgtc ctgggatcac  30060
tcctatgctg catttcacat tcagtctaat tactgggtct gtggagcact cccttcttca  30120
tcagtggaag gcttccgtgg tgggcatctc cacttgaagg aaaggagttt cttcaagtct  30180
gcaaatcttt ctacaaagac aataatatgt gatgcctctt cttaatatga taacatctaa  30240
caatcctaag atggactggt gcaacacttt gtaccttaac tatgggcact atgagacttt  30300
taactttgct gattgttctg tttttgctgt ttgctccctg catctgtaag agtgtggctg  30360
gatttgtttc tagctgcatg aaggatttta agtgacaaat ggttgctcaa actcctgcca  30420
ctgtggcagc ttcctccaac tacctacttg ggcccctgg atcagagacc ctcaatatga  30480
gggttaggag agtatgttgc ctcaccaatt tagggacgat gccccttatc agcttggaag  30540
cagttacaga atgaaaacaa tgccccttc cctaggaaac ataattctcc taaaagaaaa  30600
gggagaaata agacggtaac aggcaggaag gctcagttca gttcagttca gtcactcagt  30660
cgtgtctgac tctttgcgac cccatgaatt gcagcatgcc aggcctccct gtccaccacc  30720
aactcccaga gttcactcaa actcatgttc ttcgagtcgg tgatgccatc cagccatctc  30780
atcctctgtc gtccccttct cctcctgccc ccaatccctt ccagcatcag agtcttttcc  30840
aatgagtcaa cccttcacgt gaggtggcca aactattgga gtttcaactt cagcatcagt  30900
ccttccaatg aacacccagg accaatctcc tttagaatgg actggttgga tctccttgca  30960
gtccacagga ctctcaagag tcataggttg caaatgtcag acatttttca tctctctctc  31020
aagtggcagg aggaaacaaa ctgcaagtgt cagatttctt ttcccttctc tatacaaaat  31080
taaaagatgc tttcttttaa aattctgtgt tgccatgaca cctggttcca cctgaactta  31140
acttttctca aatcttgagc caaccaatgc atttttctta tggaaatgtt tttcttaagc  31200
tatgttaatg actatgtatt taacccctag actccgtgtt tcttcaagtc ggtttcacct  31260
aagactcaga accgataatg actcaacaaa ccagtatgtt ttactcatac agttgttctc  31320
ttaatctatg ttaatgagac tgtgtatttg attggaaacc tgcctttctt catgccaatc  31380
gtcttatggc ccaggaagat tcaccttgtg ccaatgttat ctcaaaatgc atgttgtggc  31440
tgagtggcct gcagccactc tctgaatttt gatacatttc ctttctctaa ttagtagcct  31500
gctgatatgt atataactta ctgctgaaga ctagcagggg ggcactcttc ctgcccccctt  31560
ctcttttcct ctggaggcca agaactctgg tgtctttcat tgctcagcaa caacctttca  31620
ataggaggat actgatattt ctccaagaaa agctatagtt ttgactatac agacctttgt  31680
tggcaaagtg atgtctctgc tttttaatat gctgtctagg tttgtcatag ctttcttccc  31740
```

-continued

```
aaggaacatc ttttttttta atttaatgac tgcattttta atgttgttat gctttggtcc  31800
agctgttgca ttctttctga agctattagt aattaccctc tgctctttat cagtagctta  31860
ttcgacactt tctgacctga ggggctcatc ttccagtgtc atctattttt gccttttcat  31920
aacatttatg ggtttgggc agcaagaata ctggaggaaa ttcccatttc ctccttcagt  31980
ggaccatgtt ttcccagaat acttcaaatg acctgtccat ttttggtggc cctgcatggc  32040
atggctaata gcttaattga gttatgcgag acccattgcc gcgacagtgc tgtgatccat  32100
gaagagacag gaagctctta gaattacttt ctttttaatg cattctattt attcccctca  32160
gctagattct aagtgtaatt tgtctgttta ttcattgata catttaacag atgtagaaga  32220
gttccttttg tttctaaaat attcaaaata tttctttata tataaaggat attcatgatt  32280
ttgtaataat tttcacaaac tgacataata attttactgt tcagttcagt tcagttcagt  32340
cgctcagtcg tgtccgactc tttgcgaccc catgaatcgc agcacgccag gcctccctgt  32400
ccatcaccaa ctgccggagt tcacccagac tcacatccat tgagtcagtg atgtcatcca  32460
gccatctcat cctctatcat ccccttctcc tcctgccgcc aatccttccc agcatcagag  32520
tcttttacaa tcagtcaact cttctcatga ggtggccaaa gtattggagt ttcagcttta  32580
gcatcattcc ttccaaagaa atcccagggc tgatctcctt cagaatggac tggttggatc  32640
tccttgtagt ccaagggact ctcaagagtc ttctccaaca ccacagttca aaagcatcaa  32700
ttcttcggag ttcagctttc ttcacagtcc aactctcaca tccatacatg accactggaa  32760
aaaccatagc cttgactaga cggatctttg ttggcaaagt aatgtctcta cttttcaata  32820
tggtatctag gttggtcata actttttact gtagactact tttttttttt tgagatggca  32880
agaatacaca gaagaactgt acaaaaaaga tcttcacgac ccagataatc atgatggtgt  32940
gatcactcac ctagagccag acatcctgga atgtgaagtc aagtgggcct tagaaagcat  33000
cactacgaac aaagctagtg gaggtgatgg aattccagtt gagctattcc aaatcctgaa  33060
agatgatgct gtgaaagtgc tgcactcaat atgccagcaa atttggaaaa ctcagcagtc  33120
ccacaggact ggaaaatgtc agttttcatt ccaatctcaa agaaaggcaa tgccaaagaa  33180
tgctcaaact accgcacaat tgcactcatc tcacacgcta gtaagtaatg ctcaaaattc  33240
tccaagccag gcttcagcaa tatgtgaact gtgaacttcc tgatgttcaa ggtggtttta  33300
gaaaaggcag aggaaccaga gatcaaattg ccaacatctg ctggatcatg gaaaaagcaa  33360
aagagttcca gaaaagcatc tatttctact ttattgacta tgccaaggcc tttgactgtg  33420
tggatcacaa taaactgtgg aaaattctga aagagatggg aataccagac cacctgatct  33480
gcctcttgag aaatttatat gcaggtcagg aagcaacagt tagaactgga catggaacaa  33540
cagactggtt ccaaatagga aaaggagtat gtcaaggctg tatattgtca ccctgcttat  33600
ttaacttata tgcagagtac atcatgagaa acgctggact ggaagaaaca caagctggaa  33660
tcaagattgc caggagaaat atcaataacc tcagatattc agatgacacc acccttatgg  33720
cagaaagtga agaggaacta aaaagcctct tgaggaaagt gaaagtggag agtaaacaag  33780
ttggcttaaa gctcaacatt cagaaaacga agatcatggc atctggtccc accacttcat  33840
gggaaataga tggggaaaca gtggaaacag tgtcagactt tatttttctg ggctccaaaa  33900
tcactacaga tggtgactgc agccatgaag ttaaaagacg cttgctcctt ggatggaaag  33960
ttatgaccaa cctagatagc atattcaaaa cagagacgtt actttgccaa caaaagttcg  34020
tctagtcaag gctatggttt tcctgtggtc atgtatggat gtgagagttg gactgtgaag  34080
aaggctgagc gctgaagaat tgatgctttt gaactgtggt gttggagaag actcttgaga  34140
```

-continued

```
gtcccttgga ctacaaggag atccaaccag tccatcctga aggacatcag ccctgggatt  34200
tctttggaag gaatgatgct aaagctgaaa ctccagtact ttggccacct catgtgaaga  34260
gttgactcat tggaaaagac tctgatgctg ggagggattg ggggcaggag gagaagggga  34320
cgacagagga tgagatggct ggatggcatc actgacttga tggatgtgag tctgagtgaa  34380
ctccgggagt tggtgatgga cagggaggcc tggcgtgctg tgattcatgg ggtcgcaaag  34440
agtcggacgt gactgagaga ctgatctttt tttttgtaga ctacttttaa ttcaaagaaa  34500
tgtccgtcaa ttattttctt atgatcacct caactttgta tctatggtaa gcacagaaaa  34560
gttcaaaact ttacctcagc atttcctatt atatttcttc cttgtgtata agtcaataat  34620
atgtgattct agccaaatgc acaaactgtt cagtcatcaa agcacttact aggtgcctga  34680
tactgcagta ggcatgatgg gaagcaacat acatgcatca cagagggaca tgctaaatat  34740
tgttgatata cattaaagga atagttaggg aaaatatcga tataaaggaa atggtaaatc  34800
tgatggagtt tatagaggat tgtgtattgt caaatacaga tgtcaatttc tataagttta  34860
acatataaaa atggagaaca aagggctaca atgagaagat ataaacatta aaatcatcta  34920
gcaaatgtta tctcacaatt aaaaaatacc ttctgtgcac taaagcacta aacttatttt  34980
tcttaaagcc cttgaaatta aaggctataa accagttctt tcaaagggta aacaaaattg  35040
ataaacttta agccagactc atcaagaaaa aaaaagagat ggaaaagaac ccaatgaata  35100
aaatcagaat tgaaaaagga gaaggtacaa cagatataac agaaaccagt ggactatacc  35160
ccaatcaaat gaaaacccta gaagaaatgg acaaattctt agaaatatac aatctccaaa  35220
gactaaacca gtcagaaata gaaaatatga acagaccaat taccagtaat gaaattaatc  35280
agtaatttta acactcccca aaaaataaaa gtccaggaca agacggcttc acaggtgaat  35340
tctatcaatt taacaaacag ttagcaccta tatttctgaa accatttcaa aaaattacag  35400
tgagagaaac acttccaaac acaatctaaa tgccaccatc accttgatat taaaatcaga  35460
aatatgccac aaaaacaaat aaaattacag tccagtaaca ctgatgacag agaaggcaat  35520
ggcaccccac tccagtactc ttgcctggaa aatcccgtgg atggaggagc ctggtaggct  35580
gtagtccatg gggtcgctaa gagtccgaca cgactgagcg acttcacctt catttttcac  35640
tttcctgcat tggagaagga aacggcaacc cactccagtg ttcttgcctg gagaatccca  35700
gggacggggg accctggtgg gctgctgtct atggggtcgc acaagtcgga cacgactgaa  35760
gtgacttagc agcagcaaca ctgatgaaca tatacacaga aaccaccaca aaatacttgc  35820
aaaccaaatc caacaataca ttaaaaacac cagacaccat ggtgaagtgg gatttatatt  35880
agggatgcaa ggatttttta atatctacaa atcaatcatt agaaaatttg aaaaatgaaa  35940
gcaacctgat tatctcaata ggtgagataa aaaaaaaagg ttttaaaaaa ttcaatcccc  36000
acttatgatt aaaaaaaaaa ccaataaaag gacatgtggg gaacctacct aaatatgata  36060
aggatcatat acaacaaact cacagcaaaa atcattctca atgctgaaaa ttaaaaggca  36120
tttcctctga gatcaggaaa aagacaatga tgttcattct caccattttt atttagcata  36180
gtttgggaaa ttctagtcat gggaatcaga gaaaaaaatt aacaaaaaga atgcaaatta  36240
aaaaagagta agtatggact ctgttgcaga gggagagggt gggaagattt gggagaatgg  36300
cattgaaaca tgtataatat catgtatgaa acgagttgcc agtccagatt cgatgcatga  36360
tactggatgc ttggggctag tgcactggga cgacccagag ggatggtatg gggagggagg  36420
agggaggagg gttcaggatg gggaacacat gtatacctgt ggcagattca ttttgatatt  36480
tggcaaaact aatacaattt gtaaagttta aagataaaaa aattaaaaaa agagtaagta  36540
```

-continued

```
aaacaatcac tgtttgtaga tgacatgata ctatacatgt gtgtgtacta ggtcacttca  36600
gttatgtttg actctttttg atcctatgga ctgtatccca acagtctccc ctgttcatgg  36660
gattctccaa gcaagaacac tggagtgggc tgctgaaacc ttctgcaagg gatggtcatg  36720
atctagggac tgaactcgcc tctcttacat ctcctgcatt ggcaggcagg ttctttacca  36780
ctagcgccac ctgggaagac aaatactata catacaaaat actaaagaca attccagaaa  36840
actaaaacag ctaatcaatg aattcagtga ggtttcagga tatggaatta atacacagat  36900
ttcccttgta ttctgataca tgaaaagtaa aagatccata aaaaattaag gtaacaattc  36960
cacttaccat catatcaaaa agaataaaac acctaggaat aaacttacct aatgaggcaa  37020
aagacctata ctcagaaaac gataagatac tgataaaaga aatcaaagat gatacagatg  37080
gagaaatata acaagttttt gagttggaag aatcaatgct gttaaaatga ctgtactacc  37140
caaagcaatc tacagattca atgccatccc tgtcaaatca ccagtgacat ttatcccaca  37200
attagaacaa aatatttttt acactttgta ttgaaacaca aaagaaccca aagagccaca  37260
ccaatcttgt gagagaaaaa aaggagctga aggaatcaag cttcctgacg tcaaattatg  37320
ctacaaaaga agagtcatca aaactatatg atactggcac aaaaacagac atatagatca  37380
atgacacagg atgagacccc ataaataaac ccacattctt acggccaatt aacctatgac  37440
aaagaaggca agaatataca atgaagaaaa gacactattt gcaataagtt gtgctggaac  37500
aaattgacaa ctatatgcaa aagaaaaaat tagaatattc tctaacatca tgtataaaaa  37560
taaagtcaaa atgggtcaaa tacctaagta taaggctaga tacttgaaaa atcttagagt  37620
aaaacacagg tagaacataa attgcagcaa tatctatatt tagatatgta tcctggagaa  37680
atgaaaataa gaaaaacagg caaacgggac caaatgaaac ttaaaatcat ttgcaaagca  37740
aaggaagcca taaacaaagt gaaaagacaa accagagaat gttagaaaat atttgtaaat  37800
caaatgattg ataagagatt aatttccaac atatacaaag ggcacatgta gctcaacaga  37860
aaacaaaaca acacaatcaa aaacagacta ttcagttcag ttcagttcag tcgctcagtc  37920
atgtctgact ctgcaacccc atgaaccaca gcacaccaga cttccctgtc catcaccaac  37980
tcccggagtt tacccaaact catgtccatt gagtcagtga tgccatccaa ccatctcatc  38040
ctctgttgtc cccttctcct cctgccctca atctttccca gcatcagggt cttttcaaat  38100
gagtcagccc ttccgcataa agtagccaaa gtattggagt ttcagcttca acatcagtcc  38160
ttccaatgaa cacccagaac tgatttcctt caggatggac tggttggatc tgcttgtagt  38220
ccaagggact ctcaagagtc ttctccaaca ccacagtgca aaagcatcaa ttctttggtg  38280
ctcagctttc tttatagtcc aactctcaca tccatacatg actactggaa aaaccatagc  38340
cttgactaga tggacctttg ttgacatagt aatacctctg ctttttaata tgctgcctag  38400
gttggtcata actttccttc caagaagtaa gagtctttta atttcatggc tgcagtcaca  38460
tctgcagtga ttttggagcc caaagaaata aagtctctca ctgttttcat tgtttcccca  38520
tctatttgcc atgaagtgat aggaccggat gccatgatct tagttttctg aatgttgaac  38580
tttaagccaa ccttttcact ttcctctttc actttcatca agaggctctt tagttcttct  38640
tcattttctg ccataagggt ggtatcatct gcatatatga ggttactgat ttttctccca  38700
gcaatcttga ttccagcttg tgcttcttcc agcccagtga agaatagcaa ggagcgataa  38760
agccttcctc agtgatcaat gcaaagaaac acaggaaaac aatggaatgg gaaagactag  38820
agatctcttc aagaaaatta gagataccaa gggaacattt cagacaaaga tgggctcaat  38880
aaaggacaga aatggtatgg gcctaacaga agcagaagat attaagaaaa ggtggtaaga  38940
```

-continued

```
atacatagaa gaactgtaca aaaaagatct tcatgaccca gataatcacg gtggtgtgat  39000
cacccaccta gagccagaca tcctggaatg tgaagtcaag tgggccttag gaagcatcac  39060
taccaacaaa gctagtggag gtgaaggaat tccagttgag ctatttcaaa ttctaaaaga  39120
tgatgctgtg aaagtgctgc actcaatatg ccagcaaatt gggaaaactc agcagtggcc  39180
acaggactgg aaaaggtcag tttgcattcc aatcccaaag aaaggaaatg ccaaagaatg  39240
ctcaaactac cacacgattg cactcatctc acacgctagt aaagtaatgc tcaaaattct  39300
ccaagccagg cttcagcaat atgtgaactg tgaacttcct gatgttcaag ctggttttag  39360
aaaaggcaga ggaaccagag atcaaattac caacatccgc tggatcatgg aaaaagcaag  39420
agagttccag aaaaacatcc atttctggtt tattgactat gccaaagcct ttgactgtgt  39480
ggatcacaat aaactgtgga aaattctgaa agacatggga ataccagacc acctgatctg  39540
cctcttgaga aacctgtatg caggtcagga agcaacagtt agaactggac atggaacaac  39600
agactggttc caaataggaa aaggagtacg tcaaggctgt atattgtcac cctgcttatt  39660
taacttatat gcagagtaca tcatgagaaa tgctgggctg gaggaagcac aagctggaat  39720
caagattgcc gggagaaata tcacctcaga tatgcagatg acaccactct tatggcagaa  39780
agtgaagagg aactaaagag cctcttgatg aaagtgaaag aggatatggc atcaccgact  39840
caacagacat gaggttgtgc aagctccgag agttggttat ggacagggaa gcctggcttg  39900
ctgctgtcca tggggttgca aagagttgac catgactgag cgactgaact gaactgatta  39960
attagtgata ttcagtatct ttacatatct ttagtggcca tctgtgtatc ttcttttgag  40020
gaatgtttat ttagatcatc agtccatttt tggcattgcc tttctttggg attggaatga  40080
aactgacctt ttccagtcct gtggccactg ctgagtttta caaatttgct ggcatattga  40140
gtgcagcact ttcacagcat catctttcag gatttggaat agctcaactg gaattccatc  40200
acctccacta gctttgttcg tagtgatgct ttctaaggcc cataaccaaa gctaaaacaa  40260
cactcaggtg ttgatgtgac tggtgatgga agtaaagtcc gatgctgtaa agaacaatgt  40320
tgcctaggaa cctggaattt taggtccatg aatcaaagta aattggaaat ggtcaaaaag  40380
aagatggcaa gaatgaacat caattatttt aggggtcagt gaactaaaat ggactgtaat  40440
gggtgaattt aactcagttg accattgtat ctacttactg tgggcaagaa tcccttagaa  40500
gaaatggagt agccctaata gtcaacaaaa gagtccaaaa tgcagttttt gggtacaatc  40560
tcaaaaacaa cagaatgacc tctctttgtt tccaaggtaa acattatcac agtaatccaa  40620
gtctatgccc caaccagtaa tgctgaagaa gctgatgttg aacggttcta tgaagaccat  40680
tatggagaac tgccccagga gccctgactc tccacgcttt gtgggtgctc ctatcggaga  40740
cagggcaagt tgagacatag ctagagaaag acctgaggca gagacaagag atgcaggcct  40800
tgaggtggga aggtgtcagt gttctggaag cctgcaacag gtgaactcaa gtgggccaag  40860
aaaatgcaag acgaggtctc aacagcatct gttccaagtc tattgagagg tacacaaaac  40920
aatctgagta agctgattca tgttattttc ctggatacgc aaacaatgtc ttagctcagg  40980
ctgctatgac aaagtaccac agactgagtg gcttaaagaa cacaaacatt tctcagtatt  41040
tatcatgctt tgaattctat ttgtgcaatg tttgagggga atgcagtgct tatcttttta  41100
ataggtacat taactgtgtc ttcgtttgga tgtaccaaag gatgagacaa tgggagatgt  41160
gagttggtgg atcgatgcct cagcttcccc ttcttgcagc tggatgatct gaggtgtatt  41220
cccattattt cacagatggt ccctgtggca tcaagctcca ctcacctacc atggtaatcg  41280
gcccactttt cctgactttg ctcccttcct tgtctcatgt tttctacttc ctcactttgc  41340
```

-continued ttttctggag gctgggaaaa ataagatctt ggtattggtc aatccagtta ctggtgagga 41400
ctctcttcct ggtttgcaga cagctgcctt cttgctatgt tcttatttgg ctgagacagc 41460
aatcatctct catgtctctt ctcataatga cactgataca ggagatagat gggctccagt 41520
ttagacattt ataactggcc tcctgtttgc attttatggg gcagaaaaaa gtgggcttca 41580
ggctggacac ttacaactag ccttctcttt ggatttcctg gacaaggata ggtgggctct 41640
gggtaaggca cttacaacca gccttctgtt tgctctccaa aatggaagta acaatagaaa 41700
cagagtaaat agccagattt tgtctcttgt caatatctta aaacaatagt cgtggcaaga 41760
acaaagaggg gtaaaatcct atttgagtaa aggattaaag gctctctgct cccctccttc 41820
ttgggacaag ggagacacta cacatgcaca gaaaggctac ttgggagaca aaagtcagag 41880
gaaatgccag gccataatga gtttcccctc ccaaatgctt tcaagtcagt tcattttggc 41940
tgaggggtgc atgaacacgt aaggggaggg tcctgagaca aattagctgg ggggacaaaa 42000
caagatgatt agcctgaggg aagaaaaaga cctggaaaac tcccccctta taaaggattt 42060
aaacttccca aaggcatgac tcttctctga gcttccctgt gcatcttttc acatgtattt 42120
ttccaataaa atttttactt ttctcattac cttctgcctc ctcacctgaa ttctttcttg 42180
acgagacagg catggactat cgacccaggc tctagccaac tggcctttgt ggtctaatgg 42240
ttaggactcc tgatctggga actaagatct tgctccctgc tactgctctc tgctgcttgc 42300
tgcaaggggt tgcttactga tgctagcatc tgaaatcaac actaagctca tccatgaggg 42360
ttctaccctc acgatctaat cattcccaaa ggtcccatct tcatactggg gataagggtt 42420
caatgagtaa atttgggagg gacacaaaca ttcagtccac agtacataaa gatgtcaatc 42480
ttgcacatat ttatttctaa atacaatgcc attccaataa aaattccaac tacaggtttc 42540
ttggaattca acagaattat ataattaacc tggacagaaa aactaagaat attagagaga 42600
ttctaaagca aagagaggat agtggttgat attagtccca ttaagtactg aggcatatga 42660
taaagctttt acccacttca tgtattagta tttatgtggg tttcctagag catgaggaaa 42720
caaacctctt cccatgtagc accccttcct ccagttgtaa caacttgaat tactctgatt 42780
aattgtggag ctatgtaaaa agaaagcagg tatatccacc aagtagggta gcagcttact 42840
gttcaccaat gtgacactgt gctttacaac agtcatccag aagatcacaa tacatttctc 42900
atatatattt agtcatctac tgctcttgat tcacagctcc caaaatctgc gggatttcct 42960
gagcaataag agcaagaaca atgtgagtat cttttgttat aatactgggt ctcttccctc 43020
agttcctaaa atcacttcag agccataaag gtgtcttgtt attaatgcaa gtccctttcc 43080
acaactactg aatttatgtt agtgtaatca cttttcagct tccctggtga ctcagttggc 43140
aaacaatctg cttgcaatgc aggagaccac ctgtaatgca ggagtcctgg gtttgttccc 43200
caggtcatat cccctggaga aggaaatgga aacccactcc agtattcttg cctgggaaat 43260
cccatagaca gagaagcctg gcaggctaca gtccataggg gtcacaaaga ggtggacact 43320
atttagcgac tgaaccacaa tcaccacaat gacttctgga aagcacctaa ggatgggtgg 43380
ctaattgcca gttgccaggg gggacaacct ggcagaattg acagatggaa cttaagttct 43440
agcccatgac ttttgggctg gggtgagata ctagaagttg aatcaattac caaccaccaa 43500
taatttaatc aatcaacttt atgtaatgaa tcctccataa aacccccaaa ggatggcttt 43560
ggagcatccc agttgtgagc atagagactc agtcacatgg acgactccac acggtccctc 43620
aatcccttgc tccatgcatc tcttcatctg actgtttctg aattacaact ttttataata 43680
aaacaggatt gagctataga actcacaaaa atgtgttttt atgagttcta taggcagcat 43740

-continued

```
attaaaaagc agagacatca ctttgtcaac aaaggtccgt ctagtcaagg ctatggtttt  43800
tccagtggtc atgtatggat gtgagagttg gactataaag aaagctgagc accaaaaaat  43860
tgatgctttt gaactgtggt gttggagaag actcttgaga gtcccttgga ctgcaaggag  43920
atccaaccag tccatcctaa aggagatcag tcctgggtgt tcgttggaag gactgatgtt  43980
aaagctgaaa ctccaatact ttggccacct gatgtggaga gctgactcat tggaaaagac  44040
cctgatgctg ggaaagactg tgggcaagag gaaaagggga cgacagagga tgagatagtt  44100
ggatggtatc accgactcaa tggacatagg tttgggtgga ctccaggagt tggtgatgga  44160
cagggaggcc tggcatgctg cggttcatgg ggttgcaaag agtcagacat gactgagcga  44220
ctgaactgaa ctgaactgat gagccactct agcaagttaa tcacaggaaa ggaaggagtc  44280
attggaacct ccagtctata gcagatcagt cagaagcaca gatgacagcc tgaacttaca  44340
actggcatct gagtcaggaa gaggggctat cttatgagac taaatcctta acctgtagga  44400
tctgatacta tctctgggta gatagtgtca gaattgagtt gaattgtagg acttgcaata  44460
atgttggaaa attgctcgtg gcagggaaac caccaccact cctagacaca cacacacaca  44520
cacacacaca ttgggtttga gtgttagaat cattttaacc agtgataaga aagattacca  44580
atggtgcagg aactgccagt ggaaacacaa agtctcctga ccaaaacaga gcaaatcaga  44640
agccaaacct gggttgagaa acaaagaaat gatgacaaaa atcagacagt ttgtttcgaa  44700
aatctgggac caggaagaaa ttaagtgaag agcccaagtg tggcaaaggt tcagggtgac  44760
actaaacttt gttttgcata cctgggaact tcacacatgg ctagacagaa agagaaaagg  44820
acaaattctg tgggaaccaa gggggaaata ggcacagcaa gacgaggaca tgggataggt  44880
aaccacactc gggacattgt ttaactgatt cttctggtag actctcattt gcaaggtcct  44940
gaggctctcc tcccaagcaa tttataacct agttaaatac ggacagaaca gcttaaaatg  45000
gtgctggatg ataccagcca gttgctgctg gagcaggagg aagacagttg agttttgttg  45060
gggaaatatg gacagcttca cagaagagag gggtgtgaag gaattcgggg tgaggaaact  45120
gcttgagcag agcttcagcc aaggcaatta aagaaggagc aactggcctc gcaggactga  45180
agcccagcgg ggattcaggg agaaaggttg tcagaaacat ggtctgggct ttttcacaca  45240
atctgaaccc cagactctgg agtctagcca ctaaggaatc attttatgtg tttaaagaat  45300
ggagagatat agccgcctgt aatacatctg caccatgatg gtttctcttt aaattcacaa  45360
tcattcatcc ttagaaaaaa tgtaatttct gatgcaatag cttaaattgc tgaactgaga  45420
aagtcagagg ggagaaaggg ggaggaatga ggtctttgag gacatgaata ccctcaatga  45480
atgggcccat cctaaagagg accctcatta ttagagaaag tttaaaatac tctccattac  45540
acccatactc tcctccagct aatacctatt tctctgttcc tcccaggaca aaacttctca  45600
gaagaattgt ctctactccc tcaccttcca tttcttcatc aatttactct gtctgttctt  45660
atcactctct tgaaactaat cccatcaagg ccccagtaac gacctccacg tcaccaaatc  45720
cagtgagttc tttcccacct ccattctatt ttgtctctct atagctgact cctgccttct  45780
tgaaaggcac ctcctctctc acactcttga tatcctccta cttcactggc tgtcactttt  45840
cagtctgtct tgctatcttc tctttctcta attcaaagtg tgactcagca gatcagcaac  45900
atctaggaac ccaggagaaa tgcagattct tggacttcat ctcagaatta ctaaatcaga  45960
atctctaagg tgggcccaac cagtccatcc taaaggagat cagtcctggg tgttcattgg  46020
aaggactgat gttgaagctg aaactccaat actttggcca cctgacgtga agagctgact  46080
cattggaaaa gaccctgatg ctgggaaaga ttgagggcag gaggagaagg ggacgactga  46140
```

-continued

```
ggataagatg gttggatggc atcaccgact caatgggtaa actccaggag ttggtgatgg  46200
acagggaggc ctggggtgct gcagtccatg ggtcgcaga gtcggacacg actgagcgac  46260
tgaactgaat tgaactgagg gtgggcccag gaatctgtgt tttatccaga ccccaggtga  46320
tgcacactga aagctaagca ccatgatcta aaactgtctg tttcttacca ttcagtcctg  46380
attcctcttc tttcctctgg ctacactttc tttcttgatg ttatcatcta agcccacaac  46440
tttgaaaatc atctaaatac tggtggtggt ttagtcacct cagtccaact ctttgcaacc  46500
ccagacccct ctgtccatgg gatttcccag gcaagaatac tggttgccat ttccttttcc  46560
aggggatctt cccgaccaag ggatcaaacc cgggtctact gtaatgcagg cagattctta  46620
ctgacaattt ctaaatgcac atcttcagca ccaaccctcc caatctggag attacattaa  46680
aattcaacat accccaaatg gaagaaactt ctctaaaaat ggttgcgtct aaaacttggt  46740
cttcctccat ttctcaccat ttccgaatac atcctctacc accaagcccc atcagtgccc  46800
ctcaggcccc acacaacaat cagaatggtc tttgaaatca ggtcaggtca ccaccctgct  46860
taaatcttca agggcttcct atcacattta attaaaatct aaagacctgg tcattggctg  46920
ttaggcccta catgacctgg tcactttcta tgtggcttcc tgtattccct ttgttgtcta  46980
atgtcagaaa ctataactat ctagttcaca ctaggttctc tataaattat ttgctgaaca  47040
aaatatttct tcttttgaaa ataagagaaa catagagttt acttcgttag cttctccaca  47100
tttgctgagg aggatctatg tgatgttgac aggtaacttc aattgagcca ggacacagga  47160
gatgcgaagg gagactttca aagaatgtct tcatggtgcc ataacctcag cacagccagg  47220
ttccagagga caaacccccca aacatgcttg tcattcagtt cagaatgtag ccttccttat  47280
atataatggg atatagtagt tgtggtgatg gtagagacta agatgaggaa tgatgtaggg  47340
ccatttgcaa aaggtttctc ctgtgggctg accaacgtga tgttgttcat gaggccagtg  47400
aaagccccta agaatctaca accccataat ggcagttttc aaaaatggcc agaaattctt  47460
tgatactctt cccattgaga gatggggtcc atgattcctg cccttgaatc tgcatgggca  47520
tatggctact ttggtcaata gcatatagtg aaagtgatgt tatgtgatat tatgtgactt  47580
ttgagactat gtgagaagcg gcaatgcagc ttccatgttg tttactgaca gtctcacact  47640
tgggtcctct tgggacttct taagccaggt aagaagctca tcaaacttga gactactatg  47700
ctgggaggaa gccaggccac gtggggaagt cacgtgaagg cacttcaatc agtacacctg  47760
attttcaagt cctcccagcc caggtgccag ccatgtaagt gactgaacta attccaactc  47820
ctagctatca cgtcaagcct cagacgtcat ggggcagagt caagtcccca ttgtgcctgt  47880
ccaactcttt ggcctacaca attcatgggc ataataaaat ggtggtttct ttaaaccatt  47940
aagttttgga gtagttgcta catggcaaca atagccagaa taggacaaaa ggtaatgtca  48000
tttcgttccc tcaaaccctc acgaactata ttgccttttg agcattttct tggttggggg  48060
agggaaggaa atcattcagc cagttgacat tggattcttt tgaggaaaaa aggctgagtt  48120
ttggcatcct ctaaaggagc tgtacattgc ccctcctagc aggggaaagt cagtcccttg  48180
cccagcctga tctgatcact cactcccagc tccacccagc tcaagactca aagagatgct  48240
tcactgcccc caatgtgcct cacaataaac aatctctgag gaaagaaggt aaggctctaa  48300
aagtagtgtc aacttaatca ttatgtaaga ctgactggat agaaaacagc cctggcattg  48360
ctgcctaata ctcatttcta gctggccaca atccatttct gctactgaat catcatcatc  48420
ccatcgtcat gttttataga cctctcattt ctccttccca gcagaacttt caggccccca  48480
tccacattca tatattcatc acctcattct acacaattct cctggcctct cccctccctc  48540
```

-continued

```
acttgtcccc atcctatttg agagatccac cctgagatat ttaccctaat gggtgtctca  48600
atatttttaa acctctttcc ttgcaagctt agtggagcct cttgcccata acaaggggac  48660
tagatatttc atttttccca ggtttatacc cattgccctg gcataattaa tattggtact  48720
ctcaaaagtg cacaaatttg ggtaatgata tatatgatcc ctctaaccct aaaacatgtc  48780
ttctatcact tgccatcctt cacatgagac aaacacctac ataaaatttt ggcagtaata  48840
atgatcaagt acacaccatg ttttatacaa gaaacctcag gtaatgtgca gaatggactt  48900
gttaaatgga gtgcatttcc ttcacttatg aatatcataa tctaaatcat ttattttgta  48960
gataatgagc aggaactgag taaatgacgg caggtgatgg ctaatatact ttctaggcct  49020
caaattttaa tctgaaaatt cacaaacatt gggctcaatc cagggcaata gaatttttgt  49080
ccctttttaga aatttctggt taccaaagtt ccagaaattg ctttctcatt ccctaatctt  49140
tcattttctc cattacgtaa cgagaagctg gggctttggc cgattttccc tttaaagatg  49200
atttttatcg tcaacaagca atttcaggga gtgatgagcc ggggaagcgg tattagctga  49260
tgctagcgtt taagctagtc tcaactcgtt tttcccaggg acttagattc ctgggtctgc  49320
cagtaaaccc cgggcgccgg cagctggtgc gcctgagcgt gcgcgcgcgc gccgtcgcct  49380
ccccgcccct gcccctcctc ctccgcccgg cgactcaccc gccctagttg ccagtcgctg  49440
acagccgcag agctgagagc gtcttctctc tcgcagaagc aggtaaatag ccgcgtagtc  49500
ctttaaactc ccagcggagg acgcccaacc ctgggtcttg cggccgaggc cccagggcac  49560
ccagccgaat cggattggtg ggaggcagac cttgaccgtg agtagggctg ggggcttgcg  49620
gcgggcgcgg ggaacgtcgg gcctgttgag cgtgctcgtt ggtttttgcc agccgccgct  49680
cggttttacc ctcctggtta ggagagctcc atttactcgg aatgtgggct ggctggtccc  49740
cctcccgagg tatgtgggtg gtgtgtagga atctagcccc ctcccacgct cgtccactgc  49800
gggagtggga tgggcgaatc gcaccggtag aggagccgca ggtccgagga accgctgggg  49860
agctcagaag aacaagggcg aggccccggg atttgggccc tcccgaagcc cagaggagtc  49920
gcggaattgg gggtgggggt ggtggggaag aaacgggcgc ccaacggggc ccgacctcgg  49980
cggtgaggag tgccggagcg tccgtgggcc cccagccgct gctgccgaac tcctcccgag  50040
aggcggccct gcctgccatc acgcggctgg gaggtacctg ggtagccgca gcgggtgggt  50100
ctctggcaac cccccgggga tcggctctgg cgggcgtgcg tggcctgggc ttcagcctcg  50160
gcgcggggaa tcatgggcca cctggcgctc tctccgggcc agagaaatcc aggtaccggg  50220
aacagtgttt cctgggagct ctgatgtggt ggacccaaaa gcaaagcgaa attttccctg  50280
tctcgactga tcctccggaa ggagggagct cggccgtcgg gagactgagg ggaggggatc  50340
aggcgcctct cggagaacca ccctcatctg ccagtgaggg tggcaccttc acgcttgatt  50400
tttttttttc ccccttcaca cgtttgatta ttaaacaacg agaagtccgt tttttgctgt  50460
cctttttccg tttttttttt tttttttttc cttttggtac catatgtagc aaatagattt  50520
ttttaaaatc ataagcccac caccctcacc atcttttttt cagtttcctc gtctccagat  50580
tcttaacaac aaagcagttt cacctccctg atcatggtta tccttatctc atggccgggt  50640
tattttcttg tacttaagag caatcacgtt ttattaagca gttccccgaa tgctgaacct  50700
ttgaagtgtt acctttcctt acaaaagata ccacatagaa taggattaaa aattttcaca  50760
agttgtcaga gaaaaatagg aacagaaaat tgtataaaaa tgtcagacct ctggaaaatg  50820
aacagctctc tcagatttga aaattaacct atgaaaagga acagttttcc tacggaaaca  50880
ttgaggtgct ctaacaatga aaaagaatca gaaaaggaaa aaaacagagt taggatgtga  50940
```

```
tttgtatatg atttgtatct gatgcaaatt tttcatactt gtgaaagaaa aatatcaaga  51000
ttataaaaag ataaatggtg aaatgaacaa tcatttatga aataaaatac aaatcaaagc  51060
aagtctggat ttacaactac tagtaaaaac aacagtaaca gcaaccactt ctggaaagtt  51120
acctagaaat ttgcatattc agtatgtgag gtggcaaggc tttggagtta gaaatatggc  51180
tctgcaacta attttacagt ttgggaccta atttcctcat ccccctttttg gacattcata  51240
aaatagagga aattatacct acttcaggag tttgccaaga ttaactgtgt aaaactgacc  51300
tttagtgtgt atacttttat tcttttccta gtcacactgc actgggggac gttgtgaatc  51360
tgtatgaaat ttgtgaaaaa cagtcaggtg atcctttaag ccatgaccct aaaaccccac  51420
tcctgggaac ttacctgtaa tggaggaaac caggaaagaa gaagaaaagc tgcattcacc  51480
cacagaactc agaatgatct aaaattagat ccagtccgga gacaacctaa atgtattaat  51540
aaaatagcag ggcagcagct aagaaaatca tagcacttta actgaaagga acattgtgta  51600
accatcacga gtcataattt tagagcctct ctgtgatata caggaaaaaa ctgacaggtc  51660
aaagtaagat tactcagaca tggatgcgtt tgtggaaaat ctgaatgaaa aatgaatcca  51720
cagtttgctg tgtatgggag gagagttcag tgtcacgttt gctgcttttt ttaagttagc  51780
atcatctctt ttttaaaaat actatcatat tttttccctg agtagattca ttagtggttt  51840
aataatttat atactgttat tctgttaaat aatccgttct tagatttatc aattatagtt  51900
ttttcttttt tttttaagga cttctgaata tatttgaaaa ctgaacagtt tcaaccaagc  51960
cgaagcatct gtcttcccag agacacaaat ccaacttgag ctgaatcaca gcagatgtag  52020
gtaccctgca gaatctcttt ggtcttgtga tggttgaaag tgcccaactg tttcacagaa  52080
gataagggac tgaaaggctg ggatcacaaa tccttgctgt ggaggccact gaaatctata  52140
tatgtaaccc acacctatta tatcactctt tcttgtaaaa gcgtcttgat tttgcaggga  52200
aagggacata gctttctctg gaatcattct gagttatgta agaagcagcc atttaaaaaa  52260
tagtataata aaagcaatta cctaacattt ctgcaccaaa tcaacactga aggtgactat  52320
caacagacaa aaggtttatg aggtaatggt ttttctaagc tttagtttta atttacctat  52380
tccattctcc ctttttagat cttatttcct tttccaaggc agccagttta tcaactgtga  52440
actgctgcat atgaagcatt caaaacctga ctgtgtctaa agctgtgatg gctacagcac  52500
aatcatcttt gagtgaatag tatgtttaac agttcttaca gttgggagaa tttttctca  52560
gtttgttcat cctttttctc ctaaccgtgt tctgcttatt gctgttctaa tattgtgtga  52620
tcatgtcaag ggaggtgttc ccttttatgc aaaacattat gttaaatgtt gtcttcccga  52680
gaccaagctc ggaagattgg ctaggagtgc agttccgtgg gaagccttat tataggttcc  52740
taaatctcat cactagatac tcccaggctg ttggcctgat gcagactcta gctatgttgc  52800
ttttcttaaa gctcttcaca tcactctgag gatggactag actggggacc gtttgcccat  52860
ttcagtccag ggctaggcct cagtgtcagt agaaaaacct ccacctcaaa atggtttgta  52920
aatttttgta tagtttgcat tagactcttg ttaagggaca gtgacctcaa aagatgaaaa  52980
tatgacaaat gagttccact tagcttatga aaaattggaa atttccccag ggcaaggatg  53040
ggtagaggga ctgtttggtg ccagtttcca atttaaataa gtctcaaggg tataacatat  53100
tttgagtatc aaaagtgtgg cccctggcac atgaccactg gacataagtt cctaccagct  53160
ctgattctca atccccatgt ataaaaggga ataagatgaa tgggacaata tatggatttt  53220
gttgttgttg ttccttctct ctcgttccat cgctctgcct ttgtgcttat gcactaatgc  53280
cacgagattg tatttattat agttttccaa tccattctga tacttgccag gccaagtata  53340
```

-continued

```
ccttagatgt tcttcctgtt cagtaatttc ttcagtcttc ttaattttga gtatcattat  53400
attctttaaa atcctctttg agttaggact gaaattgtat tgacttaatg attaattgga  53460
gttgaattgg tatctttcaa aatcttcgat cttgattttc ccaaccataa accttgcctg  53520
tctttctttt ctttccagtc ttccagcttt tttcatctaa gttctactat ttattattag  53580
gttaaatctt agtttgaatt ttttgttgcc attaatgagt ggaatttttt tttcacacta  53640
aatcttctaa taattacaac taattggagt attcactctt ttctatatgt tgagttcaaa  53700
aactgccacc ctaataaata agctcattga tttatttgag ggcattttta aatgattgtc  53760
ctggattttc cagatagaaa aatcatacct ggctttctcc atagcagtct aaaatgcagc  53820
aatcacttac attcttgtct tgttaatctc attcacgaga atgcttttcc tctttctgtt  53880
aagatagggt gtggaatatg tattacttct agttctatag aaattttttc aacatcttaa  53940
acttaaaaag tcaggaaagc actgattcct gagtttaagt gagaactttg attttaattg  54000
aaaactttgc aacatcagag aatctttttt ttttctcctt agcctactaa taggttaatt  54060
gatttcatga ttttgagcca ttcttgtatt cctaaaataa tccttattgt cacagtgtat  54120
tctttcacta aaatatcaaa atcaacttgg tggtattttc ttttggattt tggcacccat  54180
attgctaaag gttgggtagc taagagtgtg agcccttcac tccctgtggc tcttaatact  54240
acatctcagg tgaactgccc aaatgtttat ctctactgag taagagttcg agattcttat  54300
aacaattgcc taaattgata ctctcacttg aatggctcat agatatagca aagttaatat  54360
atccaaacta tagctttatt ttttctcaca agcctggccc tccattagtt ttcttgtttg  54420
cattaggtgg catcaccacc atctacctag ttccaaaagc cacaaacctg ctcaactctc  54480
actctcccat ccactctatc agcgtaatcg ttttttttcta caaaatactt cccatttttc  54540
acagctccgt gctgctttgt cacagttcca ggttacacca ccatcttcct ttaatcattt  54600
tctaagtggt ctcaccattt cctttcttat ccctcaaatt tttctcttta acacagcagt  54660
aagggtgaac tttaaaaaaa aaaaatctgt gatgtgattc tcctaagcca ctttaatggc  54720
tttgcactgt ttcaggctcc agacacgtat ctccctgtag tcctcaaacc cacaaactaa  54780
atatcttacc actgtgtcct cagccacaga acagtaatat tagaggacat gtaataaata  54840
tttgttaagt aatcaatagt tattgtacat tgtacattgt acatactagc tgttccataa  54900
atatttattt aatttaaata tttatttaat tgaatgaatt caatatcagt ttttataatt  54960
gaatagaaaa gtaatccctc ccacacagat ttttctttct tttttttttt tttttttat  55020
gaagcaagga atatgactac ttagaaagct ggctgccaga gaaaatggca gactaatgtc  55080
ttaaaacaaa tatcagtgtc tagatgccag gttcttttat agaacagaga tggcaggaag  55140
atgaggaaat aaaggcagaa tagagaggga gaagtggggt ggaagtaaag taaaaaaggc  55200
cacgtcctgc aagacatctc cagaaaggcc agcctgtgga agggatgtgt taatctcttc  55260
ttgcctgcaa ccattcacag gtgggaagtg tcaaattatc tccctgtgag ctgaacaaag  55320
gcacttcagt ccaacagtta gagagaggga ctgggttttc tgaggcaggc tattatatat  55380
gattgtaaca acaacagcaa caaaaagcaa gtcaaagaaa cagttccaat atggagtcag  55440
aattggttct tctcagcaac agttccccac tgtcaaggtc catttgacaa tcttgtagga  55500
aaaggggaca gtgatctttc tgtttgtcag atgaatcttt ctgggagtgt ctgcctttga  55560
tgccagtgtt ccaaatagtg agatttgttt tctttttgtt cctccttgga aagtgtctac  55620
tttatacttg tcaacttaga aatattggac ttcaaaccca ggagggtttc tcaagttaag  55680
aaattttgca cttttctgtg tatgggaaga tgcaagcgtc agggttcatt aaaattattt  55740
```

```
ccttgatgtg taattcagct gtctggggcc tgtgatcctg tattctcaag agtttcctca  55800

aggttcacca tagggagtgg gtgcaatctg atgactgctg gatggcatgt attctccttc  55860

ctgagttttc tccttcctga gttgacttgg ggttcaccag ctcacattag agggcttcaa  55920

ttgttaattc catttctcag gtcttccctt ggtcaggaat ttgaccaata tttgggagac  55980

atttcatggt caaactttgc ttcacggtgc tgtgaggttc atcccaaatc aggcaaaact  56040

tcttgatgta ccactctagg tgctaaattt tggattagac ccccatgaat aattaaagat  56100

tctctggatt ctaattgtca tccaggagac attttccatt gttgcttctt cccataccta  56160

gaatcacact attataatta ttttatgtta taaatgtgat ctattttctc aagatgttta  56220

tccgtagaag ttttgttgga ggcctgatta cacattggtt actgcaagag acaactatct  56280

tataaattag tcaggatata agtaatgcag ctagtaacac tgataatgac atagtgcaac  56340

aggggtgtgc aaagcacaat ctaaaaacaa agaataaagt aaagcaatga ttagtataac  56400

tagttgtagt ccagttgcaa taatctagtg accaaaggag ccataactga tttaatgatc  56460

tatcttcagt ttcattgtac cagccatgcc atagcttaat ctttgagaca agcatatgct  56520

actggcagga tcaaccagat agaagaagat ttaagtttta cttttgctta caaaggatat  56580

aatttaccaa gttactgtaa gtcagaggtt aaggaagttt tccttacacc tgaaaaacag  56640

atttaaacca gttattttta gatagaaacc ataaaaatta taacaagttc agttcactca  56700

gtcctatgta actaatcctt tttgttaaca gctttatgaa gccatcaggt ttcccattag  56760

aattcttcaa tgtgttacta gttcagcatt atggtctaaa agtcagaaac ttggatttat  56820

ctgaaagtcc tttttataaa tcttcttaaa gaggagacat ttttacagag gcaacagagt  56880

gagaccataa ctgtccataa tgaccaaaga cttaagaagg cactttaaat ctgattatga  56940

tgcaattgac aaagtaacct ggttactgct gtgacataca acagtttcag gtagtagaag  57000

tagaatcatg actgataata ttctaccagg acatatcaca tttttaggaa ctccatataa  57060

tctctagtat atcagtatca tttatcatat aatttaagat atattattca ttggacaaca  57120

cttgccatgt agtttaacat accaagtgaa tctaattagt ttaatatctc cctttggtgt  57180

gtctcagggg ccctttgaag caccccaaag ttagctaaag atcaaaggaa ctttattgta  57240

acttgatttg ggaagtcttg tcaaaagagc attaagaaaa aatgttttaa aacacaacag  57300

gatcataggt cactgtgaaa caatagttat ttacttagcc aaaatgacaa taaaagattt  57360

caaaagcaaa tatagaacag attatttaaa aggtagaaat aatctgttat caaaggagag  57420

gaaagccaaa tttgttttgt accaggttac tttcaagatt catttagtca attaaaattt  57480

tttaaactta gtcctgatca tgtacaaaac actttttcag ggtccatgtt tcacgaattt  57540

tccatcactt aatttatttt agcacaattt taactttcaa gttgttgaat atctggagat  57600

atcctaaaat ataattattt ctgaaagttc actctaagct cttatcttca tttgcatttt  57660

ctttgcttaa cagtttattc acatcaagtc cctttccttg ctgacaaatt gtatcaacaa  57720

acaaccataa ataccaaata taatttaata ttaaatattt cccagttcac gtgaacctgg  57780

agctcattta gcttaattgt atttagaatt gtttggtttg taagcactta cttttattta  57840

aaccaattaa atagagctct tttacaaatc aactgcagca atattatcca aagacaaaga  57900

tacatacaaa cacacaaaca gagaggcctc agttcttatt tcaagatttc agtcctgagt  57960

caggcaatgt aaaacccatc agtttacata cgaggttgaa ttaaaattgg atttctcata  58020

gatggaataa gtcaagctca cttggctaga tagctaaata tttgcagaaa aagcacttag  58080

gaattctaat tatcttggcc aacccaactt ctaaattact ttaccttctc taaaatttgc  58140
```

-continued

```
atttaaaaa gacagcataa tgagggttcc tgagaggaca tttgcatctc aaagacattt  58200
gcatctcaga gttacaggca agtttttcca aaaatgactt tgtttctcct ttaatactta  58260
caggcctctt aagataacca gggaaggtct ggggagtagt aaaaggattt atgggatttg  58320
gattattttt ggaaccacac ttctggtgct gtaaagacta catttgtaaa acacagtttt  58380
gtttttcttt tttgagtgat actgaaggat tgacataccc atttacctat gttggaaagt  58440
tttatctttc ctcatttagc ttagctcttg ggaagacaca gaggcaacaa tttaggctcc  58500
tgtaaatcag tctggactga ggggggaacg aggtgaagat aagaaagaca ggctgaggaa  58560
tccgcctcat agtcctacca ggaagatagt ggccagggcg aatgggtcag tgttttgctt  58620
gaaccaatgt gtgcttcaca gtgcacagaa gctgtcttgc tggagttgtt gtagccacaa  58680
gttccggcaa acaaactcac tcagaaggac aatgcagata gtggagtgca gtttattaca  58740
cctgcgggcc caaggcagag tctcctctta gccaaggacc ccgaccagtt tttgtgaaaa  58800
ccttatatat cctaagtgta tgtgcccaaa cccacctccc cgaattccct gaaactagtc  58860
tgaacaaagg aaaagaaaga tacaatcaaa gttaacctgt gattcatatg ccttaagcct  58920
aggtagttaa cagtggacag ttatcaatag gcctgtggtc ataccccaat aagcataata  58980
gaatttatga ttctattcgg ttacacagat aattagggta ttcttttagg ctactgagag  59040
tctaggtatg agccctgggg ctcttgcggg gggggggggg ggtctggttt tccagttagt  59100
atgtcatttc catagatact gggcatatag ctcaaagtcc acagtccagc ccaacatgga  59160
gtcctgcttt caagatggag cctgttctgt ctgtttcttc gttcagagtc agatgctcta  59220
atagcctggt ccattctgtt acccacttag cctgtcacaa gagacttcaa gcgacaggca  59280
ccttaatggc ttttaagtgc ctgacccatg ccctcaaaat attaattggc ctggtactca  59340
gcctaaggga gaaggaggta aggagagccc tgacctgttg ggaggcagct accggggcac  59400
agagggctat taggccttta gaacacccca gagaataacc ctagctagag ttccatagct  59460
attagtctgt ttgcagaggg tttaaggaga aagggatgag ggagtgtgag gagagtggag  59520
accttaaagg aagtacttct ccttttagct caagcaatta gtatcagatg tctatatgtt  59580
accaaagtat ccggaataaa ccaaaatcta gccagctaga gagtcacatt aacatgactt  59640
cccagtttca ttagacctgt gacctttgtc caaaatgctt tataaatgga gttttccttc  59700
acaggggtgc ttcccaagct gaagctgaag ctctccactg tcaaagttac ccagggctcc  59760
cgtagggaaa ttagaatcag atgcctcaag tccaagggag tccccaggcc tcttcactta  59820
tatcagagtg ttcctctcct ttgcaaaaca cttctaattg caagagtgtg taattgtgag  59880
ccatttaggc ccattgctct tctgatctta acatatctaa tatatgtccc ccaaagcttt  59940
tcttcaggat agatgaaata tttcccattt ttataagttt catagcacca aaacacacac  60000
aaaaataggc aaattccaac ataaatgaca caaattccag taccaataca tagatgaacc  60060
agtttccagc tcaggtaaat aaatttaccc tacaaaacaa atgaactaat cccaactgtg  60120
tgcttgttct gtgcccttcc tctggacgca tgcttgctaa gccgcttcag ttgtgtctga  60180
ctctttgcag ctgtttggac tgtgtcccac catgctcctc tgtccatggc attctccagg  60240
caagaatact gccatgccct tggatagact ccagtattct tttactccag tatactcatt  60300
attcttgcct ggagaatccc atggtcagag gagactgaca ggctacagtt catgaggtca  60360
cgaagagtag gacacgactg aaatgacata gcacaaaaca agcacacaag aactagttcc  60420
ccaataaact ggttccaact caggtagaat ccaacaacaa ttcccatctc caacagggta  60480
ccccaaccaa attgactagt cctgtaaagg aaaagcccaa atttagaggg gaatatgttc  60540
```

-continued

```
tcagtgtgca caccagagca acttacccta caaaatcaag tttgtcaact cgtaatagaa  60600
aagggcacac aaaaccacaa acaaatgagc cagctatcga atgaagaaaa ctaatgctat  60660
gaaattgggt ctgtcaactt gtagaagttt gttgattctt tgcttcaact gccaggccct  60720
agggccactg ataccacttc agggaatctt gaaggagaga tcctcagcac aaatggtccc  60780
agcagctgct ggagccttgc cctaatattc cctaacagag ctggctaaac acaaacagca  60840
agtcaaattt gttaccgaat ccaggcttgc tctactgagt gaacaacagg ccagtgaatc  60900
agagatgaga tgttgaggga aagaatgtga ttttattcag taagctggct gaccgagaag  60960
atggcagact aacatctcaa aataaccatc ttcttgggtt ctggagtgcc aggttcttta  61020
tagaacagaa atgaggggaa gtgaggaaat aaaggaaaaa ggcagaatag agagggagag  61080
gcaatgagtc ttgggccatc agtcttgcaa aacatctcta ggaatcccca cacagttttt  61140
taattcataa aacttttaac tttcacagtt aggtctctaa tccatttaga gcgtgctttt  61200
gcatgtagca ttaagctcca atttttattt tccttcaatt tcccagaagt ctctgctaaa  61260
taaactttcc tttctcattg atttgttttg tcaatttatc atttatccag tttggactaa  61320
agtcaatgta tgtggcttta tctctgaact tgttattctg cttcctttga tctatatgtt  61380
catttctagg ttgttaccat atttattact atgactttat actaggattt aatgtttgat  61440
aacagtaggt tctcacctca tttcctttct aaggttgagt ttgttatttg tggacatttc  61500
ttcatccttt attgaattcc tcaaaaaatc cagctacaat tttgattgtc attattattc  61560
atattataag ttcatttgta ggaaattgac atctgtataa tactaggggg ttccactgag  61620
acttttccat ttttacagat catcttcttt gttctttagt agtgttcaat ttctttttcc  61680
cctagtctta ctttctcttg aattaagtca atcctagata ctttacagta tgaaagtgaa  61740
agtgaaagtt gtatctgact ctttgtgacc ccatggacta tacagtccat ggaattctct  61800
aggccagaat actggagtgg gtagcctttc cttgctccag ggcatcttcc caacccaggg  61860
atcaaaccca ggtctcccac attgcaggca gattctttac gaggtgagcc acaagggaag  61920
cccaagaata ctggagtggg tagcttatcc cttctccagt ggatcttcct gacccaggaa  61980
tcaaactggg gtctcctgca ttgtaggtgg tttctttacc aactgagcta tcagggaagc  62040
ccactttaca gtatgagttg aaattattac tatcttattt attaattttt ttctagtcaa  62100
ttattgctga tatagagaaa tgctgttgat tttttaaaac caatccatag ccttgctgaa  62160
ctctagttga gtttcctgtt acctctgcca agtgtgtgga attttctatg tatatgatca  62220
cattaattcc aaataatgac agctggagct cttttcttac agttattgca ccagtctttg  62280
tccttgcata tggcattgga agagggcttc ccaagtggct caatgttaaa gaatccacct  62340
atcaatgagg agatccaggt ttgattcctg ggtcaggaag atccctttga gaaggaaatg  62400
gccacccact ccgttgttct tgcctgggga atctaatgga cagaggagcc tggagaacta  62460
cagtccatgg ggtcacaaaa gagtcggaca caatctagca actaaaataa caataatggc  62520
actggaagga tctccagtcc tgtgacaggg gacgtccttg ttttgtttct gatcataaag  62580
ggactgcatt caaaaattat ctattaatta tgtttaccat ttctgttata taatctttat  62640
taagttaagc aggtttcctc ctattcctag tctgctaaga gtatttttct tagtgatagg  62700
tattcagttc agttcagtct gttgtgtccc actctttgtg tcctccatgg actgcagcat  62760
gccaggcttc cctgtctatc accaactccc agagcttact caaactcatg tccattgagt  62820
cagtgatgcc atccagtcat ctcatcctct gtcatcccct tctcctgccc tcaatctttc  62880
ccagcatcag ggtcttttcc agtgagttct tcacatcagg tggccaaagt gttggagttt  62940
```

```
cagcttcagc atcagtcctt ccaatgaata ttcaggactg atctccttta ggatggactg  63000
gttggatctc cctgcagtcc aagggactct caagagtctt ctccaacata acagttcaaa  63060
atctaggttg gtcataactt tccttccaag gagtaagcgt cttttaattt catggctgca  63120
atcaccatct gcagtgatat tggagcccca aaaataaaga taggtattga ctattatcaa  63180
atacttagta tcttgatgtg ctaaaggatt aggcagcaac ctgactattc tctgagaaca  63240
tcttatatga agtgttataa cacagccagg cattcagaaa cctaatgtgc atttctagta  63300
cttttactgt aatcacagat atgtttcttg aatttgctaa tctttgtagc ataatttgta  63360
cagtgagaga ttttggatta aataatacaa gatcttcttt attttatcac aaacagaaag  63420
aaaattctcc aaggtctcat taagttttga gttcttctta tttttagaaa tgattctcta  63480
cttcaaaaaa attttttatg attttcataa ttaagtgttg cttttgtgtt ctcaactgat  63540
tttaaaatga ttttgtctta atatagttta caattatcca actttattct aatattcaat  63600
tttaaagtaa tgatcagcaa catatgcccg tggccttatg tcctattgcc tgtatctcca  63660
gtccatggtc attcctcacc tccagactca ccaagcttac cagactgact ggtatctctt  63720
gtcccacgtg tagcttgata atggcattgt caaagagaca ctcctcattt gtcttcctat  63780
ggtcttgctc caccttccgt cttctgtcca cagaattgtc caatccagaa atctgggtgc  63840
cacctcaatt cttctagtct ttcatcttcc atgtcaaaca ccaagccttc cagaaagttc  63900
tcatgttcaa ttccctgagg tgtttgagca gaattgtgag cagcatggaa gccaagatct  63960
gagccccatg agcaaatgga gagatcaggg aagcaggcct gcaaaagacc aggtgcaaga  64020
atgaggccat ttggcatatc ccaggaccct gttcctctgg cctttaccca aaacagactc  64080
caaaaattct agtagacata gtctgagcag tttaactggc cttataactt tcaaatatat  64140
ttttatttat acccaggcat ttcaataatg atagtagaaa cataaatggg atgttaattc  64200
attgtttagt catccttcct ctgaatatta tccaagttag tctttagttc tgaaggtcat  64260
gaaaaataat tttataatat ttggtgccac ttttatttga agatgtccca gtgctgggga  64320
tgactaatgt cagcattaca acatatgcca tttttggttt tatggcaaat ggtattttgg  64380
aacatgtagt ttgatgtggg gtacagtaga aagtgtttaa tgatcattct actgtgcatc  64440
tttaatttct gcccttggaa ccacccaggg taagtgagat attcattctg aaagatctga  64500
atcttcaatt cattcatcta taatttgatg aatgtacatt cacaaaggtt cataggttat  64560
catgcaggat actttgttcc caaactgtgc ttgcccttac atgtaagata tgtgtctttt  64620
gtaccaaaaa ttaagagaaa ataagtcact tatgaaccat taaatgctga actaagactc  64680
attcagtgag tgagtaactg caaatactat gaacacagcc tttcttaccc ctttttgaat  64740
agccccattg tctgtctata gaaagaaaaa ttactttata ggtgtgtttg caaaatcttg  64800
cctgtttcct gtttccaaaa gttattgtat tgagaattcc tttgagaaaa ttcttgttgg  64860
gatttatgtg ttcagaagat gataattcct tcatttaaca gatatctatt gtgtaccttc  64920
tctgtgccag gctctgccct ggcccgctaa gaagatagca gcaaacaaaa gaggctcatt  64980
ccctgcttac attcctacat gaggaaagag gacatgaacc agctattcag aaaagtattt  65040
aatgatctca gcacctacct tggggtcttc ccaactggac attagaatca cttccatagg  65100
gcccatgcca gggttcagaa ggttccagga actaatatcc cttataacaa cccaataggc  65160
agagtttcta gggtccccac aagaacaagc ccagttgcaa gaatcactac tttaaagaag  65220
ttcaaagcta tggtaaacct accagatgtt tatagtttct tccaatttat gatacagtgt  65280
accagtcaga ggttattttt atcataagca atgttgctgg cattctacat ttatcaagtt  65340
```

-continued

```
actaggaaac agagccagga attattttaa ggtcaacttt gtccttagag aaggaagagt  65400
tgtgttaaca ctttacctat aattactttc gtgagatgta tggaatgtga agaatattta  65460
tgacctagac tgtttatagc tgatgccact gctatgcagt cattatgcta cagactttaa  65520
gtgattttta catgggcata tgatgctgac accctcttta ttttgcagat aagtcatcat  65580
ggtgaaaagc cacataggca gttggatcct ggttctcttt gtggccatgt ggagtgacgt  65640
gggcctctgc aagaagcgac caaaacctgg aggaggatgg aacactgggg ggagccgata  65700
cccaggacag ggcagtcctg gaggcaaccg ttatccacct cagggagggg gtggctgggg  65760
tcagccccat ggaggtggct ggggccagcc tcatggaggt ggctggggcc agcctcatgg  65820
aggtggctgg ggtcagcccc atggtggtgg ctggggacag ccacatggtg gtggaggctg  65880
gggtcaaggt ggtacccacg gtcaatggaa caaacccagt aagccaaaaa ccaacatgaa  65940
gcatgtggca ggagctgctg cagctggagc agtggtaggg ggccttggtg gctacatgct  66000
gggaagtgcc atgagcaggc ctcttataca ttttggcagt gactatgagg accgttacta  66060
tcgtgaaaac atgcaccgtt accccaacca agtgtactac aggccagtgg atcagtatag  66120
taaccagaac aactttgtgc atgactgtgt caacatcaca gtcaaggaac acacagtcac  66180
caccaccacc aagggggaga acttcaccga aactgacatc aagatgatgg agcgagtggt  66240
ggagcaaatg tgcattaccc agtaccagag agaatcccag gcttattacc aacgaggggc  66300
aagtgtgatc ctcttctctt cccctcctgt gatcctcctc atctctttcc tcatttttct  66360
catagtagga taggggcaac cttcctgttt tcattatctt cttaatcttt accaggttgg  66420
gggagggagt atctacctgc agccccgtag tggtggtgtc tcatttcttg cttctctctt  66480
tgttacctgt atgctaatac ccttggcgct tatagcactg ggaaatgaag agcagacatg  66540
agatgctgtt tattcaagtc ccgttagctc agtatgctaa tgccccatct tagcagtgat  66600
tttgtagcaa ttttctcatt tgtttcaaga acacgtgact acatttccct tttggaatag  66660
catttctgcc aagtctggaa ggaggccaca taatattcat tcaaaaaaac aaaccggaaa  66720
tccttagttc atagacccag ggtccacctg gttgagagct tgtgtcctgt gtctgcagag  66780
aactataaag gatattctgc attttgcagg ttacatttgc aggtaacaca gccagctatt  66840
gcatcaagaa tggatattca tgcaaccttt gacttacggg tagaggacat tttcacaagg  66900
aatgaacata atacgaaagg cttctgagac taaaaaattc caacatatgg gagaggtgcc  66960
cttggtggca gccttccatt ttgtatgttt aaagcacctt caagtggtat tcctttcttt  67020
agtaacaaag tatagataat taagttacct taatttaatt aaactacctt ctagacactg  67080
agagcaaatc tgttgtttat ctggaaccca ggatgatttt gacattgttt agagatgtga  67140
gagttgaact gtaaagaaag ctgagtgctg aagaattgat gcttttgaac tctagtgttg  67200
gagaaaactt gagagtccct tggactgcaa ggagatcaaa ttagtccatc ctaaaggaga  67260
tcagtcctga atattcattg gaaggactga tgctgaagct gaaactccaa tactttggcc  67320
acctgatggg aagaactgaa ggcaggagga gaaggggatg acagaggatg agatggctgg  67380
atggcatcat ggattcaatg gacatgagct tgagtaaact ccaggagttg gcaatcgacg  67440
gagtcctggc atcctgcagt ccatggtgtc gcagagttgg acacgactga gtgactgaac  67500
tgaggtgaac ccagatttta acatagagaa tgcagatata aaaactccat attcatttga  67560
ttgaatcttt tccttaacca gtgctagtgt tggactggta agattataac aacaaatata  67620
ggttatgtga tgaagagaat agtgtacaaa gaaaagaaat atgtgcattt ctttattgct  67680
atcataattg tcaaaaaaca aaattaggtc cttggtttct gtaaaattaa cttttgaatc  67740
```

aacagggagg catttaaaga aatatcttaa attagagaca gtagaaatct gatacattca 67800
gagtggaaaa agaaattcta ttacgattat ttaagaaggt aaaattattt cctgggttgt 67860
tcagtattgt cacctagcag atagacacta ttgttctgca ctgttattac tggcttgcac 67920
tttgtggtat cctatgtaaa aatacatata ttgcatatga cagacttaag aatttctgtt 67980
agagcaatta acatctgaac tatctaatgc attacctgtt tttgtaaggt actttttgta 68040
aggtactaag gagacgtggg tttaatccct aggtcatgta aatcccctgg aggaggaaat 68100
agcaacccac tccagtattc ttgccaggag aatcccatgg gcagaggagc ctggcagggt 68160
gcagtccatg catagggttg caaagagtca gacaagactt gagctactaa acaataacaa 68220
caataaatgc tgggttggct aaaaggttca ttaggttttt tttctgtaag atggctgtct 68280
ttaacttcat tcgaaacaat tttgttagat tgtatgtgac agctcttgta tcagcatgca 68340
tttgaaaaag aaaacaactt accaaaattg gtgaattttt gtatagccat tttactattg 68400
aagatggaag aaaagaagca aaattttcag catatcatgc tgtattattt caagaaagat 68460
aacacaacca aaatgcgaaa atgtatttgt gcagtgtatg gagaaggtgc tgcaactgat 68520
caagcttgtc aaagtagttt gtgaagtttt gtgctggaga tttcttactg gacaatgctc 68580
cacagtcggg tataccagtt gaagttgata gtgatcaaat tgagatattg agaacaatca 68640
atgttatacc acgtgggaga tagctgacat actcaaaata tccaaataga accttgaaaa 68700
ccatttgcac catctcagtt atgttaataa ctttgatgtt tgagttccac ataaattaag 68760
caaaaaaaaa acaaaaacaa aaacacacaa ccttgaccat atttgcatat gcagttctct 68820
actgaaatga atgaaaacac ttttgttttt aaaaacagat tttgatgaac agtggatact 68880
atacaataac gtagaatgga aaagactgtg gggtgagcaa aatgaaccag caccaccaaa 68940
ggccaggctt catccaaaga agatgtgtgt atggtgggat tggaaagtaa tcctctatta 69000
tgggattctt ctggaaaacc aaaaaatcaa ttccaacaag tactgctcct aattagacca 69060
actgaaagca gcattcaatg aaaagcatcc agaattagtc aatagaaagc atataatctt 69120
ccatcaggat aacacaagac tacatttctt tgatgaccca gcatggctga gaggttctga 69180
ttcacctgct gtattcagac attgcatctt tggatttcca tttatttcag tctacagaat 69240
tatcatcatg aaaaaaattt ccattccctg gaagattgta aagtgcatct ggaaaacttc 69300
tttgctcaaa aagataaaaa gttttgtgaa cacagaatta tgaagttgcc tgaaaaacgg 69360
cagaagatag tgactatgtt gttcagtaaa gttcttggtg caaatgtgtc ttttattttt 69420
atttaaacac taaaggcacg ttttggccaa cccaatactg aatacttaaa ggaaactctt 69480
ccgtgttgtc cttagcctta cagcgtgcac tgaatagttt tgtataagaa tccagagtga 69540
tatttgaaat acgcatgtgc ttatattttc tatatttgta actttgcatg tacttgtttt 69600
gtgttaaaag tttataaata tttaatatct gactaaaatt aaacaggagc taaaaggagt 69660
atcttccacg gagtgtctgg ctgttttcac cagtgtgcac accatgttgg cagcttcatt 69720
tggggggtta atatgagaaa agtggcacat tcagtcctca cactgccagt tgcggcagga 69780
gggcttctcc tgatcctgcc tcagccttac tcccagtcac atgccagctg ttctctgcta 69840
ccttttcata tttttccatg aatacccgtc aaagttacta ctatagcgga ggaaaacagt 69900
ccttgcattc tggaagattt tttctgacca ggattttgaa atagaggatt ttcgtgatta 69960
agatgagact taacaaagta tctaccttat gcctgtaccc acccttgaca ccatttcagg 70020
tcataaactg tgaggcctgg tgacaacacc cattgaattg aaattcaaca ctgtacggtc 70080
aatatggcta ctttcctttg ttacaggctt tcaaatggtt cttcatatgt ttcctccttc 70140

-continued

```
ccaagtatga ggtgccagct cccagttttc cttcacaaag gtttcttct gcaactgtag  70200
ttcattaaca gccggaagaa ataataaatg atagtggttg aaatcataac atttattaac  70260
actttaataa atgccagtgt ccttcagtat ctgaacagag gatcaacttt gcattaaaaa  70320
tgaaaagatt aaaaatcaac atcttgatat cccataattc acaaaataat ttaaaaatga  70380
cataaaatcc tcaaaagcat tactcagtta atctttaaca taagaagtgc taggactatt  70440
ttcatgctgt ccttttggcc atatgtaaga ttatttaaaa atagactatt cattatctgc  70500
caatcataat ctcccaagaa taccccactg aaaagatgtc agttatacaa agcaaggtat  70560
ttacagggcc gaagtgaatg atacacatct gtatttttct caggctacca tgtttcttc  70620
ctgttacttc caattccttt gagttgtgct aaagaaattt ctttatattt catatgtatt  70680
tttaaataga ggataattac tttacaatat tgtgatggtt tctgccatac atcagcatga  70740
atcagcatag ggcttcccag gtggcactag cggtaaagaa ctcacctgcc agtgcaggag  70800
acataagaga tgtgggttca atccctgagt caggaagatc ccctggaaga gggcatggca  70860
acccactcca gtattcttgc ctcgagaatc tccatgggca gagcagcccg gtgggccaca  70920
gtccataagg ttgcaaagag tcggacacaa ctgatgtgac ttagcatgca tgcatacata  70980
tggcccctc cctcttgaac cccctctacc acctccctcc ccacccaccc ctctaggttg  71040
tcgcagagta ctagctttgg tttccctgca tcatacattg aactctcact ggctggctgt  71100
tttacatatg gtatatgttt cagtgctatt ctctcatatc atctcacact ctccttccct  71160
tactgtgtcc aaaatgtctg tgtttccttt gctgccctgc aagtaggact atctttctag  71220
attccatata tatgtgttaa tgtatgatat ttgtctttct ctttctaact tatttcactc  71280
tgtataatag gctctaggtt catccacctc attagaacag actcaaatat gttccttttt  71340
atggctgagt aatattccat tgtgtatatg taccacaact tcattatcca ttcatctgtc  71400
tatggttgga catctaggtt gtttccatgt cctaggtatt gtaaattgtg ctgcaataaa  71460
cattgaggta tatacatctt tttcagttct ggtttcctca gggtatatgc ccagtagtga  71520
gactgctggg tcatatggta actttgggct tcccttgtgg ctctgctggt aaagaatcca  71580
cctgcaatgc gggagacctg ggtttggtcc tgggctggga agaccccctg gagaagggaa  71640
tggctaccca ccccagtatt ctggcctcta gaattccatg gactgtatag tccatggagt  71700
tgcaaagagt tgcacacgac tgagcaactt tcactcacct atggtaactt tatttctagt  71760
cttttaagga aactccatac tgttctccat ggtggctgta tcagtttgca ttatgaccaa  71820
cagtgtcaga gagttccctt ttctccacat cctctccagc atttattttt tgtaaacttt  71880
ctgatgatgg ccattctgac caatatgaga tgacatctca ttgtagtttt gtttgcattt  71940
ctctaaaatg agtgatgttg agtatctttt catgtaatta ttagtcatct gtcatctttg  72000
gagaaatgtc tgtttgagtc ttctgcccat tttttaaatt tggttgtttt ttgttactga  72060
gctgcttatg tattttggag attaattcct ttcagttgtt tcatttgcta ttattttctc  72120
ccattctgag agttgtcttt tcaccttgct tatggtttcc ttcattgtga aaaaactttt  72180
aagtttaatt aggtcccact tatttatttt tgtttgtatt tccattattc taggaagggg  72240
gtcaaagagg atcttactat tctgcctatg ttttcctcta agagtcttat agtttctgat  72300
cttacattta ggtctttcat ccattttgag tttatctttg tgtatggtgt taggaagtgt  72360
tctaatttca ttcttttaca tgtagctgac cagttttccc agtaccagtt attgaagagg  72420
ctgtcttttc tccattgtat atttttgcct cttttgtcaa agataaggtc ctcatcagat  72480
cagatcagat cagatcagtc actcagtcat gtctgactct ttgcgacccc atgaatcgca  72540
```

-continued

```
gcatgccagg cctccctgtc caacaccaac tcccggagtt tactgagact cacgtccatc  72600

gagtcactga tgccatccag ccacctcatc ctctgtcatc cccttttcct cctgccccca  72660

atccctccca gcatcagagt cttttccaat gagtcaactc tttgcatgag gtggccaaaa  72720

tattggagtt tcagctttag catcattcct tccaaagaaa tcccagggct gatgtccttc  72780

agaatggact ggttggatct ccttgcagtc ggactctcaa gagttctcca acaccacagt  72840

tcaaaagcat caattcttca gtgctcagcc ttcttcacag tccaactctc acatccatac  72900

atcaccacag gaaaaaccat agccttgact agatggacct tggttggcaa tgtctctgct  72960

tttgaatatg ctatctaggt tggtcataac tttccttcca aggagtaagc atcttttaat  73020

ttcatggctg cagtcaccat ctgcagtgat tttggagccc agaaaaaataa agtctgacac  73080

tttccactgt ttccccatct atttcccatg aagtaatggg accggatgcc atgatctttg  73140

ttttctaaat gttgagcttt aagccaactt tttcactctc cactttcact ttcatcaaga  73200

ggctttggtg catggattta tctccaggct ttctattttg ttccattggt ctatatttcc  73260

atttctgtga cagtaccata ctgtcttgat gaccatagct ttgtagtata gtctgaagtc  73320

aggaaggttg attcctccag tgtcattctt ctttctcaag attgctttgg ctatttgggg  73380

tcttttgtgt ttccatacaa attgtgaaag tatttgttct agttctgtga caaataccat  73440

tattagtttg ataggaattg cattgaatct atagattgct ttggataaca tagtcatttt  73500

cactatattg attcttccga tccaagaaca tggtatatct ctgagacagg aaacccgcgc  73560

tgtgagtgct tgatcaagcc caagagaata gtccgcaagc cggtttttgt gtgtttgttt  73620

ttggcccttt ggtaactatc ggtaaattta ttcctaggta tttttgttgt tgttgttgca  73680

atggtgaatg ggattgtttc cataatttct ctttctgatt tttcattgtt agtttatagg  73740

aatgcaaggg atttctgtgt attaatttta tatcctgtga ctttactgta ttcattgatt  73800

agctctagta atttttatgt ggcctcttta tagagtttcc tatatagagg atcacatgat  73860

ctgcaaacag agttttacta cttcttttcc aatctggatc cttgtgttaa aggattttta  73920

ctaaaaaatt aaaatatcaa ttttaaataa ctgagtctaa ctcttacaga aggtttttct  73980

ggagaagtgt caggtgtcaa actttctttc ccttcctctc tctctggaat taaagccaaa  74040

gaagtgtcct ctgccttgga agaaattttg ggtctgtatt gcttctcact ctagtgggaa  74100

ccttaatatg gccagaacct gagcttcccc aggctcaggc cctgaccttc cattggtcta  74160

agcaactgac ctacatagtt catttccact tgagaatggt cagttcctct ctggctcttt  74220

gaaactcctg gaggatttag cttctcctgc attaactgga ggaactaaac ccatcctttg  74280

ccccactcct gtgaggccta cccctgttct ccaagaagcc acaccttctg ctacacacat  74340

tcagcctatg agcttcaact ctgccttgct acaattttcc tttcctggag agctggtgtt  74400

ctgttctttc cctggagtag tgtgcctcaa acttgaatgt gcacctgaca ggggcccaag  74460

attctgcatt tcttacaggt tcccagatga tgccatgctg gttctgtgaa acttcactgg  74520

aacagctccc tcaggatttc acactggagc ctctaccagc accacctgaa gttcaacaca  74580

agttgctgca ccccacccca gagtttctga ttccagagtg cagggtagga ccagagaatt  74640

tacatttcta acacactccc tggcaatgct gctgttgatg tggagattgc aaatggagct  74700

ccactgctct acaggaagat gtacatggaa tagaaggcaa cctggccctg aaaaatagag  74760

cagttaggag actaaaaatc taattggaat gctccctgag gaggagagag ctgagagctc  74820

tagggatgaa aagcaaagga gacataagga agtagttaat acctgctgcc tgaaaaactg  74880

gaagcactgg tgagtcctga ggcccaccac tagtgagaga ttcagctaaa cttggaatag  74940
```

-continued

```
tagccaggcc acaaatgcag cacttctcaa attcagatgt gcgcacaaat cacccaagaa  75000
ccctgtcaaa atgcagttct gaggccatat gtttgatgta agcttggaga tgtgtcattt  75060
ctataagctc ccaggtgatg tgtggtccca gtggtcccag gaccacacca agaaacaagg  75120
acctagaagc ctaagtcatc tcttctaacc gtggccaaga ctttaaataa gcattgaagt  75180
ctcaggagct ggggggaggt ggggagtagc caatagagag tcttcacctt ttcttgattt  75240
agccctaagt tttgcctgtc gtgctttgag agcacattcc tcttacctat caacctcctg  75300
ctggcagcag tgaagtcagc ttgtgtatta tctctgaaac aagctgaatt agttggctgc  75360
ccatgggaaa tatcaaatcc agagacactc tgtcagtttt tcaaggtcat acaaatagtg  75420
agtgaaaatt ttagttgctc agtcatgtct gattctttgc aaacttatgg actatagctg  75480
ccaggctcct ctgtccatgg aattctccag gcaagaatac tggagtgggt tgccataccc  75540
tcctccaggg gatcttctgg acccggggat cttctggacc cagggatcaa accctctctc  75600
tgttgcaggc agattcttta ctgtctgagc caccagggaa gcccacacaa atagtatgtt  75660
caccaaagca cattgtggaa actctttgcc ttggtttgtg tttatattta agggtttggc  75720
tcaaaggtcc gacatctcag tcactgtgca caactcatgg cctctgtcaa gggtgccccc  75780
tggtgcaggg ctccagcttg aggggactca gttgaatcca aggggaacct gaaggaaggg  75840
tcagaaatcc taaaagcaaa ttcagcccaa aatgcctcct accctatttg attcctccat  75900
cactcactgt cccatacaca cttctctcat attatttcag aagtgacctg tagccagggc  75960
ccatagatta gtagccctct ccaatcaaac catagttccc taagccctag aacacataca  76020
tgtcacctcg tgccagagcc cctaggctgg aggccaccag ggtaattggg actgggggct  76080
tctttctccc taactgtcct ggcaaatctg cccctttcct ccttctctaa aaacaaacag  76140
taaacaaaca aaagcaagat cgttatctta atctttatat cgagtaaaaa taaaagtttt  76200
cagtaactct attctttagc acccttactc aacctaatca tttaagaaaa ccttacaggc  76260
ccttgtttca ttgcctttct tgttgaatat accatcttga ttagttttct ggggttgcca  76320
ttaaaaaaaa aaaaaagtgc cacagattga atggcttaaa caacagatat ttactttctc  76380
actcttctgg agactggaag tctgagatta aagtatcatc agggttggtt tcttctctga  76440
cttgtagatg gcctccctat gtcttcccac agtcttccct ttttgtgtct ctgtgtccta  76500
atctcttttt ataaggacca gttcatgctc tatcatgaga ccctatggac tatagccctc  76560
taggctcctc tgtccatggg gttttccaga caagaatact gtgggttgct attttctcct  76620
ctaggcaatc tttctgaccc agggatcaag cccacgtgtc ctgtatctcc tgcattgcag  76680
atggattctt tactgctgag ccactgggga agccctttta taaggactgg gcttcccttg  76740
tggctcggcc ggtaaagaat acacgtgcaa tgcaggagac cagggtttga tccctgggtc  76800
aggaagatcc cctggagaag ggaatggtaa cccactcctc aaattgtatt tgaggtgagg  76860
actgctactg ctgctgctaa gtcgctttag tcgtgtccaa ctctgtgcga ccccatagac  76920
ggcagcccat caggctctcc tgtccctggg attctccagg caagaacact ggagtgggtt  76980
gccatttcct tctccactgc atgaaagtga aaagtgaaag tgaagtcacc actcctcaaa  77040
ttggatttga ggtaaggaca ccactcctca aattgaatta gggctcaccc taatggcttc  77100
atcttaacct aactttaact ctttaaaggc cctaactcca aatacagtca ttttgaggta  77160
ttaaggacta tgactccaac acctatcaag aaatgtcaca gcagtatgtt agtgtcagtc  77220
tcaagagcgc tcaaaggcag tcccaggact aagacaacct taatggcagc ctcacagtca  77280
cattctattc ccttatcagg atcacactat tccttcaata gactgagcca ctgcccatca  77340
```

atccacttag aattgccaag ggtacctatc tcatagtgcc cattgcagag caaacagaaa 77400
tgcttccatt ctggatacag accctgaaac ccagccacca tgcccccatg gctcacacaa 77460
agagcttcat aatcaaacaa atttgccctt tggtttgtat ccacacacaa atacactaca 77520
aacacacctg gcttagagtt acactgatta tgagttaatt gacataaaac tgagtgttag 77580
ctataattta aggggtacta tctctaattt tcttgaagag atctctcatc tttcccattc 77640
tgttgttttc ctctatttct ttgcattggt ccctgagaaa ggctttctta tctcttcttg 77700
ctattcttgg gaactctgca ttcagatgct tatatctttc cttttctcct ttgcttttcg 77760
cttctcttct tttcacagct atttgtaagg cctccccaga cagccatttt gctttttttgc 77820 atttcacgca aagatgggct tgataaagga cagaaatggt atggacctaa cagaagcagg 77880
agatattaag aagaggtggc aagaatacac agaagaactg tacaaaaaag atcttcatga 77940
cccagaaaat cacgatgatg tgatcactga cctagagcca gacatcctgg aatgtgaagt 78000
caagtgggcc ttaggaagca tcactaccaa caaagctagt ggaggtgatg gaattc 78056

<210> SEQ ID NO 2
<211> LENGTH: 771
<212> TYPE: DNA
<213> ORGANISM: Artificial Sequence
<220> FEATURE:
<223> OTHER INFORMATION: Majority Sequence prepared to show the alignment of bovine, ovine, cervid and human Prnp nucleotide sequences.

<400> SEQUENCE: 2
atggtgaaaa gccacatagg cagttggatc ctggttctct ttgtggccat gtggagtgac 60
gtgggcctct gcaagaagcg accaaaacct ggaggaggat ggaacactgg ggggagccga 120
tacccgggac agggcagtcc tggaggcaac cgctatccac ctcagggagg gggtggctgg 180
ggtcagcccc atggaggtgg ctggggccag cctcatggag gtggctgggg tcagccccat 240
ggtggtggct ggggacagcc ccatggtggt ggctgggggc atcaaggtgg tacccacagt 300
cagtggaaca agcccagtaa gccaaaaacc aacatgaagc atgtggcagg agctgctgca 360
gctggagcag tggtaggggg ccttggtggc tacatgctgg gaagtgccat gagcaggcct 420
cttatacatt ttggcagtga ctatgaggac cgttactatc gtgaaaacat gcaccgttac 480
cccaaccaag tgtactacag gccagtggat cagtatagta accagaacaa ctttgtgcat 540
gactgtgtca acatcacagt caagcaacac acagtcacca ccaccaccaa gggggagaac 600
ttcaccgaaa ctgacatcaa gatgatggag cgagtggtgg agcaaatgtg catcacccag 660
taccagagag aatcccaggc ttattaccaa agaggggcaa gtgtgatcct cttctcttcc 720
cctcctgtga tcctcctcat ctctttcctc atttttctca tagtaggata g 771

<210> SEQ ID NO 3
<211> LENGTH: 795
<212> TYPE: DNA
<213> ORGANISM: Bos taurus

<400> SEQUENCE: 3
atggtgaaaa gccacatagg cagttggatc ctggttctct ttgtggccat gtggagtgac 60
gtgggcctct gcaagaagcg accaaaacct ggaggaggat ggaacactgg ggggagccga 120
tacccaggac agggcagtcc tggaggcaac cgttatccac ctcagggagg gggtggctgg 180
ggtcagcccc atggaggtgg ctggggccag cctcatggag gtggctgggg ccagcctcat 240
ggaggtggct ggggtcagcc ccatggtggt ggctggggac agccacatgg tggtggaggc 300

```
tggggtcaag gtggtaccca cggtcaatgg aacaaaccca gtaagccaaa aaccaacatg    360

aagcatgtgg caggagctgc tgcagctgga gcagtggtag ggggccttgg tggctacatg    420

ctgggaagtg ccatgagcag gcctcttata cattttggca gtgactatga ggaccgttac    480

tatcgtgaaa acatgcaccg ttaccccaac caagtgtact acaggccagt ggatcagtat    540

agtaaccaga acaactttgt gcatgactgt gtcaacatca cagtcaagga acacacagtc    600

accaccacca ccaaggggga gaacttcacc aaaactgaca tcaagatgat ggagcgagtg    660

gtggagcaaa tgtgcattac ccagtaccag agagaatccc aggcttatta ccaacgaggg    720

gcaagtgtga tcctcttctc ttcccctcct gtgatcctcc tcatctcttt cctcattttt    780

ctcatagtag gatag                                                     795
```

<210> SEQ ID NO 4
<211> LENGTH: 795
<212> TYPE: DNA
<213> ORGANISM: Bos taurus

<400> SEQUENCE: 4

```
atggtgaaaa gccacatagg cagttggatc ctggttctct ttgtggccat gtggagtgac     60

gtgggcctct gcaagaagcg accaaaacct ggaggaggat ggaacactgg ggggagccga    120

tacccaggac agggcagtcc tggaggcaac cgttatccac ctcagggagg gggtggctgg    180

ggtcagcccc atggaggtgg ctggggccag cctcatggag gtggctgggg ccagcctcat    240

ggaggtggct ggggtcagcc ccatggtggt ggctggggac agccacatgg tggtggaggc    300

tggggtcaag gtggtaccca cggtcaatgg aacaaaccya gtaagccaaa aaccaacatg    360

aagcatgtgg caggagctgc tgcagctgga gcagtggtag ggggccttgg tggctacatg    420

ctgggaagtg ccatgagcag gcctcttata cattttggca gtgactatga ggaccgttac    480

tatcgtgaaa acatgcaccg ttaccccaac caagtgtact acaggccagt ggatcagtat    540

agtaaccaga acaactttgt gcatgactgt gtcaacatca cagtcaagga acacacagtc    600

accaccacca ccaaggggga gaacttcacc gaaactgaca tcaagatgat ggagcgagtg    660

gtggagcaaa tgtgcattac ccagtaccag agagaatccc aggcttatta ccaacgaggg    720

gcaagtgtga tcctcttctc ttcccctcct gtgatcctcc tcatctcttt cctcattttt    780

ctcatagtag gatag                                                     795
```

<210> SEQ ID NO 5
<211> LENGTH: 845
<212> TYPE: DNA
<213> ORGANISM: Bos taurus

<400> SEQUENCE: 5

```
atggtgaaaa gccacatagg cagttggatc ctggttctct ttgtggccat gtggagtgac     60

gtgggcctyt gcaagaagcg accaaaacct ggaggaggat ggaacacwgg ggggagccga    120

tacccrggac agggcaktcc tggaggcaac cgttatccac ctcagggagg gggtggctgg    180

ggtcagcccc atggaggtgg ctggggccag cctcatggag gtggctgggg ccarcctcat    240

ggaggtggct ggggtcagcc ccatggtggt ggctggggac agccacatgg tggtggaggc    300

tggggtcaag gtggtaccca cggtcaatgg aacaaaccya gtaagccaaa aaccaacatg    360

aagcatgtgg caggagctgc tgcagctgga gcagtggtag ggggccttgg tggctacatg    420

ctgggaagtg ccatgagcag gcctcttata cattttggca rtgactatga ggaccgttac    480

tatcgtgaaa acatgcaccg ttaccccaac caagtgtact acaggccagt ggatcagtat    540
```

-continued agtaaccaga acaaytttgt gcatgactgt gtcaayatca cagtcaagga acacacagtc 600
accaccacca ccaaggggga gaacttcacy gaaactgaca tcaagatgat ggagcgagtg 660
gtggagcaaa tgtgyatyac ccagtaccag agagaatccc aggcttatta ccaacgaggg 720
gcaagtgtga tcctcttctc ttcccctcct gtgatcctcc tcatctcttt cctcattttt 780
ctcatagtag gataggggca accttcctgt tttcattatc ttcttaatct ttaccaggtt 840
ggggg 845

<210> SEQ ID NO 6
<211> LENGTH: 936
<212> TYPE: DNA
<213> ORGANISM: Bos taurus

<400> SEQUENCE: 6
tatgatgctg acaccctctt tattttgcag ataagtcatc atggtgaaaa gccacatagg 60
cagttggatc ctggttctct ttgtggccat gtggagtgac gtgggcctct gcaagaagcg 120
accaaaacct ggaggaggat ggaacactgg ggggagccga tacccaggac agggcagtcc 180
tggaggcaac cgttatccac ctcagggagg gggtggctgg ggtcagcccc atggaggtgg 240
ctggggccag cctcatggag gtggctgggg ccagcctcat ggaggtggct ggggtcagcc 300
ccatggtggt ggctggggac agccacatgg tggtggaggc tggggtcaag gtggtaccca 360
cggtcaatgg aacaaaccca gtaagccaaa aaccaacatg aagcatgtgg caggagctgc 420
tgcagctgga gcagtggtag gggccttgg tggctacatg ctgggaagtg ccatgagcag 480
gcctcttata cattttggca gtgactatga ggaccgttac tatcgtgaaa acatgcaccg 540
ttaccccaac caagtgtact acaggccagt ggatcagtat agtaaccaga acaactttgt 600
gcatgactgt gtcaacatca cagtcaagga acacacagtc accaccacca ccaaggggga 660
gaacttcacc gaaactgaca tcaagatgat ggagcgagtg gtggagcaaa tgtgcattac 720
ccagtaccag agagaatccc aggcttatta ccaacgaggg gcaagtgtga tcctcttctc 780
ttcccctcct gtgatcctcc tcatctcttt cctcattttt ctcatagtag gataggggca 840
accttcctgt tttcattatc ttcttaatct ttaccaggtt gggggaggga gtatctacct 900
gcagccccgt agtggtggtg tctcatttct tgcttc 936

<210> SEQ ID NO 7
<211> LENGTH: 771
<212> TYPE: DNA
<213> ORGANISM: Ovis canadensis

<400> SEQUENCE: 7
atggtgaaaa gccacatagg cagttggatc ctggttctct ttgtggccat gtggagtgac 60
gtgggcctct gcaagaagcg accaaaacct ggcggaggat ggaacactgg ggggagccga 120
tacccgggac agggcagtcc tggaggcaac cgctatccac ctcagggagg gggtggctgg 180
ggtcagcccc atggaggtgg ctggggccaa cctcatggag gtggctgggg tcagccccat 240
ggtggtggct ggggacagcc acatggtggt ggaggctggg gtcaaggtgg tagccacagt 300
cagtggaata agcccagtaa gccaaaaacc aacatgaagc atgtggcagg agctgctgca 360
gctggagcag tggtaggggg ccttggtggc tacatgctgg gaagtgccat gagcaggcct 420
cttatacatt ttggcaatga ctatgaggac cgttactatc gtgaaaacat gtaccgttac 480
cccaaccaag tgtactacag accagtggat cagtatagta accagaacaa ctttgtgcat 540
gactgtgtca acatcacagt caagcaacac acagtcacca ccaccaccaa gggggagaac 600

-continued ttcaccgaaa ctgacatcaa gataatggag cgagtggtgg agcaaatgtg catcacccag 660
taccagagag aatcccaggc ttattaccaa aggggggcaa gtgtgatcct cttttcttcc 720
cctcctgtga tcctcctcat ctctttcctc atttttctca tagtaggata g 771

<210> SEQ ID NO 8
<211> LENGTH: 771
<212> TYPE: DNA
<213> ORGANISM: Ovis aries

<400> SEQUENCE: 8
atggtgaaaa gccacatagg cagttggatc ctggttctct ttgtggccat gtggagtgac 60
gtgggcctct gcaagaagcg accaaaacct ggcggaggat ggaacactgg ggggagccga 120
tacccgggac agggcagtcc tggaggcaac cgctatccac ctcagggagg gggtggctgg 180
ggtcagcccc atggaggtgg ctggggccaa cctcatggag gtggctgggg tcagccccat 240
ggtggtggct ggggacagcc acatggtggt ggaggctggg gtcaaggtgg tagccacagt 300
cagtggaaca agcccagtaa gccaaaaacc aacatgaagc atgtggcagg agctgctgca 360
gctggagcag tggtaggggg ccttggtggc tacatgctgg gaagtgccat gagcaggcct 420
tttatacatt ttggcaatga ctatgaggac cgttactatc gtgaaaacat gtaccgttac 480
cccaaccaag tgtactacag accagtggat cagtatagta accagaacaa ctttgtgcat 540
gactgtgtca acatcacagt caagcaacac acagtcacca ccaccaccaa gggggagaac 600
ttcaccgaaa ctgacatcaa gataatggag cgagtggtgg agcaaatgtg catcacccag 660
taccagagag aatcccaggc ttattaccaa aggggggcaa gtgtgatcct cttttcttcc 720
cctcctgtga tcctcctcat ctctttcctc atttttctca tagtaggata g 771

<210> SEQ ID NO 9
<211> LENGTH: 771
<212> TYPE: DNA
<213> ORGANISM: Odocoileus virginianus

<400> SEQUENCE: 9
atggtgaaaa gccacatagg cagctggatc ctagttctct ttgtggccat gtggagtgat 60
gtgggcctct gcaagaagcg accaaaacct ggaggaggat ggaacactgg ggggagccga 120
tacccgggac agggaagtcc tggaggcaac cgctatccac ctcagggagg gggtggctgg 180
ggtcagcccc atggaggtgg ctggggccaa cctcatggag gtggctgggg tcagccccat 240
ggtggtggct gggggcagcc acatggtggt ggaggctggg gtcaaggtgg tacccacagt 300
cagtggaaca agcccagtaa accaaaaacc aacatgaagc atgtgggagg agctgctgcc 360
gctggagcag tggtaggggg ccttggtggc tacatgctgg gaagtgccat gagcagacct 420
cttatacatt ttggcaacga ctatgaggac cgttactatc gtgaaaacat gtaccgttac 480
cccaaccaag tgtactacag gccagtggat cagtataata accagaacac ctttgtgcat 540
gactgtgtca acatcacagt caagcaacac acagtcacca ccaccaccaa gggggagaac 600
ttcaccgaaa ctgacattaa gatgatggag cgagttgtgg agcaaatgtg catcacccag 660
taccagagag aatcccaggc ttattaccaa agaggggcaa gtgtgatcct cttctcctcc 720
cctcctgtga tcctcctcat ctctttcctc atttttctca tagtaggata g 771

<210> SEQ ID NO 10
<211> LENGTH: 771
<212> TYPE: DNA
<213> ORGANISM: cervus canadensis -continued

<400> SEQUENCE: 10
atggtgaaaa gccacatagg cagctggatc ctagttctct ttgtggccat gtggagtgac 60
gtcggcctct gcaagaagcg accaaaacct ggaggaggat ggaacactgg ggggagccga 120
tacccgggac agggaagtcc tggaggcaac cgctatccac ctcagggagg gggtggctgg 180
ggtcagcccc atggaggtgg ctggggccaa cctcatggag gtggctgggg tcagccccat 240
ggtggtggct ggggacagcc acatggtggt ggaggctggg gtcaaggtgg tacccacagt 300
cagtggaaca agcccagtaa accaaaaacc aacatgaagc atgtggcagg agctgctgca 360
gctggagcag tggtaggggg cctcggtggc tacatgctgg gaagtgccat gagcaggcct 420
cttatacatt ttggcaatga ctatgaggac cgttactatc gtgaaaacat gtaccgttac 480
cccaaccaag tgtactacag gccagtggat cagtataata accagaacac ctttgtgcat 540
gactgtgtca acatcacagt caagcaacac acagtcacca ccaccaccaa gggggagaac 600
ttcaccgaaa ctgacatcaa gatgatggag cgagttgtgg agcaaatgtg catcacccag 660
taccagagag aatccgaggc ttattaccaa agaggggcaa gtgtgatcct cttctcctcc 720
cctcctgtga tcctcctcat ctctttcctc atttttctca tagtaggata g 771

<210> SEQ ID NO 11
<211> LENGTH: 762
<212> TYPE: DNA
<213> ORGANISM: Homo sapiens

<400> SEQUENCE: 11
atggcgaacc ttggctgctg gatgctggtt ctctttgtgg ccacatggag tgacctgggc 60
ctctgcaaga agcgcccgaa gcctggagga tggaacactg gggggcagccg atacccgggg 120
cagggcagcc ctggaggcaa ccgctaccca cctcagggcg gtggtggctg gggcagcct 180
catggtggtg gctgggggga gcctcatggt ggtggctggg ggcagcccca tggtggtggc 240
tggggacagc ctcatggtgg tggctggggt caaggaggtg gcacccacag tcagtggaac 300
aagccgagta agccaaaaac caacatgaag cacatggctg gtgctgcagc agctggggca 360
gtggtggggg gccttggcgg ctacatgctg ggaagtgcca tgagcaggcc catcatacat 420
ttcggcagtg actatgagga ccgttactat cgtgaaaaca tgcaccgtta ccccaaccaa 480
gtgtactaca ggcccatgga tgagtacagc aaccagaaca actttgtgcc tgactgcgtc 540
aatatcacaa tcaagcagca cacggtcacc acaaccacca agggggagaa cttcaccgag 600
accgacgtta agatgatgga gcgcgtggtt gagcagatgt gtatcaccca gtaggagagg 660
gaatctcagg cctattacca gagaggatcg agcatggtcc tcttctcctc tccacctgtg 720
atcctcctga tctctttcct catcttcctg atagtgggat ga 762

<210> SEQ ID NO 12
<211> LENGTH: 762
<212> TYPE: DNA
<213> ORGANISM: Homo sapiens

<400> SEQUENCE: 12
atggcgaacc ttggctgctg gatgctggtt ctctttgtgg ccacatggag tgacctgggc 60
ctctgcaaga agcgcccgaa gcctggagga tggaacactg gggggcagccg atacccgggg 120
cagggcagcc ctggaggcaa ccgctaccca cctcagggcg gtggtggctg gggcagcct 180
catggtggtg gctgggggca gccccatggt ggtggctggg ggcagcccca tggtggtggc 240
tggggacagc ctcatggtgg tggctggggt caaggaggtg gcacccacag tcagtggaac 300

-continued

```
aagctgagta agataaaaac caacatgaag cacatggctg gtgctgcagt ggctggggca    360

gtggtggggg gcgttggcgg ctacgtgctg gtaagtgcca tgagcaggcc catgatacat    420

ttcagcagtg actatgagga ccgttactat cgtgaaaaca tgcaccgtta ccccaaccaa    480

gtatactaca ggcccatgga tgagtacagc agccagaata actttgtgca taactgcatc    540

aatatcgcaa tcaagcagcg cggagtcacc acaaccacca aggggaagaa ctccaccaag    600

accaatatta agatgatgga gcatgtgatt cagccaatgt gtatcacccg gtagaagagg    660

gaatctcagg cctattacca gaggggatca agcagggtcc tcttctcctc ttcacctgtg    720

atcctcctga tctctttcct catcttcctg atagtgggat ga                        762


<210> SEQ ID NO 13
<211> LENGTH: 256
<212> TYPE: PRT
<213> ORGANISM: Artificial Sequence
<220> FEATURE:
<223> OTHER INFORMATION: Majority Sequence prepared to show the
      alignment of bovine, ovine, cervid, and human Prnp nucleotide
      sequences.

<400> SEQUENCE: 13

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Ser Asp Tyr Glu Asp Arg Tyr Tyr Arg Glu Asn Met His Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 14
<211> LENGTH: 264
<212> TYPE: PRT
```

<213> ORGANISM: Bos taurus

<400> SEQUENCE: 14

Met Val Lys Ser His Ile Gly Ser Trp Ile Leu Val Leu Phe Val Ala
1 5 10 15

Met Trp Ser Asp Val Gly Leu Cys Lys Lys Arg Pro Lys Pro Gly Gly
20 25 30

Gly Trp Asn Thr Gly Gly Ser Arg Tyr Pro Gly Gln Gly Ser Pro Gly
35 40 45

Gly Asn Arg Tyr Pro Pro Gln Gly Gly Gly Gly Trp Gly Gln Pro His
50 55 60

Gly Gly Gly Trp Gly Gln Pro His Gly Gly Gly Trp Gly Gln Pro His
65 70 75 80

Gly Gly Gly Trp Gly Gln Pro His Gly Gly Gly Trp Gly Gln Pro His
85 90 95

Gly Gly Gly Gly Trp Gly Gln Gly Gly Thr His Gly Gln Trp Asn Lys
100 105 110

Pro Ser Lys Pro Lys Thr Asn Met Lys His Val Ala Gly Ala Ala Ala
115 120 125

Ala Gly Ala Val Val Gly Gly Leu Gly Gly Tyr Met Leu Gly Ser Ala
130 135 140

Met Ser Arg Pro Leu Ile His Phe Gly Ser Asp Tyr Glu Asp Arg Tyr
145 150 155 160

Tyr Arg Glu Asn Met His Arg Tyr Pro Asn Gln Val Tyr Tyr Arg Pro
165 170 175

Val Asp Gln Tyr Ser Asn Gln Asn Asn Phe Val His Asp Cys Val Asn
180 185 190

Ile Thr Val Lys Glu His Thr Val Thr Thr Thr Thr Lys Gly Glu Asn
195 200 205

Phe Thr Lys Thr Asp Ile Lys Met Met Glu Arg Val Val Glu Gln Met
210 215 220

Cys Ile Thr Gln Tyr Gln Arg Glu Ser Gln Ala Tyr Tyr Gln Arg Gly
225 230 235 240

Ala Ser Val Ile Leu Phe Ser Ser Pro Pro Val Ile Leu Leu Ile Ser
245 250 255

Phe Leu Ile Phe Leu Ile Val Gly
260

<210> SEQ ID NO 15
<211> LENGTH: 264
<212> TYPE: PRT
<213> ORGANISM: Bos taurus

<400> SEQUENCE: 15

Met Val Lys Ser His Ile Gly Ser Trp Ile Leu Val Leu Phe Val Ala
1 5 10 15

Met Trp Ser Asp Val Gly Leu Cys Lys Lys Arg Pro Lys Pro Gly Gly
20 25 30

Gly Trp Asn Thr Gly Gly Ser Arg Tyr Pro Gly Gln Gly Ser Pro Gly
35 40 45

Gly Asn Arg Tyr Pro Pro Gln Gly Gly Gly Gly Trp Gly Gln Pro His
50 55 60

Gly Gly Gly Trp Gly Gln Pro His Gly Gly Gly Trp Gly Gln Pro His
65 70 75 80

Gly Gly Gly Trp Gly Gln Pro His Gly Gly Gly Trp Gly Gln Pro His
85 90 95

```
Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```

<210> SEQ ID NO 16
<211> LENGTH: 264
<212> TYPE: PRT
<213> ORGANISM: Bos taurus
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid

<400> SEQUENCE: 16

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Xaa Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Xaa Asp Tyr Glu Asp Arg Tyr
145                 150                 155                 160
```

```
Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260


<210> SEQ ID NO 17
<211> LENGTH: 264
<212> TYPE: PRT
<213> ORGANISM: Bos taurus

<400> SEQUENCE: 17

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```

-continued

<210> SEQ ID NO 18
<211> LENGTH: 256
<212> TYPE: PRT
<213> ORGANISM: Ovis canadensis

<400> SEQUENCE: 18

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255
```

<210> SEQ ID NO 19
<211> LENGTH: 264
<212> TYPE: PRT
<213> ORGANISM: Ovis aries

<400> SEQUENCE: 19

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
```

-continued

```
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260


<210> SEQ ID NO 20
<211> LENGTH: 256
<212> TYPE: PRT
<213> ORGANISM: Odocoileus virginianus

<400> SEQUENCE: 20

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Gly Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
```

```
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 21
<211> LENGTH: 256
<212> TYPE: PRT
<213> ORGANISM: cervus canadensis

<400> SEQUENCE: 21

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 22
<211> LENGTH: 265
<212> TYPE: PRT
<213> ORGANISM: Homo sapiens
<220> FEATURE:
<221> NAME/KEY: misc_feature
<222> LOCATION: (95)..(102)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
```

<400> SEQUENCE: 22

```
Met Ala Asn Ser His Leu Gly Cys Trp Met Leu Val Leu Phe Val Ala
1               5                   10                  15

Met Trp Thr Asp Leu Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Xaa Xaa
                85                  90                  95

Xaa Xaa Xaa Xaa Xaa Xaa Gly Gly Gly Thr His Ser Gln Trp Asn Lys
            100                 105                 110

Pro Ser Lys Pro Lys Thr Asn Met Lys His Met Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Ile Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Met Asp Glu Tyr Ser Asn Gln Asn Asn Phe Val His Asp Cys Val Asn
            180                 185                 190

Ile Thr Ile Lys Gln His Thr Val Thr Thr Thr Thr Lys Gly Glu Asn
        195                 200                 205

Phe Thr Glu Thr Asp Val Lys Met Met Glu Arg Val Val Glu Gln Met
    210                 215                 220

Cys Ile Thr Gln Tyr Glu Arg Glu Ser Gln Ala Tyr Tyr Gln Arg Gly
225                 230                 235                 240

Ser Ser Met Val Leu Phe Ser Ser Pro Pro Val Ile Leu Leu Ile Ser
                245                 250                 255

Phe Leu Ile Phe Leu Ile Val Gly Xaa
            260                 265
```

<210> SEQ ID NO 23
<211> LENGTH: 265
<212> TYPE: PRT
<213> ORGANISM: Homo sapiens
<220> FEATURE:
<221> NAME/KEY: misc_feature
<222> LOCATION: (95)..(102)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 23

```
Met Ala Asn Ser His Leu Gly Cys Trp Met Leu Val Leu Phe Val Ala
1               5                   10                  15

Thr Trp Ser Asp Leu Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
```

-continued

```
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Xaa Xaa
                85                  90                  95

Xaa Xaa Xaa Xaa Xaa Xaa Gly Gly Gly Thr His Ser Gln Trp Asn Lys
            100                 105                 110

Leu Ser Lys Ile Lys Thr Asn Met Lys His Met Ala Gly Ala Ala Val
        115                 120                 125

Ala Gly Ala Val Val Gly Gly Leu Gly Gly Tyr Val Leu Val Ser Ala
    130                 135                 140

Met Ser Arg Pro Met Ile His Phe Ser Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Met Asp Glu Tyr Ser Ser Gln Asn Asn Phe Val His Asn Cys Ile Asn
            180                 185                 190

Ile Thr Val Lys Gln Arg Gly Val Thr Thr Thr Thr Lys Gly Lys Asn
        195                 200                 205

Ser Thr Lys Thr Asn Ile Lys Met Met Glu His Val Ile Gln Pro Met
    210                 215                 220

Cys Ile Thr Arg Tyr Lys Arg Glu Ser Gln Ala Tyr Tyr Gln Arg Gly
225                 230                 235                 240

Ser Ser Arg Val Leu Phe Ser Ser Ser Pro Val Ile Leu Leu Ile Ser
                245                 250                 255

Phe Leu Ile Phe Leu Ile Val Gly Xaa
            260                 265


<210> SEQ ID NO 24
<211> LENGTH: 20
<212> TYPE: PRT
<213> ORGANISM: Bos taurus

<400> SEQUENCE: 24

Cys Ala Thr Ala Thr Gly Ala Thr Gly Cys Thr Gly Ala Cys Ala Cys
1               5                   10                  15

Cys Cys Thr Cys
            20


<210> SEQ ID NO 25
<211> LENGTH: 22
<212> TYPE: PRT
<213> ORGANISM: Bos taurus

<400> SEQUENCE: 25

Ala Gly Ala Ala Gly Ala Thr Ala Ala Thr Gly Ala Ala Ala Ala Cys
1               5                   10                  15

Ala Gly Gly Ala Ala Gly
            20


<210> SEQ ID NO 26
<211> LENGTH: 20
<212> TYPE: DNA
<213> ORGANISM: Bos taurus

<400> SEQUENCE: 26

catatgatgc tgacaccctc                                                  20
```

-continued

```
<210> SEQ ID NO 27
<211> LENGTH: 22
<212> TYPE: DNA
<213> ORGANISM: Bos taurus

<400> SEQUENCE: 27

agaagataat gaaaacagga ag                                              22
```

POLYMORPHISM IN BOVINE PRION PROTEIN GENE SEQUENCE

CROSS-REFERENCE TO RELATED APPLICATION

This application hereby claims the benefit of U.S. provisional application 60/793,760, filed Apr. 21, 2006, the content of which are incorporated by reference herein.

BACKGROUND OF THE INVENTION

1. Field of the Invention

The invention relates to a method for detecting genetic variations in bovine which influence their susceptibility to bovine spongiform encephalopathy.

Transmissible spongiform encephalopathy (TSE) agents or prions induce fatal neurodegenerative diseases in humans and in other mammalian species. They are transmissible among their species of origin, but they can also cross the species barrier and induce infection and/or disease in other species. Human TSEs include Creutzfeldt-Jakob disease (CJD), Gerstmann-Sträussler-Scheinker syndrome, Kuru and fatal familial insomnia (36). In animals, 4 distinct TSE diseases are recognized: scrapie in sheep and goats, transmissible mink encephalopathy (TME) in mink, chronic wasting disease (CWD) in cervids, and bovine spongiform encephalopathy (BSE) in cattle. BSE was transmitted via BSE-contaminated feed to cats (feline spongiform encephalopathy, FSE) and exotic ungulates (exotic ungulate encephalopathy, EUE) and via contaminated food to humans (48, 49, Smith et al., 2004. CTMI 284: 161). BSE first emerged in the United Kingdom in 1986, and has subsequently spread to many countries, predominantly in Western Europe. These outbreaks, caused by the consumption of infected meat and bone meal containing a malformed protein, have resulted in the destruction of thousands of cattle and have caused significant economic losses.

2. Description of the Prior Art

Prions are proteinaceous infectious particles and are the causative agents of TSEs. They are host coded proteins that have undergone conformational changes and have biological and physicochemical characteristics that differ significantly from those of other infectious agents. For example, they are resistant to inactivation processes that are effective against conventional viruses including those that alter nucleic acid structure or function. These include ionizing and UV radiation (1) or inactivation by formalin (20). In addition, infectivity is highly susceptible to procedures that modify protein conformation. Protein denaturants are effective at reducing infectivity titers but complete inactivation requires extremely harsh conditions, such as up to 4 hours of autoclaving at 134° C. or treatment with 2 N NaOH (39). In TSE disease, the normal cellular protein, $PrP^C$, is converted to abnormal prion protein, $PrP^{Sc}$. $PrP^{Sc}$ exhibits increased beta sheet content, a change that may drive the additional changes in solubility and protease resistance (38). Unlike normal cellular protein, $PrP^{Sc}$ is relatively insoluble in detergents, is relatively resistant to proteases (37) and is capable of causing a conformational change in additional molecules of $PrP^c$. The precise function of the normal $PrP^c$ in healthy animals remains unknown. $PrP^c$ might play a role in sleep physiology, in resistance to oxidative stress, in signal transduction and in self-renewal of hematopoietic stem cells (16, 29, 31, 53).

TSE disease involves the accumulation of $PrP^{Sc}$ in the central nervous system (CNS) of the host, eventually leading to neurodegeneration and disease. In TSE-affected animals, $PrP^c$ has a determinant role in the incubation time and species barrier (8). Transgenic mice lacking prion protein gene (Prnp) expression are not susceptible to TSE agents or prion infection, demonstrating the key role of PrP in TSEs (8). Susceptibility to prions thus depends upon the presence of $PrP^c$ on the cell membrane of the host; prions do not propagate in brains that lack $PrP^c$ (6).

Widely referred to as "mad cow disease", BSE was first identified as a TSE of cattle in the mid 1980s in the U.K. and more than 180,000 positive cases have been diagnosed in the U.K. to date. BSE is a chronic degenerative disease affecting the central nervous system of cattle. Affected animals display changes in temperament, abnormal posture, incoordination and difficulty in rising, decreased milk production, and/or loss of body weight despite continued appetite (40). The average incubation period is about 4-6 years and all affected animals succumb to the disease (28). Following the onset of clinical signs, the animal's condition deteriorates until it either dies or is destroyed. This process usually takes from 2 weeks to 6 months. Most cases in Great Britain occurred in dairy cows between 3 and 6 years of age with the highest susceptibility to infection being in the first 6 months of life; adult cattle are at relatively low risk of infection (3).

Using epidemiological surveillance programs, many European and non-European countries have discovered BSE-positive animals within the last decade (17, 34). Validated diagnostic tests for BSE require brain tissue (33, 47). There are no validated ante mortem tests for BSE available at present. The original diagnostic test method was histopathology in which sections of brain were examined under a microscope, and the classical vacuoles and spongiform changes in specific areas of the brain would allow a diagnosis (33). In the mid-1990s, immunohistochemistry (IHC) and Western blotting were developed which allowed the detection of $PrP^{Sc}$ in tissues (33). Both IHC and Western blot are considered confirmatory tests for BSE by the World Organization for Animal Health-OIE (33). In the past decade, so-called "rapid tests" have been introduced commercially for BSE surveillance (33).

However despite these and other advances, the need remains for improved methods for diagnosing BSE infected animals, and particularly for detecting bovine animals having increased susceptibility to BSE.

SUMMARY OF THE INVENTION

I have now discovered a specific, non-synonymous single nucleotide polymorphism (SNP) in the gene encoding bovine prion protein (Prnp) which might affect the susceptibility of bovine animals to bovine spongiform encephalitis (BSE). The precise location of the SNP varies with the number of octapeptide repeat sequences present in the Prnp gene. The octapeptide region polymorphisms result in encoded PrP proteins of different amino acid length. There are three known sequences of the bovine Prnp gene, those with five, six or seven of the octapeptide repeat units. Although six octapeptide repeat units are present in the Prnp gene of most bovines, a relatively small number of bovine possess Prnp genes having five octapeptide repeat units, and on rare occasions, bovine possessing Prnp genes having seven octapeptide repeat units have been observed. The SNP of this invention corresponds to position 322 nucleotides downstream from last nucleotide of the 3' end of the last octapeptide repeat region of the bovine Prnp sequence. This is equivalent to a net distance of 321 nucleotides between the last nucleotide of the last octapeptide repeat region and the SNP nucleotide (occurring in the 5' to 3' direction, i.e. in the bovine Prnp gene with 6 octapeptide repeat regions [e.g., GenBank Accession no.

AJ298878, (SEQ. ID. No. 1)], the last nucleotide at the 3' end of the $6^{th}$ octapeptide repeat region is at nucleotide position 309 and the SNP mutation at nucleotide position 631) on exon 3 of the Prnp gene, wherein the nucleotide position of the SNP is measured relative to the Prnp sequence, GenBank Accession no. AJ298878, disclosed by Coulthart and coworkers (12) the contents of which are incorporated by reference herein. Thus, depending on the number of octapeptide repeat units present in the Prnp gene, the position of the SNP is either nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences.

Alleles of the bovine Prnp wherein the codons 203, 211 or 219, respectively, with the nucleotide Adenine (A) at the SNP position encode lysine (K) at the corresponding amino acids (i.e., 211, 203 or 219) in the bovine prion protein (PrP), are all indicative of increased susceptibility to BSE in comparison to alleles of the bovine Prnp wherein the codons 203, 211 or 219, respectively, with the nucleotide Guanine (G) at the SNP position encode glutamic acid (E) at the same position. This SNP (nucleotide position 631 in Prnp gene with 6 octapeptide repeat region according to GenBank Accession no. AJ298878) may be used as a marker for selecting bovines susceptible to BSE for disposal and/or removal from breeding.

In accordance with this discovery, it is an object of this invention to determine an SNP in the Prnp gene in bovine which effects susceptibility to BSE.

It is also an object of this invention to provide methods for identifying this SNP in the Prnp gene in bovine which effects susceptibility to BSE.

In accordance with this discovery, it is an object of this invention to provide methods for identifying bovine exhibiting the trait of increased susceptibility to BSE.

Another object of this invention is to provide methods for screening bovine to select for those animals which possess alleles of the Prnp gene that are associated with increased susceptibility to BSE.

Other objectives and advantages of this invention will become readily apparent from the ensuing description.

BRIEF DESCRIPTION OF THE DRAWINGS

FIG. 1 A shows the alignment of bovine, ovine, cervid and human Prnp nucleotide sequences including BSE case B14842 as described in Example 1 (SEQ. ID. Nos. 2-12). All bovine alleles contained six octapeptide repeat units, while the ovine, cervid and human PrnP alleles contained five octapeptide repeat units. The box enclosing nucleotides 283-306 (codons 95-102) represents the additional octapeptide-repeat region in bovine (for a total of six octapeptide repeats) which is not present in ovine and cervids. The box surrounding nucleotides 631-633 represents the codon where the non-synonymous polymorphism ("G"AA/"A"AA) is located in the first position of bovine codon 211 of BSE case B14842. Standard single letter codes are used for nucleotides. Y=C or T; R=A or G; K=G or T; W=A or T.

FIG. 1B shows the amino acid sequences for the corresponding prion protein encoded by the Prnp gene sequences depicted in FIG. 1A (SEQ. ID: Nos. 13-23). Standard IUPAC single letter codes are used for amino acids. The box surrounding codon 211 represent the codon with the E211K polymorphism.

Codon numbering refers to the most common six-copy octapeptide repeat allele for *Bos Taurus* as described by Coulthart and coworkers (12). The following bovine, cervid, ovine and human GenBank entries were used for the alignments: BSE Case B14842, and GenBank accession numbers AY335912 (bovine: reports Prnp coding variation in a panel of 96 cattle chosen to represent most of the genetic diversity of the beef cattle breeds most commonly raised in North America), CAN_BSE=Canadian 2003 BSE case (see Coulthart et al., 2003; citation 12), AY335912 (bovine), AY367641 (bovine), AF166334 (ovine), AY275712 (white-tailed deer), and AF016227 (elk). The human sequences were derived from FIG. 1 in Coulthart et al., 2003 (12). Human 1=M13899; Human 2=PRNPvar.

DEFINITIONS

Allele: the term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. In a haploid set of chromosomes there is only one allele at its specific locus. Diploid organisms have 2 alleles at a given locus, and if they are homozygous for a defined gene, both alleles are identical. However, if heterozygous for a defined gene they have one normal and one mutant allele. A single allele for each gene locus is inherited separately from each parent (e.g., at a locus for eye color the allele might result in blue or brown eyes). An organism is homozygous for a gene if the alleles are identical, and heterozygous if they are different. (Birgid Schlindwein's Hypermedia Glossary of Genetic Terms).

Amplicon: a term to define the amplification product generated by the polymerase chain reaction. The physical boundaries of an amplicon extend to the base sequence at the 5' ends of each of a pair of primers (short, 18-20 oligonucleotides) in the reaction.

Centimomorgan (cM): a unit to measure the recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs. (Birgid Schlindwein's Hypermedia Glossary of Genetic Terms).

Crossing over: the term coined by Morgan and Cattell (1912) for the occurrence of new combinations of linked characters. With the acceptance of the chromosome theory, the term is applied to the breaking during meiosis of one maternal and one paternal chromosome, the exchange of corresponding sections of DNA, and the rejoining of the chromosomes. This process can result in an exchange of alleles between chromosomes and gives rise to new character combinations. (Birgid Schlindwein's Hypermedia Glossary of Genetic Terms).

DNA or RNA sequence: a linear series of nucleotides connected one to the other by phosphodiester bonds between the 3' and 5' carbons of adjacent pentoses.

Genotype: the term proposed by Johannsen (1909) for the hereditary constitution of an individual, or of particular nuclei within its cells. (Birgid Schlindwein's Hypermedia Glossary of Genetic Terms).

Identity by descent: two alleles at a single locus are identical by descent if there are identical copies of the same allele in some earlier generation, i.e., both are copies that arose by DNA replication from the same ancestral sequence without any intervening mutation. The animal is homozygous for this defined locus.

Identity by type: two alleles at a single locus are identical by type, (i.e. "the same") if they have the same phenotypic effects.

Locus: the position of a gene on a chromosome or other chromosome markers; also, the DNA at that position. The use of the term locus is sometimes restricted to main regions of DNA that are expressed. (Birgid Schlindwein's Hypermedia Glossary of Genetic Terms).

Marker: an identifiable physical location on a chromosome (e.g., restriction enzyme cutting site, gene, minisatellite, microsatellite) whose inheritance can be monitored. Markers can be expressed regions of DNA (genes) or some segment of DNA with no known coding function but whose pattern of inheritance can be determined. (Birgid Schlindwein's Hypermedia Glossary of Genetic Terms).

Nucleic acid: a deoxyribonucleotide or ribonucleotide polymer in either single- or double-stranded form, including known analogs of natural nucleotides unless otherwise indicated.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide: a single-stranded nucleic acid ranging in length from 2 to about 500 bases, usually 2-100 bases.

Phenotype: the term coined by Johannsen (1909) for the appearance (Gk. phainein, to appear) of an organism with respect to a particular character or group of characters (physical, biochemical, and physiologic), as a result of the interaction of its genotype and its environment. Often used to define the consequences of a particular mutation. (Birgid Schlindwein's Hypermedia Glossary of Genetic Terms).

Polymorphic marker or site: the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms (U.S. Pat. No. 6,368,799).

Probe: a DNA fragment or an oligonucleotide capable of binding to a target nucleic acid of complementary sequence through one or more types of chemical bonds, by hybridization or complementary base pairing, usually through hydrogen bond formation. Oligonucleotides probes are often 10-50 or 15-30 bases long. An oligonucleotide probe may include natural (i.e. A, G, C, or T) or modified bases (7-deazaguanosine, inosine, etc.).

Recombination: the process by which progeny derive a combination of linked genes different from that of either parent. In higher organisms, this can occur by crossing over between their loci during meiosis. Recombination may come about through random orientation of non-homologous chromosome pairs on the meiotic spindles, from crossing-over between homologous chromosomes, from gene conversion, or by other means. (Birgid Schlindwein's Hypermedia Glossary of Genetic Terms).

Single nucleotide polymorphism (SNP): occurrence of a polymorphic site occupied by a single nucleotide, constituting the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site.

Specific hybridization: binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. A perfectly matched probe has a sequence perfectly complementary to a particular target sequence (U.S. Pat. No. 6,368,799).

Transition: the term proposed by Freese (1959) for a mutation caused by the substitution in DNA or RNA of one purine by the other, and similarly with the pyrimidines. (Birgid Schlindwein's Hypermedia Glossary of Genetic Terms).

Transversion: the term proposed by Freese (1959) for a mutation caused by the substitution of a purine for a pyrimidine, and vice versa, in DNA or RNA. (Birgid Schlindwein's Hypermedia Glossary of Genetic Terms).

DETAILED DESCRIPTION OF THE INVENTION

The entire exon 3 (coding region for the bovine prion protein) of the bovine PrnP gene was amplified by PCR from animal B14842 and has been sequenced. The nucleotide sequence and the corresponding amino acid sequence are shown in SEQ. ID. Nos. 3 and 14.

Prion protein gene alleles containing a variety of polymorphisms have been associated with increased susceptibility to TSE in sheep and humans (28A, 32A). However, to date, polymorphisms effecting susceptibility to BSE have not been identified in exon 3, the coding region of bovine Prnp. So far, only certain polymorphisms described in the promoter region of the bovine Prnp gene have been associated with increased or reduced susceptibility to BSE (12, 23, 41). Upon Prnp gene sequence analysis of a recently diagnosed BSE case, designated animal B14842, I have discovered a previously unknown non-synonymous polymorphism within the Prnp gene coding sequence from this animal. One Prnp gene allele of the animal contained an SNP designated E211K (GAA/AAA) at nucleotides 631-633 (codon 211) in the 6 octapeptide repeat region containing bovine Prnp gene as described by Coulthart and coworkers (12). As previously described in the art, normal bovine possess coding sequences for the Prnp gene which include six octapeptide repeat regions and guanine at position 631. The resultant 211 codon is GAA, encoding glutamic acid (E) at amino acid 211 of the prion protein. However, the BSE positive B14842 animal possessed an SNP at position 631 substituting adenine for guanine, and the Prnp gene codon 211 is AAA and consequently encodes the basic amino acid lysine (K) rather than the acidic amino acid glutamic acid (E).

It is believed that the presence of this SNP is associated with a case of genetic BSE in bovine B14842 and older animals carrying this SNP and such a SNP may increase the susceptibility of younger animals to BSE. Moreover, while a polymorphism for codon 211 has not been previously described for the bovine Prnp gene, a non-synonymous polymorphism at the corresponding codon 200 in the human Prnp gene (E200K; GAG/AAG) is well known. This E200K mutation has been shown to lead to genetic TSE's in humans (>50% of individuals carrying the E200K polymorphism develop a human genetic TSE when advanced in age (see review by Kovacs et al., 2005; 28A), and is the most common mutation in human patients with genetic Creutzfeldt-Jakob disease (gCJD), fatal familial insomnia (FFI), and Gerstmann-Straussler-Scheinker (GSS) disease (28A). Considering that the human Prnp gene possesses only five octapeptide repeat units vs. the typical six in the bovine (and also in the B14842 animal) Prnp gene, and that the human Prnp gene has three codon deletions in its N-terminus as compared to the bovine Prnp, the E211K SNP of the invention is homologous to the E200K SNP described for the human Prnp gene. This finding indicates that genetic BSE or gBSE could exist in cattle similar to the genetic prion diseases or gTSE described in humans (28A).

While the SNP of this invention was discovered in a bovine possessing a Prnp gene having the typical six octapeptide metal-binding repeat units, there are two other known bovine Prnp gene sequences with five and seven of the octapeptide repeats. Thus, depending on the number of octapeptide repeat units present in the Prnp gene, the position of the SNP is either nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences. Because the SNP exists at homologous codon positions in the bovine Prnp gene, the SNP may be described relative to the position of the last octapeptide repeat nucleotide (measured from the 5' to 3' direction) on exon 3 of the Prnp gene. In the bovine Prnp gene with 6 octapeptide repeat regions (GenBank Accession no. AJ298878), the last nucleotide at the 3' end of the $6^{th}$ octapeptide repeat region is at nucleotide position 309 and the SNP mutation at nucleotide position 631 on exon 3 of the Prnp gene. The nucleotide position of the SNP is measured relative to the Prnp sequence, GenBank Accession no. AJ298878, disclosed by Coulthart and coworkers (12) the contents of which are incorporated by reference herein. In bovine possessing a Prnp gene having five, six or seven octapeptide repeat units on exon 3, the last (i.e., on the 3' end) nucleotide of the last ($5^{th}$, or $6^{th}$ or $7^{th}$) octapeptide repeat region sequence is at nucleotide position 285, 309, and 333, respectively. Consequently, the SNP of this invention corresponds to a position 322 nucleotides downstream from this nucleotide at the 3' end of the last octapeptide repeat sequence. For the purposes of this invention, it is understood that the nucleotide position of the final 3' nucleotide of the last octapeptide repeat region ($5^{th}$, $6^{th}$ or $7^{th}$), and thus the nucleotide position of the SNP, is measured relative to the Prnp sequence, GenBank Accession no. AJ298878, disclosed by Coulthart and coworkers (12). It is also understood that animals which are either heterozygous or homozygous for the SNP of this invention (the E211K mutation) may exhibit increased susceptibility to BSE.

This invention is also drawn to a method for determining alleles of the bovine Prnp gene encoding prion protein (the amino acid sequence of which is shown in FIG. 1B) which affects the susceptibility of bovines to BSE. In accordance with this method, a sample of nucleic acids from a bovine is assayed to determine the nucleotides present at the SNP in the Prnp gene which is disclosed herein. As noted above, the position of the SNP is either nucleotide 631 of exon 3 (codon 211) when the Prnp gene comprises six octapeptide repeat region sequences, nucleotide 607 of exon 3 (codon 203) when the Prnp gene comprises five octapeptide repeat region sequences, or nucleotide 655 of exon 3 (codon 219) when the Prnp gene comprises seven octapeptide repeat region sequences.

Because the polymorphism occurs at homologous codons on the Prnp gene, the codon containing the SNP may encode either glutamic acid (E) or lysine (A) at the corresponding amino acids 203, 211 or 219 of the bovine prion protein (for prion protein encoded by Prnp genes having five, six or seven octapeptide repeat units, respectively). Specifically, the above-mentioned SNP at positions 607, 631 or 655 may be guanine, yielding a "G"AA codon encoding glutamic acid (E), or the SNP may be adenine, yielding an "A"AA codon encoding lysine (K). It is believed that alleles of the bovine Prnp wherein the SNP at these positions encode lysine at the corresponding amino acids (i.e., 211, 203 or 219) in the bovine prion protein, are all associated with increased susceptibility to BSE in comparison to alleles which encode glutamic acid (E) at the same position (as the latter is typically present in normal, healthy bovine). This SNP may be used as a marker for selecting bovines with a higher susceptibility to BSE for disposal and/or removal from breeding.

The SNP's may be detected by assaying for the presence of the above-mentioned nucleotides in a sample of nucleic acids from a subject bovine animal at the loci of the SNP, wherein the loci correspond to nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences. Suitable nucleic acids for use in the assay include genomic DNA, cDNA, or RNA, as well as nucleic acids that encompass, or are encompassed by the bovine Prnp gene sequences of FIG. 1 or the complement thereof, as well as bovine Prnp gene sequences which are the same as in FIG. 1 except for the presence of five or seven octapeptide repeat sequences or their complement. AS will be described in greater detail herein below, use of genomic DNA is preferred.

It is also envisioned that the SNP may also be detected by analysis of the encoded gene product, i.e., the amino acid sequence of prion protein in a sample obtained from the subject animal. Sample materials which may be collected from the animal for the assay include, but are not limited to, milk, blood, tissue, cells, urine, or other biological samples from the subject such as described by Novakofski et al (32A, the contents of which are incorporated by reference herein).

The presence of the allelic forms of the above-described SNP can be determined by any of a number of diagnostic assays. These assays may use otherwise known techniques, including direct sequencing of the nucleic acids in the sample, or using probes which overlap the position of the SNP's on those nucleic acids. For example, Arnold et al. (U.S. Pat. No. 6,410,231, herein incorporated by reference) is drawn to SNP detection by means of an array-based sandwich assay. Arnold et al. also makes mention of a variety of other techniques that had been previously developed for SNP detection and analysis; specifically: Sapolsky et al. (1999) U.S. Pat. No. 5,858, 659; Shuber (1997) U.S. Pat. No. 5,633,134; Dahlberg (1998) U.S. Pat. No. 5,719,028; Murigneux (1998) WO 98/30717; Shuber (1997) WO 97/10366; Murphy et al. (1998) WO 98/44157; Lander et al. (1998) WO 98/20165; Goelet et al. (1995) WO 95/12607 and Cronin et al. (1998) WO 98/30883. In addition, ligase based methods are described by Barany et al. (1997) WO 97/31256 and Chen et al. Genome Res. 1998; 8(5):549-556; mass-spectroscopy-based methods by Monforte (1998) WO 98/12355, Turano et al. (1998) WO 98/14616 and Ross et al. (1997) Anal. Chem. 15:4197-4202; PCR-based methods by Hauser, et al. (1998) Plant J. 16:117-125; exonuclease-based methods by Mundy U.S. Pat. No. 4,656,127; dideoxynucleotide-based methods by Cohen et al. WO 91/02087; Genetic Bit Analysis or GBA™ by Goelet et al. WO 92/15712; Oligonucleotide Ligation Assays or OLAs by Landegren et al. (1988) Science 241:1077-1080 and Nickerson et al. (1990) Proc. Natl. Acad. Sci. (USA) 87:8923-8927; and primer-guided nucleotide incorporation procedures by Prezant et al. (1992) Hum. Mutat. 1:159-164; Ugozzoli et al. (1992) GATA 9:107-112; Nyreen et al. (1993) Anal. Biochem. 208:171-175, all of which are incorporated herein by reference. Other potential assay techniques are described below. McCutchen-Maloney (U.S. Pat. No. 6,340, 566, herein incorporated by reference) teaches detection and quantification of SNP's, DNA sequence variations, DNA mutations, DNA damage and DNA mismatches using mutation binding proteins alone or as chimeric proteins with nucleases on solid supports. Also, Poponin (U.S. Pat. No. 6,376,177, herein incorporated by reference) teaches a method and apparatus for SNP detection by means of spectroscopic analysis of hybridized nucleic acid using high density nucleic acid chips. Numerous conventional assay techniques for detecting SNP's which are also suitable for use herein are described by Aguirre et al. (U.S. Pat. No. 6,428, 958) and Rothenberg (U.S. Pat. No. 6,355,425). The contents of each of the above-mentioned publications and patents are incorporated by reference herein.

In accordance with one preferred embodiment, the presence of the SNP is detected by PCR amplification as described in Example 1. It is envisioned that a variety of primers and PCR assays may be suitable for use in the amplification, including bovine Prnp specific primers disclosed by Heaton et al. (23), Sander et al. (41) or Coulthart et al (12), the contents of which are incorporated by reference herein. However, in a preferred embodiment, at least one of the primers is designed to hybridize to a region of the gene outside of exon 3, such as an intron (here intron 2). Although not reported in bovine to date, the recent disclosure of pseudogenes in cervidae (32A) raises the specter of their possible presence in genomes of other animals as well, including bovine. Because pseudogenes are non-functional, but heritable, genes believed to have been generated by reverse transcription of mRNA from previous generations of the species, they may have different nucleotide sequences than the corresponding functional gene in the subject animal of interest. Consequently, if pseudogenes are present, the possibility exists that primers generated strictly from the exons of a gene of interest may in fact be selective for the pseudogene rather than the active gene. To guard against the possible presence of any such pseudogenes, at least one of the primers used herein is preferably generated to bind to a region of the gene outside of the coding sequence of the genomic DNA, such an intron. In accordance with this embodiment, preferred primers for use herein include, but are not limited to 5'-CAT ATG ATG CTG ACA CCC TC-3' (SEQ. ID. No. 24) and 5'-AGA AGA TAA TGA AAA CAG GAA G-3' (SEQ. ID. No. 25), wherein the first primer is the intron 2-specific forward primer, and the second primer is the exon 3-specific reverse primer.

The presence of the SNP on exon 3 of the Prnp gene may also be detected by assaying for the same nucleotides described above at the loci corresponding to nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences, in an RNA molecule which is a transcript of a sequence encompassed by, or encompassing, the complementary strand to the bovine Prnp gene such as shown in FIG. 1. Alternatively, any of the SNP's may be detected in the DNA strand complementary to the sequence shown in FIG. 1 by assaying for the complementary nucleotides at the loci corresponding to position nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences.

As noted above, the SNP of the bovine Prnp gene may also be detected by analysis of the prion protein product. In bovine possessing a prion protein having five, six or seven octapeptide repeat units, the last (i.e., C-terminal) amino acid of the last (C-terminal) octapeptide region is at position 95, 103, and 111, respectively. Consequently, the SNP of this invention corresponds to a position 108 amino acids downstream from this amino acid at the C-terminal end of the last octapeptide repeat sequence. Again, for the purposes of this invention, it is understood that the amino acid position of the final C-terminal amino acid of the final C-terminal octapeptide region, and thus the amino acid position of the SNP, is measured relative to the prion protein sequence encoded by the Prnp sequence, GenBank Accession no. AJ298878, disclosed by Coulthart, 12. For example, the glutamic acid/lysine (E/K) amino acid substitution caused by the SNP at the above-identified positions may be identified by contacting the biological samples with immunolabelling agents, such as monoclonal or polyclonal antibodies, raised against the variant protein (i.e., the protein resulting from the Prnp gene with the aforementioned glutamic acid/lysine substitutions). Such antibodies may be obtained using standard techniques and may be polyclonal or monoclonal. Polyclonal antibodies can be obtained, for example, by the methods described in Ghose et al. (Methods in Enzymology. Vol. 93:326-327, 1983). A prion protein polypeptide, or an antigenic fragment thereof, is used as an immunogen to stimulate the production of prion protein reactive polyclonal antibodies in the antisera of animals such as rabbits, goats, sheep, rodents and the like. Anti-prion protein antibodies specific for Prnp gene products are raised by immunizing animals with a polypeptide spanning site of the variation (i.e., amino acids 203, 211 and/or 219). Monoclonal antibodies may be obtained by the process described by Milstein and Kohler (1975. Nature. 256:495-497) or as modified by Gerhard (Monoclonal Antibodies. Plenum Press. 1980.

pages 370-371). Hybridomas are screened to identify those producing antibodies that are highly specific for the selected prion protein immunogen, which is characteristic of increased or decreased susceptibility to BSE, i.e. specific for the E or K allele of the bovine Prnp gene.

Antibody binding may also be detected using known methods. For example, an ELISA assay utilizing a substrate (e.g., a plastic dish) coated with antigen comprising a bovine-derived biological sample containing the Prnp gene product. An antibody preparation specific for a known Prnp gene product is added to the well, whereupon the antibody will bind or fail to bind to the sample in the well. Non-binding material is washed away and a marker enzyme (e.g., horse radish peroxidase or alkaline phosphatase, coupled to a second antibody directed against the antigen-specific primary antibody) is added in excess and the nonadherent material is washed away. An enzyme substrate is added to the well and the enzyme catalyzed conversion is monitored as indicative of presence of the variant.

The SNP in the bovine Prnp gene of this invention may be used as a marker for identifying bovine animals having increased or reduced susceptibility to BSE. In a preferred embodiment, the SNP is used as a marker to select for cattle having the alleles associated with increased susceptibility to BSE (encoding lysine), and such animals would not be selected for breeding, may be prevented from use in the preparation of animal feed or human food products, and/or may be destroyed. In contrast, bovine possessing the SNP encoding glutamic acid may be selected for use in breeding programs to produce progeny which will also exhibit reduced susceptibility to BSE. While it is envisioned that the invention may be practiced with any species of Bovidae, and particularly any species of the genus *Bos*, it is preferably practiced with *Bos taurus* and *Bos indicus*, and particularly bulls, cows or calves.

The following examples are intended only to further illustrate the invention and are not intended to limit the scope of the invention which is defined by the claims.

Example 1

This example describes the identification and characterization of a recently diagnosed BSE case, bovine animal no. B14842. Western Blot analyses by the USDA-Agricultural Research Service-National Animal Disease Center confirmed that this animal was BSE positive.

Material and Methods

Animals and tissues. Brainstem tissue samples were taken from a bovine, animal no. B14842, suspected to be infected with BSE according to the USDA BSE surveillance plan.

Frozen samples from the medulla oblongata (obex) were available for analysis.

Western Blot Analyses. Brain homogenates from this BSE case were prepared and analyzed using the OIE-recommended Scrapie Associated Fibril (SAF)-Immunoblot method with minor modifications. This method enriches brain samples for $PrP^{Sc}$ by ultracentrifugation prior to loading them onto a SDS-PAGE gel. The SDS-PAGE electrophoresis conditions, subsequent transfer and immunodetection of $PrP^{res}$ were carried out as described elsewhere (Hamir et al, 2006. Vet Pathol. 43: 118-126). Therefore, only the enrichment method will be described in more detail. Material for analysis was taken from the brainstem area and cut into small pieces with a new razor blade after removal of dura mater. A 10% (w/v) tissue homogenate in 10 mM Tris, pH 7.5, containing 5 mM $MgCl_2$ was prepared using a homogenizer with a disposable probe (5 times, 30 sec). The homogenate was mixed well and then again sonicated for 30 seconds on ice bath (5-10 times). Benzonase® was added to the mixture for a final concentration of 100 Units/ml and incubated for 1 h at 37° C. while shaking. An equal volume of 20% (w/v) N-Lauroylsarcosine$^{m}$ in 10 mM Tris, pH 7.5 and 1 mM DTT was added to each homogenate, vortexed for 1 min every 10 min for a total of 30 min at room temperature. Homogenates were transferred to polyallomer tubes and centrifuged at 20,000×g for 25 min at 10° C. Supernatant was centrifuged again using polyallomer tubes$^{n}$ at 200,000×g for 55 min at 10° C. The resultant supernatant was discarded, the pellet was resuspend in sterile, distilled $H_2O$ (1 μl per mg tissue equivalent) and sonicated until suspended. Sample was split into two aliquots into microcentrifuge tubes and one sample was treated with PK (concentration 0.4 Units/ml) by incubation at 37° C. for 60 min with agitation while the control sample was not treated with PK. Phenylmethylsulphonyl fluoride (PMSF) was added to a final concentration of 5 mM, incubated on ice for 15 min and transferred to a new 1.5 ml ultracentrifuge tube. Volume was brought up to 500 μl with $H_2O$ and centrifuged at 200,000×g for 1 hr at 10° C. Pellet was resuspended in SDS-PAGE sample buffer to at least 10 mg tissue equivalent per μl. Samples were sonicated on wet ice before loading on SDS-PAGE gel. For both Western Blot techniques, detection was performed either on Biomax films or scanned images were obtained with a Typhoon imaging system.

DNA isolation and PCR amplification. Genomic DNA was extracted from 200 μl of a 10% brain homogenate using the DNeas™ tissue kit (Qiagen) according to the manufacturer's instructions. PCR was performed in a 100 μl final reaction volume containing 0.2 pmole of forward primer (5'-CAT ATG ATG CTG ACA CCC TC-3'), 0.2 pmol of reverse primer (5'-AGA AGA TAA TGA AAA CAG GAA G-3') 1× Easy-A PCR buffer, 2.5 mM $MgCl_2$, 0.8 mM each deoxyribonucleotide triphosphate (dNTP Master Mix, 2.5 U of Easy-A™ high-fidelity cloning Taq DNA polymerase, and 0.4 ug of total DNA. Amplification was performed with the following conditions: 94° C. for 5 min, followed by 30 Cycles of 94° C. for 30 sec (denaturation), 59° C. for 30 sec (annealing), and 72° C. for 1 min. A final extension step at 72° C. was performed for 10 minutes. Amplified DNA product was purified using a GENECLEAN® spin kit$^{u}$ and sequencing was performed using the ABI 3700 DNA sequencer with a cycle sequencing kit. The fragment was sequenced in duplicate using the original two primers and two internal primers 4142 and 9612 for a total of 8 reactions. Databases were searched using standard nucleotide-nucleotide BLAST at the National Center for Biotechnology Information Web Site. The database is a collection of sequences from several sources, including GenBank and Reference Sequence. The nucleotide sequence of the BSE case was aligned using both CLUSTAL V[24,25] and CLUSTAL W[46] with the following GENBANK accession numbers: AY335912 (bovine), AY367641 (bovine), AF016227 (elk), AY275712 (white-tailed deer), AF166334 (ovine), and the Canadian BSE case using Lasergene version 5.07 software (DNASTAR-Madison, Wis.).

Results

Western Blot Analysis.

Western blot analysis of brainstem homogenate of the BSE case revealed a definite positive reaction. All three isoforms of $PrP^{Sc}$ were definitely present at the milligram brain tissue equivalent tested.

Analysis of the Prnp.

In order to confirm the material from the BSE case was derived from cattle and to determine whether the BSE case of the affected animals might be associated with a spontaneous germline mutation, the full coding sequence from exon 3 of the Prnp was amplified and aligned with known PrP sequences from cattle, sheep and cervids. DNA was isolated from fresh brainstem material. The prion protein (PrP) alleles of animal B14842 were found to have two polymorphisms, a synonymous polymorphism Q78Q (CAA/CAG) at codon 78 (as described in Genbank submission AY335912), and a non-synonymous polymorphism E211K (GAA/AAA) at codon 211 and both alleles contained the six-copy octapeptide repeat region. A polymorphism for position 211 has not been described for the cattle prion protein gene so far, but a non-synonymous polymorphism at the same codon, designated codon 200 in the human prion protein gene (Prnp) has been described previously (E200K; GAG/AAG). The E200K mutation is the most common mutation in human patients with genetic Creutzfeldt-Jakob Disease (gCJD), fatal familial insomnia (FFI) and Gerstmann-Sträussler-Scheinker (GSS) disease (Kovacs et al., 2005, *Hum. Genet*, 118, 166-174).

It is understood that the foregoing detailed description is given merely by way of illustration and that modifications and variations may be made therein without departing from the spirit and scope of the invention.

REFERENCES

1 Alper T, Haig D A, Clarke M C: 1966, The exceptionally small size of the scrapie agent. Biochem Biophys Res Commun 22:278-284.

2 Anderson R M, Donnelly C A, Ferguson N M, et al.: 1996, Transmission dynamics and epidemiology of BSE in British cattle. Nature 382:779-788.

3 Arnold M E, Wilesmith J W: 2004, Estimation of the age-dependent risk of infection to BSE of dairy cattle in Great Britain. Prey Vet Med 66:35-47.

4 Baylis M, Houston F, Goldmann W, et al.: 2000, The signature of scrapie: differences in the PrP genotype profile of scrapie-affected and scrapie-free UK sheep flocks. Proc Biol Sci 267:2029-2035.

5 Biacabe A G, Laplanche J L, Ryder S, Baron T: 2004, Distinct molecular phenotypes in bovine prion diseases. EMBO Rep 5:110-115.

6 Brandner S, Isenmann S, Raeber A, et al.: 1996, Normal host prion protein necessary for scrapie-induced neurotoxicity. Nature 379:339-343.

6A Brayton K A et al.: 2004, A processed pseudogene contributes to apparent mule deer prion gene heterogeneity. Gene 326:167-173.

7 Bruce M E, Will R G, Ironside J W, et al.: 1997, Transmissions to mice indicate that 'new variant' CJD is caused by the BSE agent. Nature 389:498-501.

8 Bueler H, Aguzzi A, Sailer A, et al.: 1993, Mice devoid of PrP are resistant to scrapie. Cell 73:1339-1347.

9 Cardone F, Liu Q G, Petraroli R, et al.: 1999, Prion protein glycotype analysis in familial and sporadic Creutzfeldt-Jakob disease patients. Brain Res Bull 49:429-433.

10 Casalone C, Zanusso G, Acutis P, et al.: 2004, Identification of a second bovine amyloidotic spongiform encephalopathy: molecular similarities with sporadic Creutzfeldt-Jakob disease. Proc Natl Acad Sci USA 101:3065-3070.

11 Colchester A C, Colchester N T: 2005, The origin of bovine spongiform encephalopathy: the human prion disease hypothesis. Lancet 366:856-861.

12 Coulthart M B, Mogk R, Rancourt J M, et al.: 2003, Prion protein gene sequence of Canada's first non-imported case of bovine spongiform encephalopathy (BSE). Genome 46:1005-1009.

13 Cutlip R C, Miller J M, Lehmkuhl H D: 1997, Second passage of a US scrapie agent in cattle. J Comp Pathol 117:271-275.

14 De Bosschere H, Roels S, Vanopdenbosch E: Atypical Case of Bovine Spongiform Encephalopathy in an East-Flemish Cow in Belgium. The International Journal of Applied Research in Veterinary Medicine 2:52-55.

15 Gambetti P, Kong Q, Zou W, et al.: 2003, Sporadic and familial CJD: classification and characterisation. Br Med Bull 66:213-239.

16 Gauczynski S, Peyrin J M, Haik S, et al.: 2001, The 37-kDa/67-kDa laminin receptor acts as the cell-surface receptor for the cellular prion protein. Embo J 20:5863-5875.

17 Giovannini A, Savini L, Conte A, Fiore G L: 2005, Comparison of BSE prevalence estimates from EU countries for the period July to December 2001 to the OIE and EU GBR classifications. J Vet Med B Infect Dis Vet Public Health 52:262-271.

18 Goldmann W, Hunter N, Foster J D, et al.: 1990, Two alleles of a neural protein gene linked to scrapie in sheep. Proc Natl Acad Sci USA 87:2476-2480.

19 Goldmann W, Hunter N, Smith G, et al.: 1994, PrP genotype and agent effects in scrapie: change in allelic interaction with different isolates of agent in sheep, a natural host of scrapie. J Gen Virol 75 (Pt 5):989-995.

20 Gordon W S: 1946, Advances in Veterinary Research. Veterinary Research 58:516-520.

21 Hamir A N, Cutlip R C, Miller J M, et al.: 2001, Preliminary findings on the experimental transmission of chronic wasting disease agent of mule deer to cattle. J Vet Diagn Invest 13:91-96.

22 Hamir A N, Kunkle R A, Cutlip R C, et al.: 2005, Experimental transmission of chronic wasting disease agent from mule deer to cattle by the intracerebral route. J Vet Diagn Invest 17:276-281.

23 Heaton M P, Leymaster K A, Freking B A, et al.: 2003, Prion gene sequence variation within diverse groups of U.S. sheep, beef cattle, and deer. Mamm Genome 14:765-777.

24 Higgins D G, Sharp P M: 1988, CLUSTAL: a package for performing multiple sequence alignment on a microcomputer. Gene 73:237-244.

25 Higgins D G, Sharp P M: 1989, Fast and sensitive multiple sequence alignments on a microcomputer. Comput Appl Biosci 5:151-153.

26 Hill A F, Desbruslais M, Joiner S, et al.: 1997, The same prion strain causes vCJD and BSE. Nature 389:448-450, 526.

27 Hunter N, Goldmann W, Smith G, Hope J: 1994, Frequencies of PrP gene variants in healthy cattle and cattle with BSE in Scotland. Vet Rec 135:400-403.

28 Kimberlin R H: 1993, Bovine spongiform encephalopathy: an appraisal of the current epidemic in the United Kingdom. Intervirology 35:208-218.

28A Kovacs G G et al: 2005, Genetic prion disease: the EUROCJD experience. Hum Genet 118:166-174.

29 Milhavet O, Lehmann S: 2002, Oxidative stress and the prion protein in transmissible spongiform encephalopathies. Brain Res Brain Res Rev 38:328-339.

30 Miller J M, Jenny A L, Taylor W D, et al.: 1994, Detection of prion protein in formalin-fixed brain by hydrated autoclaving immunohistochemistry for the diagnosis of scrapie in sheep. J Vet Diagn Invest 6:366-368.

31 Mouillet-Richard S, Ermonval M, Chebassier C, et al.: 2000, Signal transduction through prion protein. Science 289:1925-1928.

32 Neibergs H L, Ryan A M, Womack J E, et al.: 1994, Polymorphism analysis of the prion gene in BSE-affected and unaffected cattle. Anim Genet 25:313-317.

32A Novakofski J et al.: 2005, Prion biology relevant to bovine spongiform encephalopathy. J Anim Sci 83:1455-1476.

34 Onodera T, Kim C K: 2006, BSE situation and establishment of Food Safety Commission in Japan. J Vet Sci 7:1-11.

35 Parchi P, Gambetti P: 1995, Human prion diseases. Curr Opin Neurol 8:286-293.

36 Prusiner S B: 1998, The prion diseases. Brain Pathol 8:499-513.

37 Prusiner S B: 1997, Prion diseases and the BSE crisis. Science 278:245-251.

38 Prusiner S B: 1998, Prions. Proc Natl Acad Sci USA 95:13363-13383.

39 Prusiner S B, Groth D F, McKinley M P, et al.: 1981, Thiocyanate and hydroxyl ions inactivate the scrapie agent. Proc Natl Acad Sci USA 78:4606-4610.

40 Saegerman C, Speybroeck N, Roels S, et al.: 2004, Decision support tools for clinical diagnosis of disease in cows with suspected bovine spongiform encephalopathy. J Clin Microbiol 42:172-178.

41 Sander P, Hamann H, Drogemuller C, et al.: 2005, Bovine prion protein gene (PRNP) promoter polymorphisms modulate PRNP expression and may be responsible for differences in bovine spongiform encephalopathy susceptibility. J Biol Chem 280:37408-37414.

42 Sander P, Hamann H, Pfeiffer I, et al.: 2004, Analysis of sequence variability of the bovine prion protein gene (PRNP) in German cattle breeds. Neurogenetics 5:19-25.

43 Stack M J, Balachandran A, Chaplin M, et al.: 2004, The first Canadian indigenous case of bovine spongiform encephalopathy (BSE) has molecular characteristics for prion protein that are similar to those of BSE in the United Kingdom but differ from those of chronic wasting disease in captive elk and deer. Can Vet J 45:825-830.

44 Stack M J, Chaplin M J, Clark J: 2002, Differentiation of prion protein glycoforms from naturally occurring sheep scrapie, sheep-passaged scrapie strains (CH1641 and SSBP1), bovine spongiform encephalopathy (BSE) cases and Romney and Cheviot breed sheep experimentally inoculated with BSE using two monoclonal antibodies. Acta Neuropathol (Berl) 104:279-286.

45 Stevenson M A, Morris R S, Lawson A B, et al.: 2005, Area-level risks for BSE in British cattle before and after the July 1988 meat and bone meal feed ban. Prey Vet Med 69:129-144.

46 Thompson J D, Higgins D G, Gibson T J: 1994, CLUSTAL W: improving the sensitivity of progressive multiple sequence alignment through sequence weighting, position-specific gap penalties and weight matrix choice. Nucleic Acids Res 22:4673-4680.

47 Wear A, Henderson K, Webster K, Patel I: 2005, A comparison of rapid bovine spongiform encephalopathy testing methods on autolyzed bovine brain tissue. J Vet Diagn Invest 17:99-102.

48 Wells G A, McGill I S: 1992, Recently described scrapie-like encephalopathies of animals: case definitions. Res Vet Sci 53:1-10.

49 Wells G A, Wilesmith J W: 1995, The neuropathology and epidemiology of bovine spongiform encephalopathy. Brain Pathol 5:91-103.

50 Wilesmith J W, Ryan J B, Atkinson M J: 1991, Bovine spongiform encephalopathy: epidemiological studies on the origin. Vet Rec 128:199-203.

51 Wilesmith J W, Ryan J B, Hueston W D, Hoinville L J: 1992, Bovine spongiform encephalopathy: epidemiological features 1985 to 1990. Vet Rec 130:90-94.

52 Yamakawa Y, Hagiwara K, Nohtomi K, et al.: 2003, Atypical proteinase K-resistant prion protein (PrPres) observed in an apparently healthy 23-month-old Holstein steer. Jpn J Infect Dis 56:221-222.

53 Zhang C C, Steele A D, Lindquist S, Lodish H F: 2006, Prion protein is expressed on long-term repopulating hematopoietic stem cells and is important for their self-renewal. Proc Natl Acad Sci USA 103:2184-2189.

I claim:

1. A method for determining an allele of the gene encoding the prion protein in bovines comprising detecting the presence of an A nucleotide in a single nucleotide polymorphism in exon 3 of the bovine prion protein (Prnp) gene in a biological sample obtained from a bovine, wherein said single nucleotide polymorphism is at a position selected from the group consisting of a position corresponding to position 631 of SEQ ID NO: 3 wherein said Prnp gene in said biological sample has six octapeptide repeats, a position corresponding to position 631 of SEQ ID NO: 3 wherein said Prnp gene in said biological sample has five octapeptide repeats, and a position corresponding to position 631 of SEQ ID NO: 3 wherein said Prnp gene in said biological sample has seven octapeptide repeats, and further comprising removing from breeding or from human food and animal feed supplies those bovine wherein said A nucleotide is detected at said single nucleotide polymorphism.

2. The method of claim 1 wherein said single nucleotide polymorphism is at said position corresponding to position 631 of SEQ ID NO: 3 wherein said Prnp gene in said biological sample has six octapeptide repeats.

3. The method of claim 1 wherein said single nucleotide polymorphism is at said position corresponding to position 631 of SEQ ID NO: 3 wherein said Prnp gene in said biological sample has five octapeptide repeats.

4. The method of claim 1 wherein said single nucleotide polymorphism is at said position corresponding to position 631 of SEQ ID NO: 3 wherein said Prnp gene in said biological sample has seven octapeptide repeats.

5. The method of claim 1 wherein said biological sample is selected from the group consisting of genomic DNA, cDNA, RNA, and combinations thereof.

6. The method of claim 1 wherein said biological sample comprises genomic DNA.

7. The method of claim 2 wherein said biological sample comprises a DNA molecule that encompasses, or is encompassed by, said Prnp gene of SEQ ID NO: 3 or a complement thereof.

8. The method of claim 7 wherein said biological sample comprises genomic DNA molecules.

9. The method of claim 2 wherein said biological sample comprises an RNA molecule that is a transcript of a sequence that encompass, or are encompassed by, said Prnp gene of SEQ ID NO: 3 or a complement thereof.

10. The method of claim 1 wherein said bovine is *Bos Taurus* or *Bos indicus.*

11. The method of claim 10 wherein said bovine is a bull, cow or calf.

12. A method for identifying the genotypic status of a single nucleotide polymorphism in bovine comprising:

a) obtaining a nucleic acid sample from a bovine; and b) detecting the presence of an A nucleotide in a single nucleotide polymorphism in exon 3 of the bovine prion protein (Prnp) gene in said sample, wherein said single nucleotide polymorphism is at a position selected from the group consisting of a position corresponding to position 631 of SEQ ID NO: 3 wherein said Prnp gene in said biological sample has six octapeptide repeats, a position corresponding to position 631 of SEQ ID NO: 3 wherein said Prnp gene in said biological sample has five octapeptide repeats, and a position corresponding to position 631 of SEQ ID NO: 3 wherein said Prnp gene in said biological sample has seven octapeptide repeats; and c) removing from breeding or from human food and animal feed supplies those bovine wherein said A nucleotide is detected at said single nucleotide polymorphism;

further wherein said polymorphism encodes lysine (K) at amino acid 211 of said bovine prion protein when said protein comprises six octapeptide repeat region sequences, at amino acid 203 of said prion protein when said protein comprises five octapeptide repeat region sequences, and amino acid 219 of said prion protein when said protein comprises seven octapeptide repeat region sequences.

13. The method of claim 12 wherein said bovine prion protein comprises six octapeptide repeat region sequences.

14. The method of claim 12 wherein said bovine prion protein comprises five octapeptide repeat region sequences.

15. The method of claim 12 wherein said bovine prion protein comprises seven octapeptide repeat region sequences.

16. A method for identifying a bovine animal as having increased susceptibility to bovine spongiform encephalopathy, comprising detecting the presence of a lysine (K) at amino acid 211 of said bovine prion protein of SEQ ID NO: 14, correlating the detected presence of said lysine at said position with increased susceptibility to bovine spongiform encephalopathy, and removing from breeding or from human food and animal feed supplies those bovine wherein the presence of said lysine (K) is detected.

* * * * *